(12) United States Patent
Farritor et al.

(10) Patent No.: US 11,826,014 B2
(45) Date of Patent: *Nov. 28, 2023

(54) ROBOTIC SURGICAL DEVICES, SYSTEMS AND RELATED METHODS

(71) Applicant: Virtual Incision Corporation, Lincoln, NE (US)

(72) Inventors: Shane Farritor, Lincoln, NE (US); Dmitry Oleynikov, Omaha, NE (US); John Murphy, Pleasanton, CA (US); Sabrina Varanelli, Brooklyn, NY (US); Jeffrey Shasho, Brooklyn, NY (US); Nathan Wood, Lincoln, NE (US); Jack Wilson, Brooklyn, NY (US); Eleanora Pea Allen, New York, NY (US)

(73) Assignee: Virtual Incision Corporation, Lincoln, NE (US)

( * ) Notice: Subject to any disclaimer, the term of this patent is extended or adjusted under 35 U.S.C. 154(b) by 206 days.

This patent is subject to a terminal disclaimer.

(21) Appl. No.: 16/926,025

(22) Filed: Jul. 10, 2020

(65) Prior Publication Data
US 2020/0405412 A1   Dec. 31, 2020

Related U.S. Application Data

(63) Continuation of application No. 15/599,231, filed on May 18, 2017, now Pat. No. 10,751,136.
(Continued)

(51) Int. Cl.
*A61B 1/00*   (2006.01)
*A61B 34/30*   (2016.01)
(Continued)

(52) U.S. Cl.
CPC .............. *A61B 34/30* (2016.02); *A61B 1/008* (2013.01); *A61B 1/0016* (2013.01);
(Continued)

(58) Field of Classification Search
None
See application file for complete search history.

(56) References Cited

U.S. PATENT DOCUMENTS 2,858,947 A   11/1958   Chapman, Jr.
3,817,403 A   6/1974   Glachet et al.
(Continued)

FOREIGN PATENT DOCUMENTS

| CA | 2918531 A1 | 1/2015 |
|---|---|---|
| CN | 102499759 A | 6/2012 |

(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
(Continued)

*Primary Examiner* — Timothy J Neal
(74) *Attorney, Agent, or Firm* — Fredrikson & Byon, P.A.

(57) ABSTRACT

The various inventions relate to robotic surgical devices, consoles for operating such surgical devices, operating theaters in which the various devices can be used, insertion systems for inserting and using the surgical devices, and related methods.

20 Claims, 51 Drawing Sheets

Related U.S. Application Data

(60) Provisional application No. 62/338,375, filed on May 18, 2016.

(51) Int. Cl.

| | | |
|---|---|---|
| *A61B 17/02* | (2006.01) | |
| *A61B 90/00* | (2016.01) | |
| *A61B 1/06* | (2006.01) | |
| *A61B 34/32* | (2016.01) | |
| *A61B 34/00* | (2016.01) | |
| *A61B 1/005* | (2006.01) | |
| *A61B 1/008* | (2006.01) | |
| *A61B 1/045* | (2006.01) | |
| *A61B 1/05* | (2006.01) | |
| *A61B 18/12* | (2006.01) | |
| *A61B 18/14* | (2006.01) | |
| *A61B 17/00* | (2006.01) | |
| *A61B 90/11* | (2016.01) | |
| *A61B 17/29* | (2006.01) | |
| *A61B 90/57* | (2016.01) | |
| *A61B 90/50* | (2016.01) | |
| *A61B 17/34* | (2006.01) | |
| *A61B 1/313* | (2006.01) | |
| *A61B 18/00* | (2006.01) | |

(52) U.S. Cl.
CPC ........ *A61B 1/0052* (2013.01); *A61B 1/00128* (2013.01); *A61B 1/045* (2013.01); *A61B 1/051* (2013.01); *A61B 1/06* (2013.01); *A61B 17/02* (2013.01); *A61B 18/1206* (2013.01); *A61B 18/1482* (2013.01); *A61B 34/32* (2016.02); *A61B 34/76* (2016.02); *A61B 34/77* (2016.02); *A61B 90/37* (2016.02); *A61B 1/3132* (2013.01); *A61B 17/3423* (2013.01); *A61B 34/74* (2016.02); *A61B 90/11* (2016.02); *A61B 90/361* (2016.02); *A61B 2017/00101* (2013.01); *A61B 2017/00199* (2013.01); *A61B 2017/00309* (2013.01); *A61B 2017/00314* (2013.01); *A61B 2017/00327* (2013.01); *A61B 2017/00473* (2013.01); *A61B 2017/2906* (2013.01); *A61B 2017/347* (2013.01); *A61B 2018/00178* (2013.01); *A61B 2018/00595* (2013.01); *A61B 2018/1253* (2013.01); *A61B 2034/301* (2016.02); *A61B 2034/302* (2016.02); *A61B 2034/742* (2016.02); *A61B 2090/506* (2016.02); *A61B 2090/571* (2016.02)

(56) References Cited

U.S. PATENT DOCUMENTS

| | | |
|---|---|---|
| 3,870,264 A | 3/1975 | Robinson |
| 3,922,930 A | 12/1975 | Fletcher et al. |
| 3,971,266 A | 7/1976 | Inakura et al. |
| 3,989,952 A | 11/1976 | Timberlake et al. |
| 4,246,661 A | 1/1981 | Pinson |
| 4,258,716 A | 3/1981 | Sutherland |
| 4,278,077 A | 7/1981 | Mizumoto |
| 4,353,677 A | 10/1982 | Susnjara et al. |
| 4,538,594 A | 9/1985 | Boebel et al. |
| 4,568,311 A | 2/1986 | Miyaki |
| 4,576,545 A | 3/1986 | Maeda |
| 4,623,183 A | 11/1986 | Aomori |
| 4,636,138 A | 1/1987 | Gorman |
| 4,645,409 A | 2/1987 | Gorman |
| 4,684,313 A | 8/1987 | Minematsu et al. |
| 4,736,645 A | 4/1988 | Zimmer |
| 4,762,455 A | 8/1988 | Coughlan et al. |
| 4,771,652 A | 9/1988 | Zimmer |
| 4,852,391 A | 8/1989 | Ruch |
| 4,854,808 A | 8/1989 | Bisiach |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,984,959 A | 1/1991 | Kato |
| 4,990,050 A | 2/1991 | Tsuge et al. |
| 5,019,968 A | 5/1991 | Wang et al. |
| 5,036,724 A | 8/1991 | Rosheim |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,305,653 A | 4/1994 | Ohtani et al. |
| 5,307,447 A | 4/1994 | Asano et al. |
| 5,353,807 A | 10/1994 | DeMarco |
| 5,363,935 A | 11/1994 | Schempf et al. |
| 5,372,147 A | 12/1994 | Lathrop, Jr. et al. |
| 5,382,885 A | 1/1995 | Salcudean et al. |
| 5,441,494 A | 1/1995 | Oritz |
| 5,388,528 A | 2/1995 | Pelrine et al. |
| 5,397,323 A | 3/1995 | Taylor et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,667,354 A | 9/1997 | Nakazawa |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,833,656 A | 11/1998 | Smith et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,377 A | 4/1999 | Smith et al. |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |

(56) References Cited

U.S. PATENT DOCUMENTS

| | | |
|---|---|---|
| 5,911,036 A | 6/1999 | Wright et al. |
| 5,954,692 A | 9/1999 | Smith et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,106,521 A | 8/2000 | Blewett et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tiemey et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,450,992 B1 | 9/2002 | Cassidy |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,826,977 B2 | 12/2004 | Grover et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,793 B2 | 1/2005 | Brock et al. |
| 6,852,107 B2 | 2/2005 | Wang et al. |
| 6,853,879 B2 | 2/2005 | Sunaoshi |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |

(56) References Cited

U.S. PATENT DOCUMENTS

| | | |
|---|---|---|
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,963,792 B1 | 11/2005 | Green |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 6,999,852 B2 | 2/2006 | Green |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,155,316 B2 | 12/2006 | Sutherland et al. |
| 7,163,525 B2 | 1/2007 | Franer |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,403,836 B2 | 7/2008 | Aoyama |
| 7,438,702 B2 | 10/2008 | Hart et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,734,375 B2 | 6/2010 | Buehler et al. |
| 7,762,825 B2 | 7/2010 | Burbank et al. |
| 7,772,796 B2 | 8/2010 | Farritor et al. |
| 7,785,251 B2 | 8/2010 | Wilk |
| 7,785,294 B2 | 8/2010 | Hueil et al. |
| 7,785,333 B2 | 8/2010 | Miyamoto et al. |
| 7,789,825 B2 | 9/2010 | Nobis et al. |
| 7,789,861 B2 | 9/2010 | Franer |
| 7,794,494 B2 | 9/2010 | Sahatjian et al. |
| 7,865,266 B2 | 1/2011 | Moll et al. |
| 7,960,935 B2 | 6/2011 | Farritor et al. |
| 7,979,157 B2 | 7/2011 | Anvari |
| 8,021,358 B2 | 9/2011 | Doyle et al. |
| 8,179,073 B2 | 5/2012 | Farritor et al. |
| 8,231,610 B2 | 7/2012 | Jo et al. |
| 8,343,171 B2 | 1/2013 | Farritor et al. |
| 8,353,897 B2 | 1/2013 | Doyle et al. |
| 8,377,045 B2 | 2/2013 | Schena |
| 8,604,742 B2 | 12/2013 | Farritor et al. |
| 8,636,686 B2 | 1/2014 | Minnelli et al. |
| 8,679,096 B2 | 3/2014 | Farritor et al. |
| 8,827,337 B2 | 9/2014 | Murata et al. |
| 8,828,024 B2 | 9/2014 | Farritor et al. |
| 8,834,488 B2 | 9/2014 | Farritor et al. |
| 8,864,652 B2 | 10/2014 | Diolaiti et al. |
| 8,888,687 B2 | 11/2014 | Ostrovsky et al. |
| 8,968,332 B2 | 3/2015 | Farritor et al. |
| 8,974,440 B2 | 3/2015 | Farritor et al. |
| 8,986,196 B2 | 3/2015 | Larkin et al. |
| 9,010,214 B2 | 4/2015 | Markvicka et al. |
| 9,060,781 B2 | 6/2015 | Farritor et al. |
| 9,089,256 B2 | 7/2015 | Tognaccini et al. |
| 9,089,353 B2 | 7/2015 | Farritor et al. |
| 9,138,129 B2 | 9/2015 | Diolaiti |
| 9,198,728 B2 | 12/2015 | Wang et al. |
| 9,516,996 B2 | 12/2016 | Diolaiti et al. |
| 9,579,088 B2 | 2/2017 | Farritor et al. |
| 9,649,020 B2 | 5/2017 | Finlay |
| 9,717,563 B2 | 8/2017 | Tognaccini et al. |
| 9,743,987 B2 | 8/2017 | Farritor et al. |
| 9,757,187 B2 | 9/2017 | Farritor et al. |
| 9,770,305 B2 | 9/2017 | Farritor et al. |
| 9,789,608 B2 | 10/2017 | Itkowitz et al. |
| 9,814,640 B1 | 11/2017 | Khaligh |
| 9,816,641 B2 | 11/2017 | Bock-Aronson et al. |
| 9,849,586 B2 | 12/2017 | Rosheim |
| 9,857,786 B2 | 1/2018 | Cristiano |
| 9,888,966 B2 | 2/2018 | Farritor et al. |
| 9,956,043 B2 | 5/2018 | Farritor et al. |
| 10,008,017 B2 | 6/2018 | Itkowitz et al. |
| 10,111,711 B2 | 10/2018 | Farritor et al. |
| 10,137,575 B2 | 11/2018 | Itkowitz et al. |
| 10,159,533 B2 | 12/2018 | Moll et al. |
| 10,220,522 B2 | 3/2019 | Rockrohr |
| 10,258,425 B2 | 4/2019 | Mustufa et al. |
| 10,307,199 B2 | 6/2019 | Farritor et al. |
| 10,342,561 B2 | 7/2019 | Farritor et al. |
| 10,368,952 B2 | 8/2019 | Tognaccini et al. |
| 10,398,516 B2 | 9/2019 | Jackson et al. |
| 10,470,828 B2 | 11/2019 | Markvicka et al. |
| 10,507,066 B2 | 12/2019 | Dimaio et al. |
| 10,555,775 B2 | 2/2020 | Hoffman et al. |
| 10,582,973 B2 | 3/2020 | Wilson et al. |
| 10,695,137 B2 | 6/2020 | Farritor et al. |
| 10,729,503 B2 | 8/2020 | Cameron |
| 10,737,394 B2 | 8/2020 | Itkowitz et al. |
| 10,751,136 B2 * | 8/2020 | Farritor ............... A61B 1/0052 |
| 10,751,883 B2 | 8/2020 | Nahum |
| 10,806,538 B2 | 10/2020 | Farritor et al. |
| 10,966,700 B2 | 4/2021 | Farritor et al. |
| 11,032,125 B2 | 6/2021 | Farritor et al. |
| 11,298,195 B2 | 4/2022 | Ye et al. |
| 11,382,702 B2 | 7/2022 | Tognaccini et al. |
| 11,529,201 B2 | 12/2022 | Mondry et al. |
| 2001/0018591 A1 | 8/2001 | Brock et al. |
| 2001/0049497 A1 | 12/2001 | Kalloo et al. |

(56) References Cited

U.S. PATENT DOCUMENTS

| | | |
|---|---|---|
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0109780 A1 | 6/2003 | Coste-Maniere et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0159535 A1 | 8/2003 | Grover et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0225479 A1 | 12/2003 | Waled |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0177026 A1 | 8/2005 | Hoeg et al. |
| 2005/0234294 A1 | 10/2005 | Saadat et al. |
| 2005/0234435 A1 | 10/2005 | Layer |
| 2005/0272977 A1 | 12/2005 | Saadat et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0079889 A1 | 4/2006 | Scott |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0189845 A1 | 8/2006 | Maahs et al. |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258938 A1 | 11/2006 | Hoffman et al. |
| 2006/0258954 A1 | 11/2006 | Timberlake et al. |
| 2006/0261770 A1 | 11/2006 | Kishi et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0088340 A1 | 4/2007 | Brock et al. |
| 2007/0106113 A1 | 5/2007 | Ravo |
| 2007/0106317 A1 | 5/2007 | Shelton et al. |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2007/0287884 A1 | 12/2007 | Schena |
| 2008/0004634 A1 | 1/2008 | Farritor et al. |
| 2008/0015565 A1 | 1/2008 | Davison |
| 2008/0015566 A1 | 1/2008 | Livneh |
| 2008/0021440 A1 | 1/2008 | Solomon |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0071289 A1 | 3/2008 | Cooper et al. |
| 2008/0071290 A1 | 3/2008 | Larkin et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0168639 A1 | 7/2008 | Otake et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0002414 A1 | 1/2009 | Shibata et al. |
| 2009/0012532 A1 | 1/2009 | Blackwell et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0192524 A1 | 7/2009 | Itkowitz et al. |

(56) References Cited

U.S. PATENT DOCUMENTS

| | | |
|---|---|---|
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0299143 A1 | 12/2009 | Conlon et al. |
| 2009/0305210 A1 | 12/2009 | Guru et al. |
| 2009/0326322 A1 | 12/2009 | Diolaiti |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0026347 A1 | 2/2010 | Iizuka |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0101346 A1 | 4/2010 | Johnson et al. |
| 2010/0130986 A1 | 5/2010 | Mailloux et al. |
| 2010/0139436 A1 | 6/2010 | Kawashima et al. |
| 2010/0185212 A1 | 7/2010 | Sholev |
| 2010/0198231 A1 | 8/2010 | Manzo et al. |
| 2010/0204713 A1 | 8/2010 | Ruiz Morales |
| 2010/0245549 A1 | 9/2010 | Allen et al. |
| 2010/0250000 A1 | 9/2010 | Blumenkranz et al. |
| 2010/0262162 A1 | 10/2010 | Omori |
| 2010/0263470 A1 | 10/2010 | Bannasch et al. |
| 2010/0274079 A1 | 10/2010 | Kim et al. |
| 2010/0292691 A1 | 11/2010 | Brogna |
| 2010/0301095 A1 | 12/2010 | Shelton, IV et al. |
| 2010/0318059 A1 | 12/2010 | Farritor et al. |
| 2010/0331856 A1 | 12/2010 | Carlson et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0075693 A1 | 3/2011 | Kuramochi et al. |
| 2011/0077478 A1 | 3/2011 | Freeman et al. |
| 2011/0082365 A1 | 4/2011 | Mcgrogan et al. |
| 2011/0098529 A1 | 4/2011 | Ostrovsky et al. |
| 2011/0107866 A1 | 5/2011 | Oka et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238079 A1 | 9/2011 | Hannaford et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2011/0276046 A1 | 11/2011 | Heimbecher et al. |
| 2012/0016175 A1 | 1/2012 | Roberts et al. |
| 2012/0029727 A1 | 2/2012 | Malik |
| 2012/0035582 A1 | 2/2012 | Nelson et al. |
| 2012/0059392 A1 | 3/2012 | Diolaiti |
| 2012/0078053 A1 | 3/2012 | Phee et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0221147 A1 | 8/2012 | Goldberg et al. |
| 2012/0253515 A1 | 10/2012 | Coste-Maniere et al. |
| 2013/0001970 A1 | 1/2013 | Suyama et al. |
| 2013/0041360 A1 | 2/2013 | Farritor et al. |
| 2013/0055560 A1 | 3/2013 | Nakasugi et al. |
| 2013/0125696 A1 | 5/2013 | Long |
| 2013/0131695 A1* | 5/2013 | Scarfogliero .......... A61B 34/30 606/130 |
| 2013/0178867 A1 | 7/2013 | Farritor et al. |
| 2013/0282023 A1 | 10/2013 | Burbank et al. |
| 2013/0304084 A1 | 11/2013 | Beira et al. |
| 2013/0325030 A1 | 12/2013 | Hourtash et al. |
| 2013/0345717 A1 | 12/2013 | Markvicka et al. |
| 2013/0345718 A1 | 12/2013 | Crawford et al. |
| 2014/0039515 A1 | 2/2014 | Mondry et al. |
| 2014/0046340 A1 | 2/2014 | Wilson et al. |
| 2014/0055489 A1 | 2/2014 | Itkowitz et al. |
| 2014/0058205 A1 | 2/2014 | Frederick et al. |
| 2014/0100587 A1 | 4/2014 | Farritor et al. |
| 2014/0137687 A1 | 5/2014 | Nogami et al. |
| 2014/0221749 A1 | 8/2014 | Grant et al. |
| 2014/0232824 A1 | 8/2014 | Dimaio et al. |
| 2014/0276944 A1 | 9/2014 | Farritor et al. |
| 2014/0303434 A1 | 10/2014 | Farritor et al. |
| 2014/0371762 A1 | 12/2014 | Farritor et al. |
| 2015/0051446 A1* | 2/2015 | Farritor .................. A61B 34/30 600/102 |
| 2015/0157191 A1 | 6/2015 | Phee et al. |
| 2015/0223896 A1 | 8/2015 | Farritor et al. |
| 2015/0297299 A1 | 10/2015 | Yeung et al. |
| 2016/0066999 A1 | 3/2016 | Forgione et al. |
| 2016/0135898 A1 | 5/2016 | Frederick et al. |
| 2016/0291571 A1 | 10/2016 | Cristiano |
| 2016/0303745 A1 | 10/2016 | Rockrohr |
| 2017/0014197 A1 | 1/2017 | Mccrea et al. |
| 2017/0035526 A1 | 2/2017 | Farritor et al. |
| 2017/0078583 A1 | 3/2017 | Haggerty et al. |
| 2017/0252096 A1 | 9/2017 | Felder et al. |
| 2017/0354470 A1 | 12/2017 | Farritor et al. |
| 2018/0132956 A1 | 5/2018 | Cameron |
| 2018/0153578 A1 | 6/2018 | Cooper et al. |
| 2018/0338777 A1 | 11/2018 | Bonadio et al. |
| 2019/0090965 A1 | 3/2019 | Farritor et al. |
| 2019/0209262 A1 | 7/2019 | Mustufa et al. |
| 2019/0327394 A1 | 10/2019 | Ramirez Luna et al. |
| 2020/0214775 A1 | 7/2020 | Farritor et al. |
| 2020/0330175 A1 | 10/2020 | Cameron |
| 2020/0368915 A1 | 11/2020 | Itkowitz et al. |

FOREIGN PATENT DOCUMENTS

| | | |
|---|---|---|
| CN | 102821918 | 12/2012 |
| CN | 104523309 A | 4/2015 |
| CN | 104582600 A | 4/2015 |
| CN | 104622528 A | 5/2015 |
| CN | 204337044 U | 5/2015 |
| CN | 105025826 A | 11/2015 |
| DE | 102010040405 | 3/2012 |
| EP | 105656 A2 | 4/1984 |
| EP | 279591 A1 | 8/1988 |
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| EP | 2684528 A1 | 1/2014 |
| EP | 2123225 B1 | 12/2014 |
| EP | 2815705 A1 | 12/2014 |
| EP | 2881046 A2 | 6/2015 |
| EP | 2937047 A1 | 10/2015 |
| JP | S59059371 A | 4/1984 |
| JP | S61165061 A | 7/1986 |
| JP | S62068293 A | 3/1987 |
| JP | H04-144533 A | 5/1992 |
| JP | 05-115425 | 5/1993 |
| JP | 2006508049 | 9/1994 |
| JP | H06-507809 A | 9/1994 |
| JP | H06-508049 A | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2002000524 A | 1/2002 |
| JP | 2003220065 | 8/2003 |
| JP | 2004144533 | 5/2004 |
| JP | 2004-180781 | 7/2004 |
| JP | 2004283940 A | 10/2004 |
| JP | 2004322310 | 11/2004 |
| JP | 2004329292 | 11/2004 |
| JP | 2006507809 | 3/2006 |
| JP | 2009106606 | 5/2009 |
| JP | 2009297809 A | 12/2009 |
| JP | 2010533045 | 10/2010 |

(56) References Cited

FOREIGN PATENT DOCUMENTS

| | | |
|---|---|---|
| JP | 2010536436 | 12/2010 |
| JP | 2011504794 | 2/2011 |
| JP | 2011045500 | 3/2011 |
| JP | 2011115591 | 6/2011 |
| JP | 2012504017 A | 2/2012 |
| JP | 2012176489 A | 9/2012 |
| JP | 5418704 B1 | 2/2014 |
| JP | 2015526171 A | 9/2015 |
| JP | 5959371 B2 | 8/2016 |
| JP | 2016213937 A | 12/2016 |
| JP | 2017113837 A | 6/2017 |
| JP | 6268293 B2 | 1/2018 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009014917 A2 | 1/2009 |
| WO | 2009023851 | 2/2009 |
| WO | 2009144729 | 12/2009 |
| WO | 2009158164 A1 | 12/2009 |
| WO | 2010039394 A1 | 4/2010 |
| WO | 2010042611 A1 | 4/2010 |
| WO | 2010046823 A1 | 4/2010 |
| WO | 2010050771 | 5/2010 |
| WO | 2010083480 A2 | 7/2010 |
| WO | 2011075693 | 6/2011 |
| WO | 2011118646 | 9/2011 |
| WO | 2011135503 | 11/2011 |
| WO | 2011163520 A2 | 12/2011 |
| WO | 2013009887 | 1/2013 |
| WO | 2013052137 A2 | 4/2013 |
| WO | 2013106569 A2 | 7/2013 |
| WO | 2014011238 | 1/2014 |
| WO | 2014025399 A1 | 2/2014 |
| WO | 2014144220 A1 | 9/2014 |
| WO | 2014146090 A1 | 9/2014 |
| WO | 2015009949 A2 | 1/2015 |
| WO | 2015031777 A1 | 3/2015 |
| WO | 2015088655 A1 | 6/2015 |
| WO | 2016077478 A1 | 5/2016 |
| WO | 2017024081 A1 | 2/2017 |
| WO | 2017064303 A1 | 4/2017 |
| WO | 2017201310 A1 | 11/2017 |
| WO | 2018045036 A1 | 3/2018 |

OTHER PUBLICATIONS

Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Dumpert et al., "Stereoscopic In Vivo Surgical Robots," IEEE Sensors Special Issue on In Vivo Sensors for Medicine, Jan. 2007, 10 pp.
Green, "Telepresence Surgery", Jan. 1, 1995, Publisher: IEEE Engineering in Medicine and Biology.
Cleary et al., "State of the Art in Surgical Rooties: Clinical Applications and Technology Challenges", "Computer Aided Surgery", Jan. 1, 2002, pp. 312-328, vol. 6.
Stoianovici et al., "Robotic Tools for Minimally Invasive Urologic Surgery", Jan. 1, 2002, pp. 1-17.
Franzino, "The Laprotek Surgical System and the Next Generation of Robotics," Surg Clin North Am, 2003 83(6): 1317-1320.
Franklin et al., "Prospective Comparison of Open vs. Laparoscopic Colon Surgery for Carcinoma: Five-Year Results," Dis Colon Rectum, 1996; 39: S35-S46.
Flynn et al, "Tomorrow's surgery: micromotors and microrobots for minimally invasive procedures," Minimally Invasive Surgery & Allied Technologies, 1998; 7(4): 343-352.
Fireman et al., "Diagnosing small bowel Crohn's desease with wireless capsule endoscopy," Gut 2003; 52: 390-392.
Fearing et al., "Wing Transmission for a Micromechanical Flying Insect," Proceedings of the 2000 IEEE International Conference to Robotics & Automation, Apr. 2000; 1509-1516.
Faraz et al., "Engineering Approaches to Mechanical and Robotic Design for Minimaly Invasive Surgery (MIS)," Kluwer Academic Publishers (Boston), 2000, 13pp.
Falcone et al., "Robotic Surgery," Clin. Obstet. Gynecol. 2003, 46(1): 37-13.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Dumpert et al., "Improving in Vivo Robot Visioin Quality," from the Proceedings of Medicine Meets Virtual Realtiy, Long Beach, CA, Jan. 26-29, 2005. 1 pg.
Dakin et al., "Comparison of laparoscopic skills performance between standard instruments and two surgical robotic systems," Surg Endosc., 2003; 17: 574-579.
Cuschieri, "Technology for Minimal Access Surgery," BMJ, 1999, 319: 1-6.
Grady, "Doctors Try New Surgery for Gallbladder Removal," The New York Times, Apr. 20, 2007, 3 pp.
Choi et al., "Flexure-based Manipulator for Active Handheld Microsurgical Instrument," Proceedings of the 27th Annual International

(56) References Cited

OTHER PUBLICATIONS

Conference of the IEEE Engineering in Medicine and Biology Society (EMBS), Sep. 2005, 4pp.

Chanthasopeephan et al., (2003), "Measuring Forces in Liver Cutting: New Equipment and Experimenal Results," Annals of Biomedical Engineering 31: 1372-1382.

Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.

Guber et al., "Miniaturized Instrument Systems for Minimally Invasive Diagnosis and Therapy," Biomedizinische Technic. 2002, Band 47, Erganmngsband 1: 198-201.

Tendick et al., "Applications of Micromechatronics in Minimally Invasive Surgery," IEEE/ASME Transactions on Mechatronics, 1998; 3(1): 34-42.

Thomann et al., "The Design of a new type of Micro Robot for the Intestinal Inspection," Proceedings of the 2002 IEEE Intl. Conference on Intelligent Robots and Systems, Oct. 2002: 1385-1390.

U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.

Worn et al., "Espirit Project No. 33915: Miniaturised Robot for Micro Manipulation (MINIMAN)," Nov. 1998, http://www.pr.ira.ujka.de/-microbot/miniman.

Way et al., editors, "Fundamentals of Laparoscopic Surgery," Churchill Livingstone Inc., 1995; 14 pp.

Wolfe et al. (1991), Endoscopic Cholecystectomy: An analysis of Complications, Arch. Surg. 1991; 126: 1192-1196.

Xu et al. "System Design of an Insertable Robotic Effector Platform for Single Access (SPA) Surgery", The 2009 IEEE/RSJ International Conference on Intelligent Robots and Systems, Oct. 11-15, 2009, St. Louis MO USA pp. 5546-5552.

Yu, BSN, RN, "M2ATM Capsule Endoscopy A Breakthrough Diagnostic Tool for Small Intestine Imagining "vol. 25, No. 1, 2001, Gastroenterology Nursing, pp. 24-27.

Yu et al., "Microrobotic Cell Injection," Proceedings of the 2001 IEEE International Conference on Robotics and Automation, May 2001: 620-625.

Park et al., "Experimental studies of transgastric gallbladder surgery: cholecystectomy and cholecystogastric anastomosis (videos)," Gastrointestinal Endoscopy, 2005; 61 (4): 601-606.

Park et al., "Trocar-less Instrumentation for Laparoscopy: Magnetic Positioning of Intra-abdominal Camera and Retractor," Ann Surg, Mar. 2007; 245(3): 379-384.

Patronik et al., "Crawling on the Heart: A Mobile Robotic Device for Minimally Invasive Cardiac Interventions," MICCAI, 2004, pp. 9-16.

Patronik et al., "Development of a Tethered Epicardial Crawler for Minimally Invasive Cardiac Therapies," IEEE, pp. 239-240, 2004.

Patronik et al., "Preliminary evaluation of a mobile robotic device for navigation and intervention on the beating heart," Computer Aided Surgery, 10(4): 225-232, Jul. 2005.

Peirs et al., "A miniature manipulator for integration in a self-propelling endoscope," Sensors and Actuators A, 2001, 92: 343-349.

Peters, "Minimally Invasive Colectomy: Are the Potential Benefits Realized?" Dis Colon Rectum 1993; 36: 751-756.

Phee et al., "Development of Microrobotic Devices for Locomotion in the Human GastrointestinalTract," International Conference on Computational Intelligence, Robotics and Autonomous Systems (CI RAS 2001), Nov. 28-30, (2001), Singapore.

Phee et al., "Analysis and Development of Locomotion Devices for the Gastrointestinal Tract," IEEE Transactions on Biomedical Engineering, vol. 49, No. 6, Jun. 2002: 613-616.

Platt et al., "In Vivo Robotic Cameras can Enhance Imaging Capability During Laparoscopic Surgery," from the Proceedings of the Society of American Gastrointestinal Endoscopic Surgeons (SAGES) Scientific Conference, Ft. Lauderdale, FL, Apr. 13-16, 2005; 1 pg.

Qian Huan et al., "Multi-joint Single-wound Minimally Invasive Abdominal Surgery Robot Design," Mechanical Design and Manufacturing, May 8, 2014, pp. 134-137.

Rentschler et al., "In vivo Mobile Surgical Robotic Task Assistance," 1 pg.

Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28—Oct. 2, 2004; pp. 1-9.

Rentschler et al., "In Vivo Robots for Laparoscopic Surgery," Studies in Health Technology and Infonnatics —Medicine Meets Virtual Reality, ISO Press, Newport Beach, CA, 2004a, 98: 316-322.

Rentschler et al., "Toward In Vivo Mobility," Studies in Health Technology and Infonnatics—Medicine Meets Virtual Reality, ISO Press, Long Beach, CA, 2005a, III: 397-403.

Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.

Rentschler et al., "Modeling, Analysis, and Experimental Study of In Vivo Wheeled RoboticMobility," IEEE Transactions on Robotics, 22 (2): 308-321, 2005c.

Rentschler, et al. "Miniature in vivo robots for remote and harsh environments," IEEE Transaction on Information Technology in Biomedicine, Jan. 2006; 12(1): pp. 66-75.

Rentschler et al., "Mechanical Design of Robotic In Vivo Wheeled Mobility," ASME Journal ofMechanical Design, 2006a; pp. 1-11, Accepted.

Rentschler et al., "Mobile In Vivo Camera Robots Provide Sole Visual Feedback for Abdominal Exploration and Cholecystectomy," Journal of Surgical Endoscopy, 20-1: 135-138, 2006b.

Rentschler et al., "Natural Orifice Surgery with an Endoluminal Mobile Robot," The Society ofAmerican Gastrointestinal Endoscopic Surgeons, Dallas, TX, Apr. 2006d.

Rentschler et al., "Mobile In Vivo Biopsy and Camera Robot," Studies in Health and Infonnatics Medicine Meets Virtual Reality, vol. 119: 449-454, IOS Press, Long Beach, CA, 2006e.

Rentschler et al., "Mobile In Vivo Biopsy Robot," IEEE International Conference on Robotics and Automation, Orlando, Florida, May 2006; 4155-4160.

Rentschler et al., "In vivo Robotics during the NEEMO 9 Mission," Medicine Meets Virtual Reality, Feb. 2007; 1 pg.

Rentschler et al., "An In Vivo Mobile Robot for Surgical Vision and Task Assistance," Journal of Medical Devices, Mar. 2007; vol. 1: 23-29.

Riviere et al., "Toward Active Tremor Canceling in Handheld Microsurgical Instruments," IEEE Transactions on Robotics and Automation, Oct. 2003, 19(5): 793-800.

Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.

Rosen et al., "Task Decomposition of Laparoscopic Surgery for Objective Evaluation of SurgicalResidents' Learning Curve Using Hidden Markov Model," Computer Aided Surgery, vol. 7, pp. 49-61, 2002.

Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washin!=)ton, DC, pp. 1876-1881, May 2002.

Rosen et al., Objective Evaluation of Laparoscopic Skills Based on Haptic Information and Tool/Tissue Interactions, Computer Aided Surgery, vol. 7, Issue 1, pp. 49-61, Jul. 2002.

(56) References Cited

OTHER PUBLICATIONS

Rosen et al., "Spherical Mechanism Analysis of a Surgical Robot for Minimally Invasive Surgery—Analytical and Experimental Approaches," Studies in Health Technology and Infonnatics-Medicine Meets Virtual Reality, pp. 442-448, Jan. 2005.
Ruurda et al., "Feasibility of Robot-Assisted Laparoscopic Surgery," Surgical Laparoscopy, Endoscopy & Percutaneous Techniques, 2002; 12(1):41-45.
Ruurda et al., "Robot-Assisted surgical systems: a new era in laparoscopic surgery," Ann R. Coll Surg Engl. 2002; 84: 223-226.
Sackier et al., "Robotically assisted laparoscopic surgery," Surgical Endoscopy, 1994; 8:63-6.
Salky, "What is the Penetration of Endoscopic Techniques into Surgical Practice?" Digestive Surgery 2000; 17: 422-426.
Satava, "Surgical Robotics: The Early Chronicles," Surgical Laparoscopy, Endoscopy & Percutaneous Techniques, 2002; 12(1):6-16.
Schippers et al., (1996), "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Sodeyama et al., A shoulder structure of muscle-driven humanoid with shoulder blades, 2005, IEEE, pp. 1-6 (Year: 2005).
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al., "Long-term Pain: Less Common After Laparoscopic than Open Cholecystectomy," British Journal of Surgery, 1994; 81: 1368-1370.
Strong et al., "*Efficacy of Novel Robotic Camera* vs. *a Standard Laproscopic Camera*," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-87.
Tendick et al., (1993), "Sensing and Manipulation Problems in Endoscopic Surgery: Experiment, Analysis, and Observation," Presence 2(1): 66-81.
Abbou et al., "Laparoscopic Radical Prostatectomy with a Remote Controlled Robot," The Journal of Urology, Jun. 2001; 165: 1964-1966.
Albers et al., Design and development process of a humanoid robot upper body through experimentation, 2004, IEEE, pp. 77-92 (Year: 2004).
Crystal Eyes, http://www.reald.com, 2007 (Stereo 3D visualization for CAVEs, theaters and immersive environments), 1 pg.
Definition of Individually. Dictionary.com, retrieved on Aug. 9, 2016; Retrieved from the Internet: <http://www.dictionary.com/browse/individually>.
Glukhovsky et al., "The development and application of wireless capsule endoscopy," Int. J. Med. Robot. Comput. Assist. Surgery, 2004; I(1): 114-123.
Gong et al., "Wireless endoscopy," Gastrointestinal Endoscopy 2000; 51 (6): 725-729.
Gopura et al., Mechanical designs of active upper-limb exoskeleton robots: State-of-the-art and design difficulties, 2009, IEEE, pp. 178-187 (Year: 2009).
Gopura et al., A brief review on upper extremity robotic exoskeleton systems, 2011, IEEE, pp. 346-351 (Year: 2011).
Guo et al., "Micro Active Guide Wire Catheter System- Characteristic Evaluation, Electrical Model* and Operability Evaluation of Micro Active Catheter," Proceedings of the 1996 IEEE International Conference on Robotics and Automation, Apr. 1996; 2226-2231.
Guo et al., "Fish-like Underwater Microrobot with 3 DOF," Proceedings of the 2002 IEEE International Conference on Robotics & Automation, May 2002; 738-743.
Hanly et al., "Robotic Abdominal Surgery," The American Journal of Surgery, 2004; 188 (Suppl.to Oct. 1994); 19S-26S.
Hanly et al., "Value of the SAGES Learning Center in introducing new technology," Surgical Endoscopy, 2004; 19(4): 477-483.
Heikkinen et al., "Comparison of laparoscopic and open Nissen fundoplication two years after operation: A prospective randomized trial," Surgical Endoscopy, 2000; 14:1019-1023.
Hissink, "Olympus Medical develops capsule camera technology," Dec. 2004, accessed Aug. 29, 2007, http://wwww.letsgodigital.org, 3 pp.
Horgan et al., "Technical Report: Robots in Laparoscopic Surgery," Journal of Laparoendoscopic & Advanced Surgical Techniques, 2001; 11(6): 415-419.
Ishiyama et al., "Spiral-type Micro-machine for Medical Applications," 2000 International Symposium on Micromechatronics and Human Science, 2000; 65-69.
Jagannath et al., "Peroral transgastric endoscopic ligation of fallopian tubes with long-term survival in a porcine model," Gastrointestinal Endoscopy, 2005; 61 (3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan .- Feb. 2001: 94-104.
Kantsevoy et al., "Transgastric endoscopic splenectomy," Surgical Endoscopy, 2006; 20: 522-525.
Kantsevoy et al., "Endoscopic gastrojejunostomy with survival in a porcine model," Gastrointestinal Endoscopy, 2005; 62(2): 287-292.
Kazemier et al. (1998), "Vascular Injuries During Laparoscopy," J. Am. Coli. Surg. 186(5): 604-5.
Keller et al., Design of the pediatric arm rehabilitation robot ChARMin, 2014, IEEE, pp. 530-535 (Year: 2014).
Kim, "Early Experience with Telemanipulative Robot-Assisted Laparoscopic Cholecystectomy Using da Vinci," Surgical Laparoscopy, Endoscopy & Percutaneous Techniques, 2002; 12(1): 33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136: 180-184.
Leggett et al. (2002), "Aortic injury during laparoscopic Fundoplication," Surg. Endoscopy 16(2): 362.
Li et al. (2000), "Microvascular Anastomoses Performed in Rats Using a Microsurgical Telemanipulator," Comp. Aid. Surg., 5: 326-332.
Liem et al., "Comparison of Conventional Anterior Surgery and Laparoscopic Surgery for Inguinal-hernia Repair," New England Journal of Medicine, 1997; 336 (22): 1541-1547.
Lou Cubrich, "A Four-DOF Laparo-Endoscopic Single Site Platform for Rapidly-Developing Next Generation Surgical Robotics", Journal of Medical Robotics Research, vol. 1, No. 4, 2016, 165006-1 - 165006-15.
Macfarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.

(56) References Cited

OTHER PUBLICATIONS

Mei et al., "Wireless Drive and Control of a Swimming Microrobot," Proceedings of the 2002 IEEE International Conference on Robotics & Automation, May 2002: 1131-1136.

Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.

Melvin et al., "*Computer-Enhanced* vs. *Standard Laparoscopic Antireflux Surgery*," J Gastrointest Surg 2002; 6: 11-16.

Menciassi et al., "Locomotion of a Leffed Capsule in the Gastro-intestinal Tract: Theoretical Study and Preliminary Technological Results," IEEE Int. Conf. on Engineering in Medicine and Biology, San Francisco, CA, pp. 2767-2770, Sep. 2004.

Menciassi et al., "Shape memory alloy clamping devices of a capsule for monitoring tasks in the gastrointestinal tract," J. Micromech. Microeng, 2005; 15: 2045-2055.

Meron, "The development of the swallowable video capsule (M2A)," Gastrointestinal Endoscopy 2000; 52 6: 817-819.

Micron, http://www.micron.com, 2006, 1/4-inch VGA NTSC/PAL CMOS Digital Image Sensor, 98 pp.

Midday Jeff et al., "Material Handling System for Robotic natural Orifice Surgery,", Proceedings of the 2011 Design of medical Devices Conference, Apr. 12-14, 2011, Minneapolis, MN 4 pages.

Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp., 2004.

Munro (2002), "Laparoscopic access: complications, technologies, and techniques," Curro Opin. Obstet. Gynecol., 14 (4): 365-74.

Nio et al., "Efficiency of manual vs robotical (Zeus) assisted laparoscopic surgery in the performance of standardized tasks," Surg Endosc, 2002; 16: 412-415.

Oleynikov et al., "In Vivo Camera Robots Provide Improved Vision for Laparoscopic Surgery," Computer Assisted Radiology and Surgery (CARS), Chicago, IL, Jun. 23-26, 2004b.

Oleynikov et al., "Miniature Robots Can Assist in Laparoscopic Cholecystectomy," Journal of Surgical Endoscopy, 19-4: 473-476, 2005.

Oleynikov et al., "In Vivo Robotic Laparoscopy," Surgical Innovation, Jun. 2005, 12(2): 177-181.

O'Neill, "Surgeon takes new route to gallbladder," The Oregonian, Jun. 2007; 2 pp.

Orlando et al. (2003), "Needle and Trocar Injuries in Diagnostic Laparoscopy under Local Anesthesia: What Is the True Incidence of These Complications?" Journal of Laparoendoscopic & Advanced Surgical Techniques, 13(3): 181-184.

Palm. William. "Rapid Prototyping Primer" May 1998 (revised Jul. 30, 2002) (http://www.me.psu.edu/lamancusa/rapidpro/primer/chapter2.htm).

\* cited by examiner

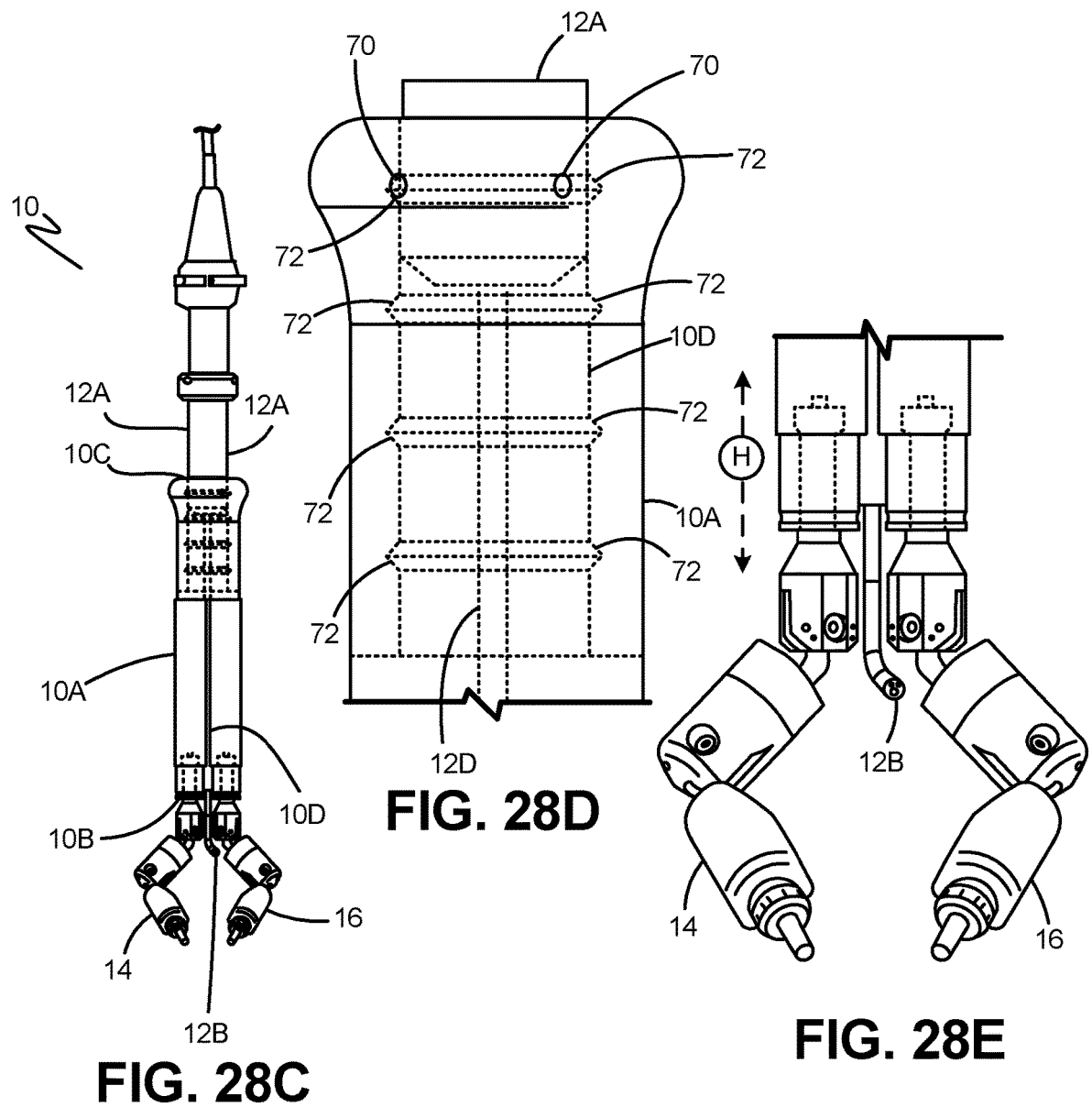

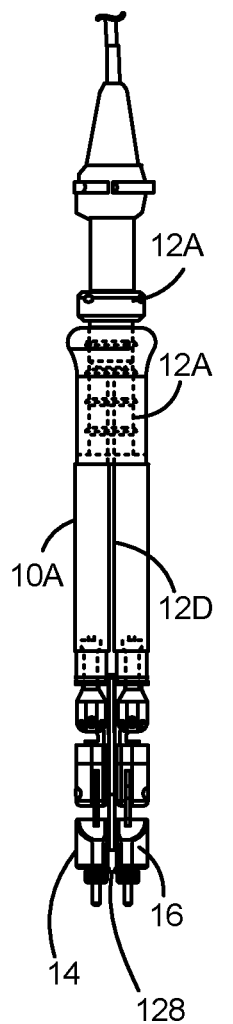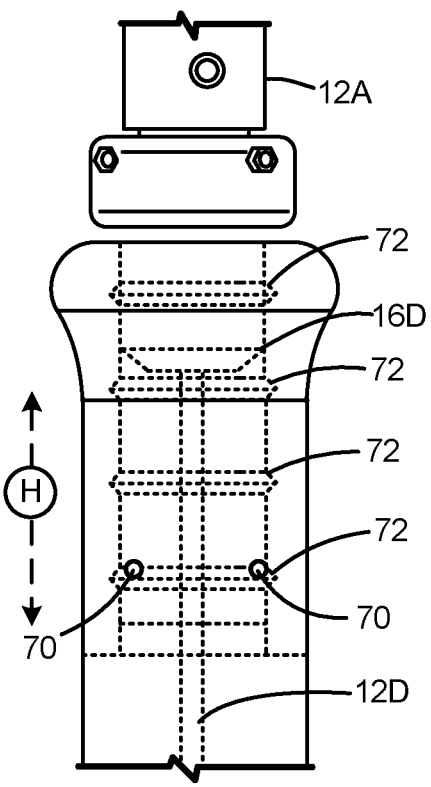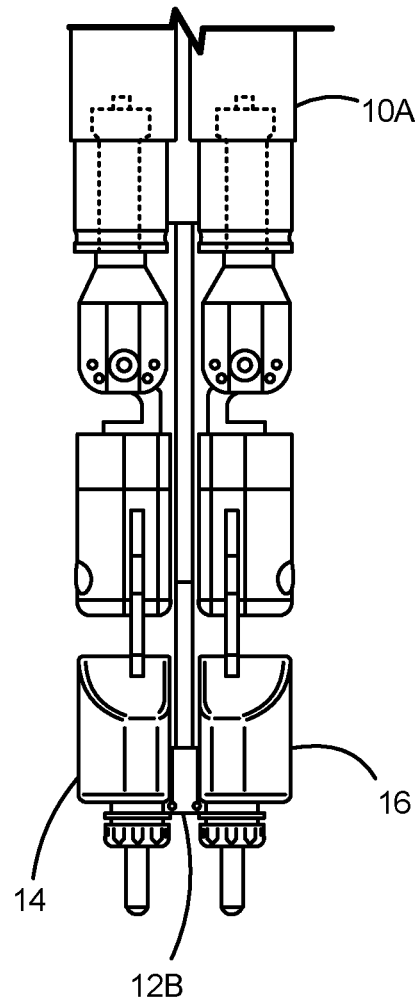
FIG. 28F
FIG. 28G
FIG. 28H

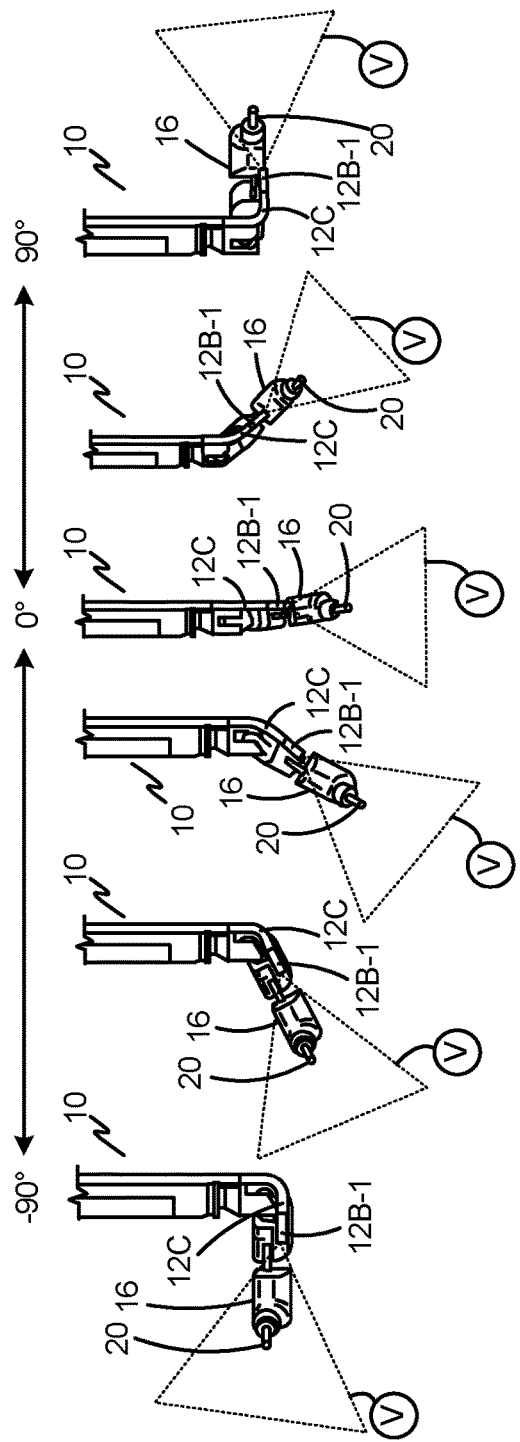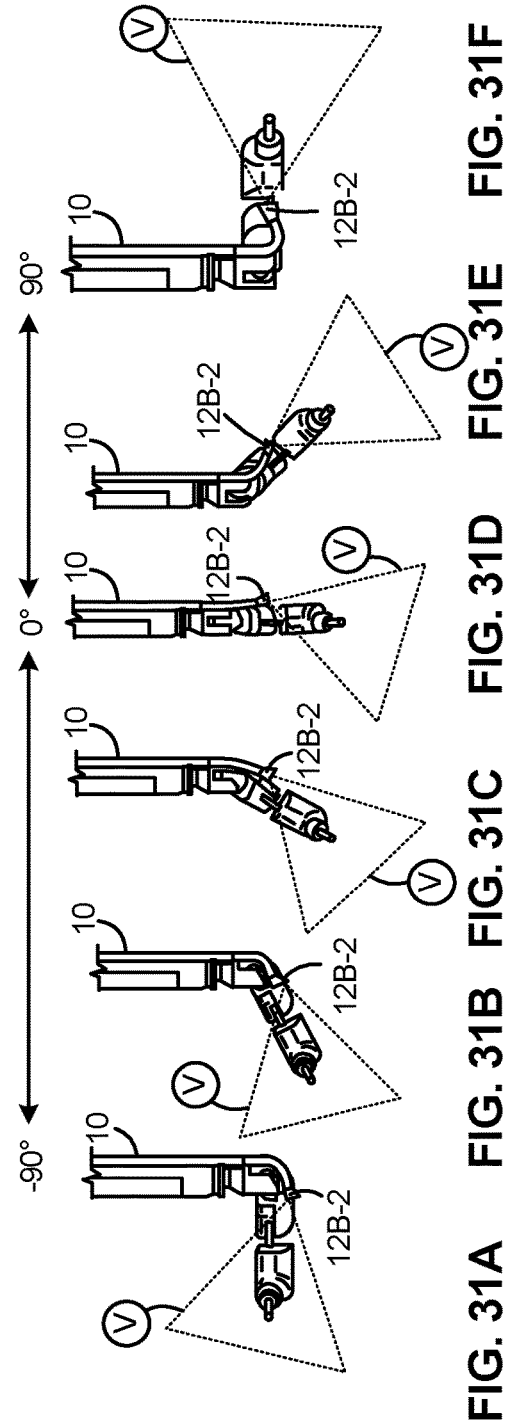

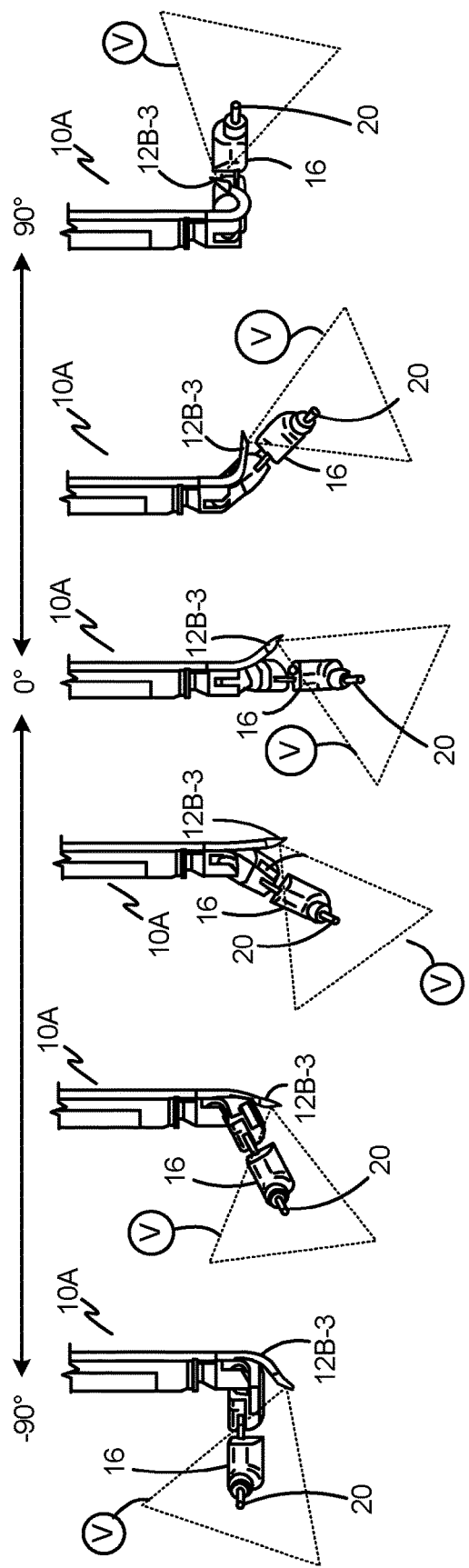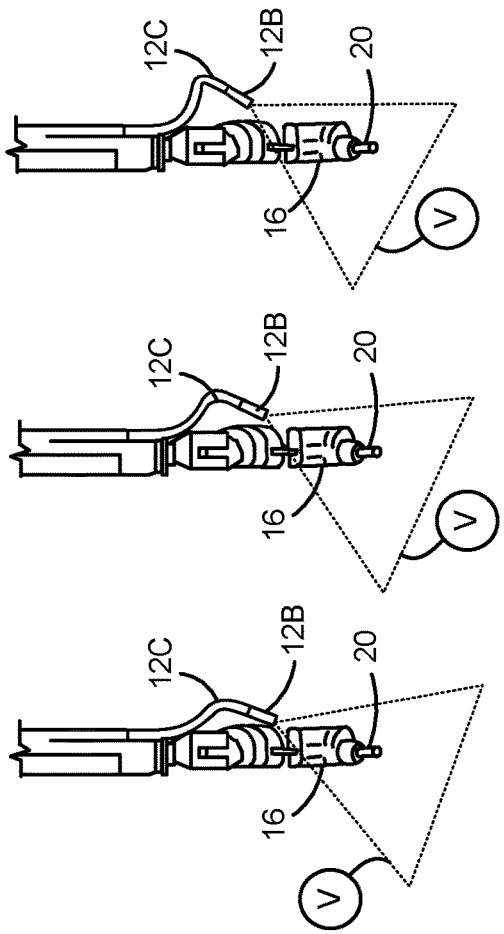

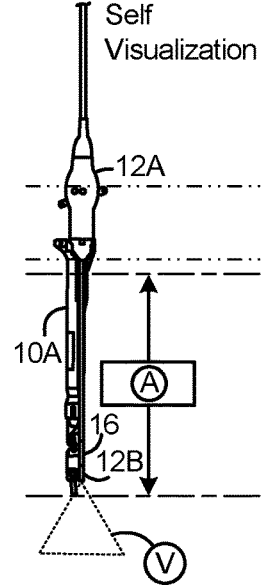 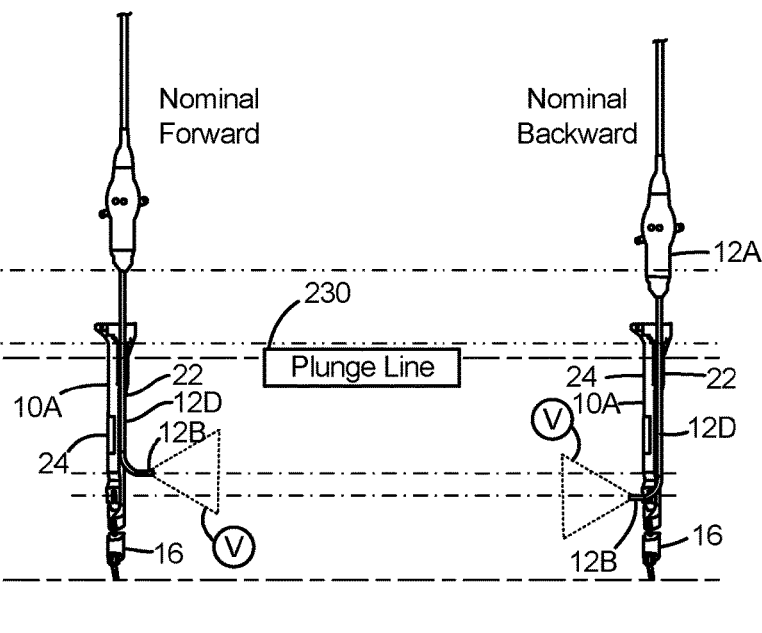
FIG. 35A  FIG. 35B  FIG. 35C

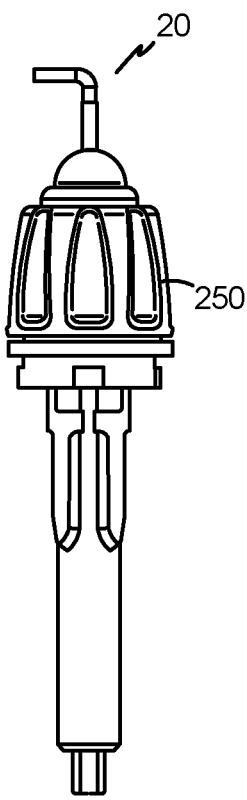
FIG. 36A
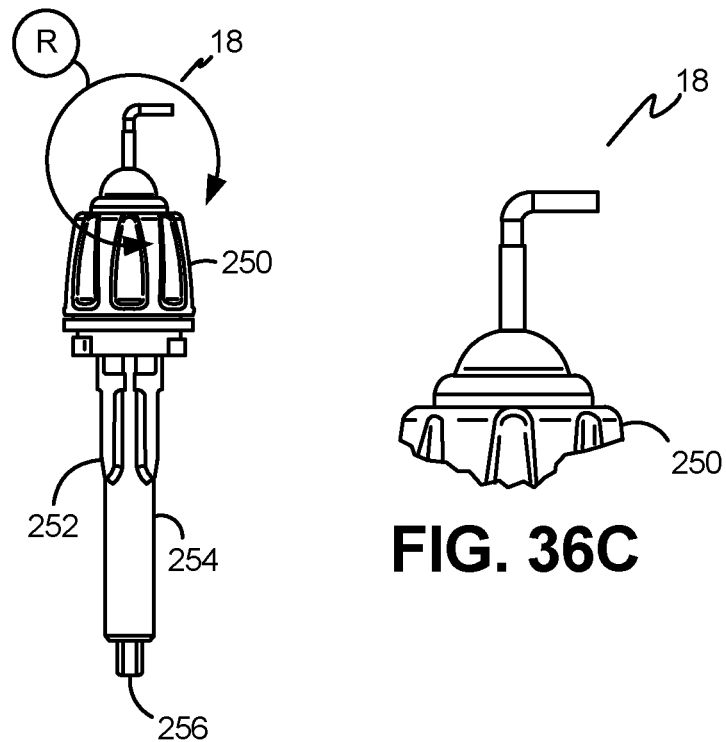
FIG. 36B
FIG. 36C

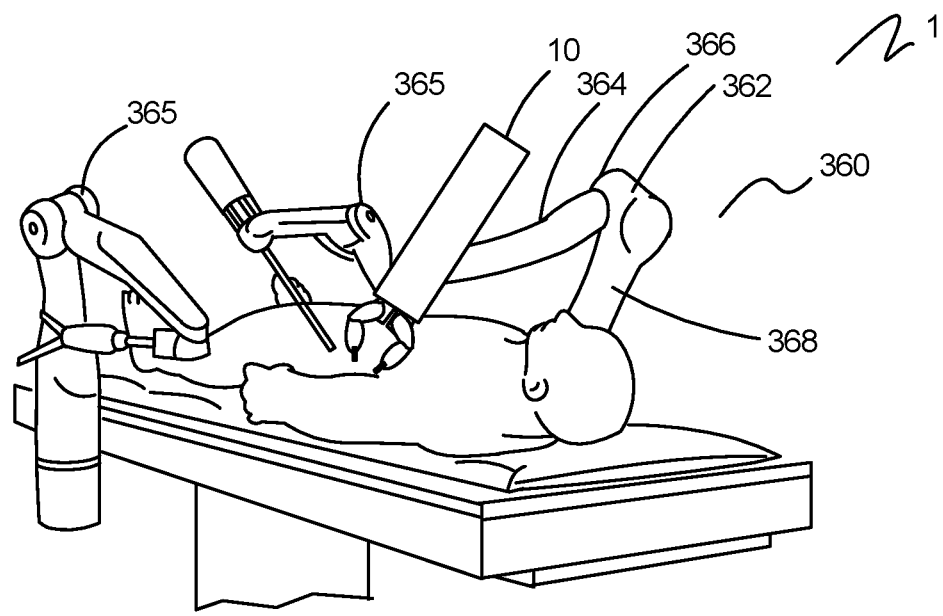
FIG. 45
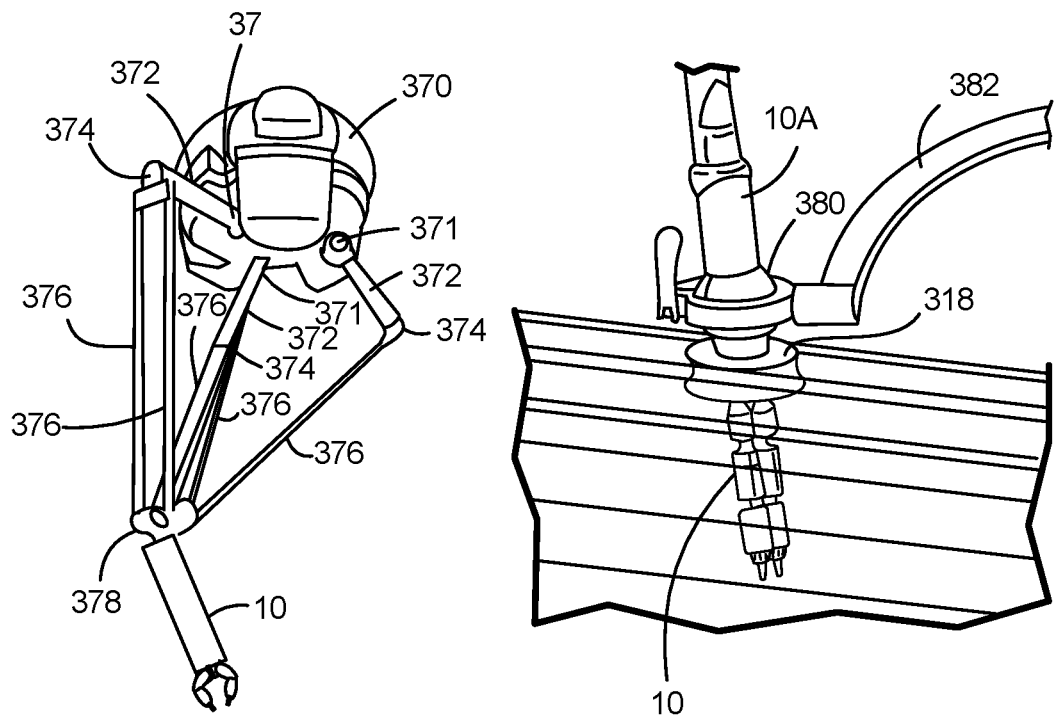
FIG. 46
FIG. 47

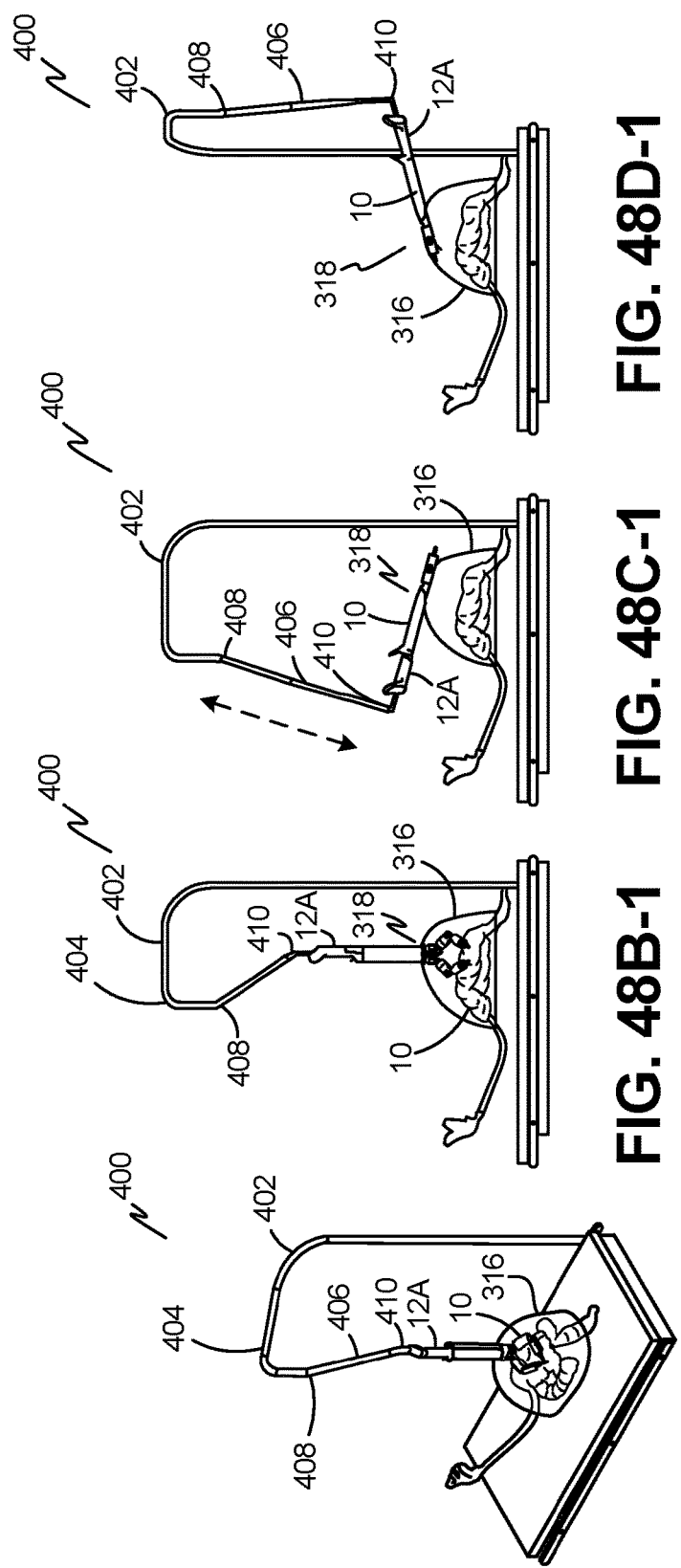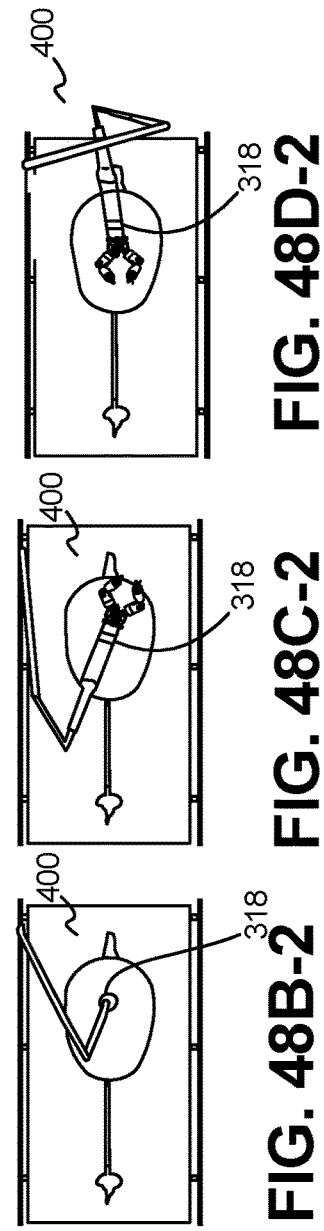

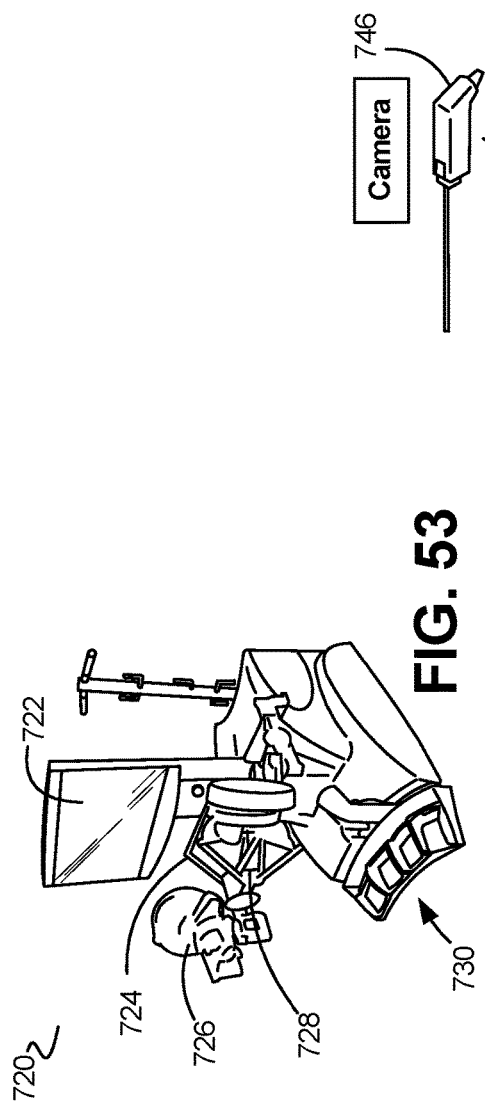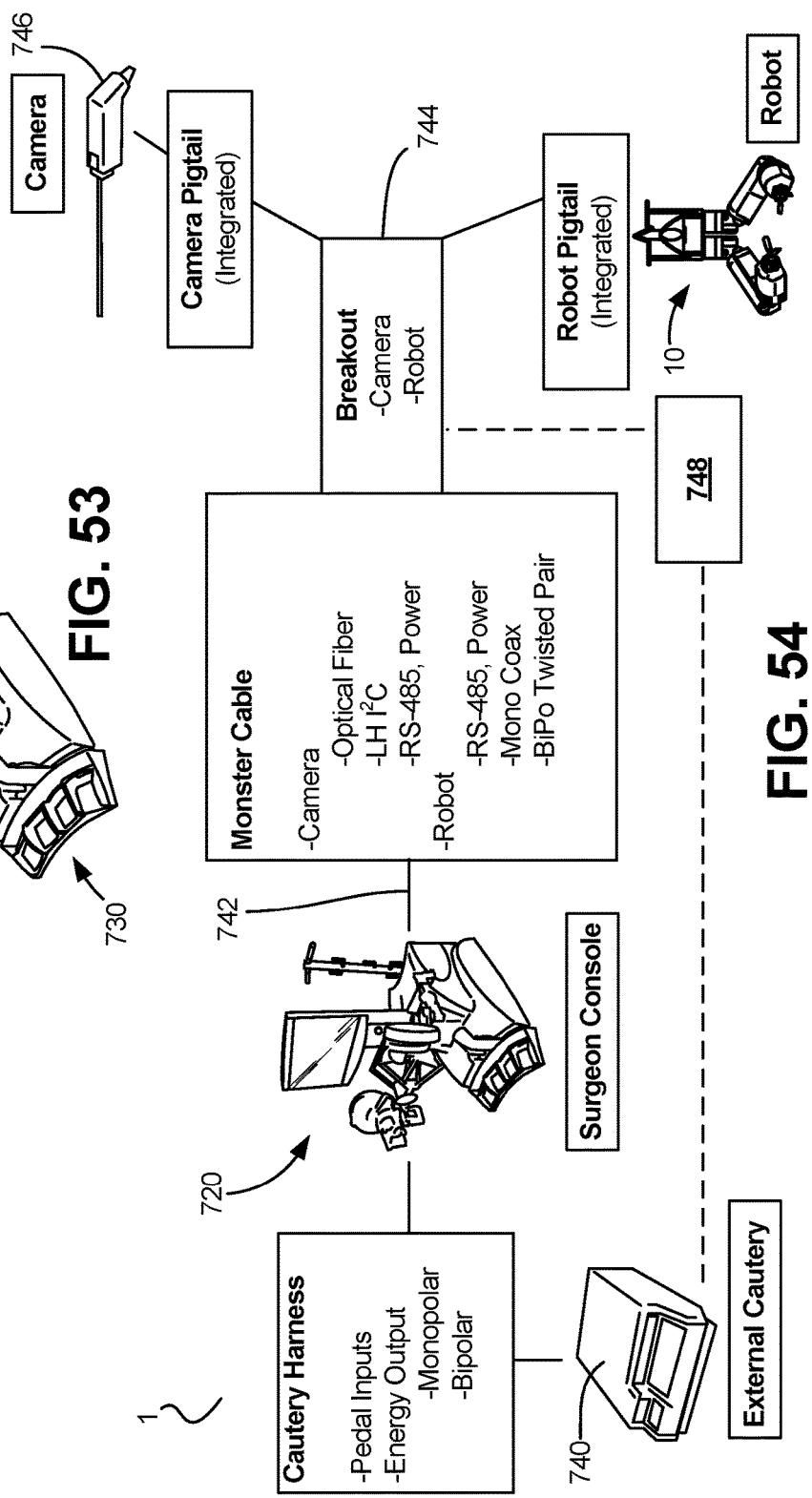
FIG. 53
FIG. 54

ROBOTIC SURGICAL DEVICES, SYSTEMS AND RELATED METHODS

CROSS-REFERENCE TO RELATED APPLICATION(S)

This application claims priority as a continuation of U.S. application Ser. No. 15/599,231, filed May 18, 2017, and entitled "Robotic Surgical Devices, Systems, and Related Methods," which claims the benefit under 35 U.S.C. § 119(e) to U.S. Provisional Application No. 62/338,375, filed on May 18, 2016 and entitled "Robotic Surgical Devices, Systems and Related Methods," both of which are hereby incorporated herein by reference in their entireties.

TECHNICAL FIELD

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Further embodiments relate to methods and devices for operating the above devices.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF SUMMARY OF THE INVENTION

Discussed herein are various robotic surgical systems, including certain systems having camera lumens configured to receive various camera systems. Further embodiments relate to surgical insertion devices configured to be used to insert various surgical devices into a cavity of a patient while maintaining insufflations of the cavity.

In one Example, a robotic surgical system, including: a robotic surgical device including: a device body including front and back sides and a distal end and a proximal end; first and second shoulder joints operably coupled to the distal end of the device body; a first robotic arm operably coupled to the first shoulder joint; and a second robotic arm operably coupled to the second shoulder joint; and a camera component, including a flexible section and a distal imager, where the first and second robotic arms are constructed and arranged so as to be positioned on the front or back sides of the body.

Implementations may include one or more of the following features. The robotic surgical system where the surgical device includes at least one actuator. The robotic surgical system where the first and second robotic arms include at least one motor disposed within each of the first and second robotic arms. The robotic surgical system further including a support device configured to remote center the robotic surgical device. The robotic surgical system further including an surgical console. The robotic surgical system where the camera is disposed through a lumen defined in the robotic surgical device. The robotic surgical system where the camera is configured to be an adjustable height camera. The robotic surgical system where the camera is constructed and arranged to be capable of pitch and yaw. The robotic surgical system where the distal camera tip is configured to orient to a define workspace. The robotic surgical system where the camera includes lights. The robotic surgical system where the robotic surgical device further includes first and second end effectors. The robotic surgical system where the first robotic arm further includes an upper arm and a forearm. The robotic surgical system where the first robotic arm further includes: a first arm upper arm; a first arm elbow joint; and a first arm lower arm, where the first arm upper arm is configured to be capable of roll, pitch and yaw relative to the first shoulder joint and the first arm lower arm is configured to be capable of yaw relative to the first arm upper arm by way of the first arm elbow joint. The surgical robotic system where the first robotic arm further includes at least one first arm actuator disposed within the first robotic arm. The robotic surgical system where the second robotic arm further includes: a second arm upper arm; \a second arm elbow joint; and a second arm lower arm, where the second arm upper arm is configured to be capable of roll, pitch and yaw relative to the second shoulder joint and the second arm lower arm is configured to be capable of yaw relative to the second arm upper arm by way of the second arm elbow joint. The surgical robotic system where the second robotic arm further includes at least one second arm actuator disposed within the second robotic arm. The surgical robotic system where the first and second arms include at least one motor disposed in each arm. The surgical robotic system further including at least one PCB disposed within at least one of the first or second robotic arms and in operational communication with at least one of the first robotic arm and second robotic arm, where the PCB is configured to perform yaw and pitch functions.

One Example includes A robotic surgical system, including: a robotic surgical device including: a device body including: a distal end; a proximal end; a front side; and a back side; first and second shoulder joints operably coupled to the distal end of the device body; a first robotic arm operably coupled to the first shoulder joint; and a second robotic arm operably coupled to the second shoulder joint; and a camera component, including: a shaft; an imager; and a flexible section operably coupling the imager to the shaft, where the first and second robotic arms are constructed and arranged so as to be positioned on the front or back sides of the body. Implementations may include one or more of the following features. The robotic surgical system where the first robotic arm further includes an upper arm and a forearm. The robotic surgical system where the first robotic arm further includes: a first arm upper arm; a first arm elbow joint; and a first arm lower arm, where the first arm upper arm is configured to be capable of roll, pitch and yaw relative to the first shoulder joint and the first arm lower arm is configured to be capable of yaw relative to the first arm upper arm by way of the first arm elbow joint. The surgical robotic system where the first robotic arm further includes at least one first arm actuator disposed within the first robotic arm. The robotic surgical system where the second robotic arm further includes: a second arm upper arm; a second arm elbow joint; and a second arm lower arm, where the second arm upper arm is configured to be capable of roll, pitch and yaw relative to the second shoulder joint and the second arm lower arm is configured to be capable of yaw relative to the second arm upper arm by way of the second arm elbow joint. The surgical robotic system where the second robotic arm further includes at least one second arm actuator disposed within the second robotic arm. The surgical robotic system where the first and second arms include at least one motor disposed in each arm. The surgical robotic system further including at least one PCB disposed within at least one of the first or second robotic arms and in operational communication with at least one of the first robotic arm and second robotic arm, where the PCB is configured to perform yaw and pitch functions. Implementations of the described techniques may include hardware, a method or process, or computer software on a computer-accessible medium.

Another Example includes A robotic surgical system, including: a robotic surgical device including: a device body including: a distal end; a proximal end, and a camera lumen defined within the device body, the camera lumen including: a proximal lumen opening in the proximal end of the device body; a socket portion defined distally of the proximal lumen opening, the socket portion including a first diameter and a first coupling component; an extended portion defined distally of the socket portion, the extended portion having a second, smaller diameter; and a distal lumen opening in the distal end of the device body, the distal lumen opening defined at a distal end of the extended portion; first and second shoulder joints operably coupled to the distal end of the device body; a first robotic arm operably coupled to the first shoulder joint; and a second robotic arm operably coupled to the second shoulder joint; and a camera component, including an elongate tube operably coupled to the handle, where the elongate tube is configured and sized to be positionable through the extended portion, the elongate tube including: a shaft; an imager; and a flexible section operably coupling the optical section to the rigid section, where the elongate tube has a length such that at least the optical section is configured to extend distally from the distal lumen opening when the camera component is positioned through the camera lumen.

Implementations may include one or more of the following features. The surgical robotic system where the first and second arms include at least one motor disposed in each arm. The surgical robotic system further including at least one PCB disposed within at least one of the first or second robotic arms and in operational communication with at least one of the first robotic arm and second robotic arm, where the PCB is configured to perform yaw and pitch functions.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 28C is a front view of a robotic device and camera having adjustable depth, according to one embodiment.

FIG. 28D is a close up view of the device lumen and camera shaft showing the adjustable depth mechanism, according to one implementation, showing the camera in an "up" position.

FIG. 28E is a front view of the robot and camera, according to the implementations of FIGS. 28C and 28D.

FIG. 28F is a front view of a robotic device and camera having adjustable depth, according to one embodiment.

FIG. 28G is a close up view of the device lumen and camera shaft showing the adjustable depth mechanism, according to one implementation, showing the camera in an "down" position.

FIG. 28H is a front view of the robot and camera, according to the implementations of FIGS. 28F and 28G.

FIG. 30A depicts a surgical device and zero-degree camera in one of a range of possible positions, according to one implementation.

FIG. 30B depicts a surgical device and zero-degree camera in one of a range of possible positions, according to one implementation.

FIG. 30C depicts a surgical device and zero-degree camera in one of a range of possible positions, according to one implementation.

FIG. 30D depicts a surgical device and zero-degree camera in one of a range of possible positions, according to one implementation.

FIG. 30E depicts a surgical device and zero-degree camera in one of a range of possible positions, according to one implementation.

FIG. 30F depicts a surgical device and zero-degree camera in one of a range of possible positions, according to one implementation.

FIG. 31A depicts a surgical device and zero-degree camera in one of a range of possible positions, according to another implementation.

FIG. 31B depicts a surgical device and zero-degree camera in one of a range of possible positions, according to another implementation.

FIG. 31C depicts a surgical device and zero-degree camera in one of a range of possible positions, according to another implementation.

FIG. 31D depicts a surgical device and zero-degree camera in one of a range of possible positions, according to another implementation.

FIG. 31E depicts a surgical device and zero-degree camera in one of a range of possible positions, according to another implementation.

FIG. 31F depicts a surgical device and zero-degree camera in one of a range of possible positions, according to another implementation.

FIG. 32A depicts a surgical device and zero-degree camera in one of a range of possible positions, according to another implementation.

FIG. 32B depicts a surgical device and zero-degree camera in one of a range of possible positions, according to another implementation.

FIG. 32C depicts a surgical device and zero-degree camera in one of a range of possible positions, according to another implementation.

FIG. 32D depicts a surgical device and zero-degree camera in one of a range of possible positions, according to another implementation.

FIG. 32E depicts a surgical device and zero-degree camera in one of a range of possible positions, according to another implementation.

FIG. 32F depicts a surgical device and zero-degree camera in one of a range of possible positions, according to another implementation.

FIG. 33A depicts a surgical device and camera in a first viewing position with an "S-scope" configuration, according to one implementation.

FIG. 33B depicts a surgical device and camera in a second viewing position with an "S-scope" configuration, according to one implementation.

FIG. 33C depicts a surgical device and camera in a first viewing position with an "S-scope" configuration, according to one implementation.

FIG. 35A is a side view of the surgical device and camera showing the camera between at a first depth, according to one embodiment.

FIG. 35B is a side view of the surgical device and camera showing the camera between at a second depth, according to one embodiment.

FIG. 35C is a side view of the surgical device and camera showing the camera between at a third depth, according to one embodiment.

FIG. 36A is a side view of a surgical device end effector, according to one embodiment.

FIG. 36B is a side view of a surgical device end effector, according to another embodiment.

FIG. 36C is a side view of a surgical device end effector, according to another embodiment.

FIG. 41A is a perspective view of the surgical device on a support structure, according to one implementation.

FIG. 45 is a perspective view of the surgical device on a support robot, according to another implementation.

FIG. 46 is a perspective view of the surgical device on a support robot, according to another implementation.

FIG. 47 is a perspective view of the surgical device on a ball joint support structure, according to another implementation.

FIG. 48A is a perspective view of a support structure for positioning the surgical device, according to one implementation.

FIG. 48B-1 is a side view of the support device according to the embodiment of FIG. 48 in a first position.

FIG. 48B-2 is a top view of the implementation of the support device of FIG. 48B-1.

FIG. 48C-1 is a side view of the support device according to the embodiment of FIG. 48 in a second position.

FIG. 48C-2 is a top view of the implementation of the support device of FIG. 48C-1.

FIG. 48D-1 is a side view of the support device according to the embodiment of FIG. 48 in a third position.

FIG. 48D-2 is a top view of the implementation of the support device of FIG. 48D-1.

FIG. 53 is a perspective view of the surgical console, according to one implementation.

FIG. 54 is a schematic view of a surgical system, according to one implementation.

DETAILED DESCRIPTION

Figure 1A:
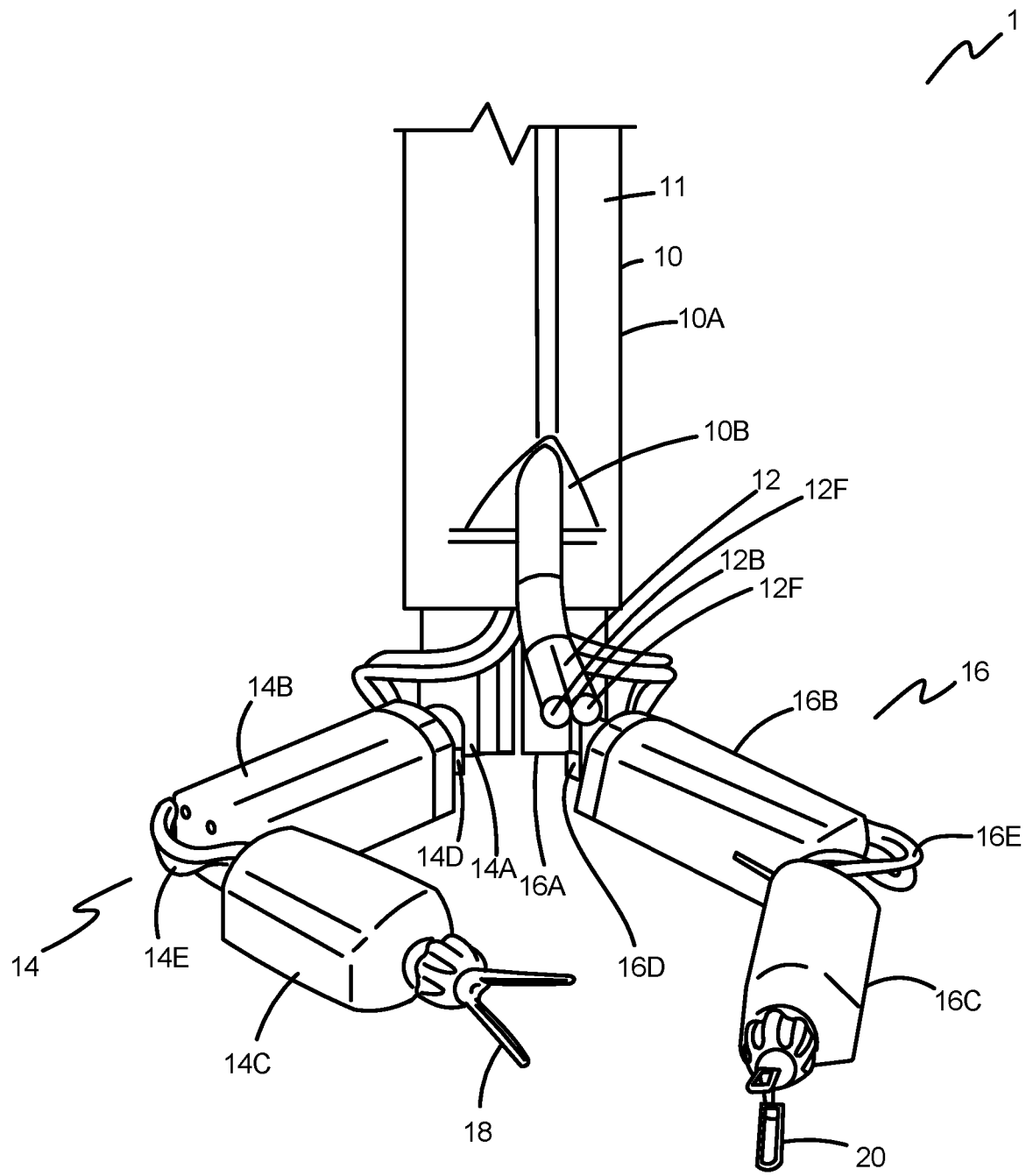
FIG. 1A is a front view of a surgical device, according to one embodiment.

The various systems and devices disclosed herein relate to devices for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in copending U.S. application Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), 61/030,588 (filed on Feb. 22, 2008), Ser. No. 12/171,413 (filed on Jul. 11, 2008 and entitled "Methods and Systems of Actuation in Robotic Devices"), Ser. No. 12/192,663 (filed Aug. 15, 2008 and entitled "Medical Inflation, Attachment, and Delivery Devices and Related Methods"), Ser. No. 12/192,779 (filed on Aug. 15, 2008 and entitled "Modular and Cooperative Medical Devices and Related Systems and Methods"), Ser. No. 12/324,364 (filed Nov. 26, 2008 and entitled "Multifunctional Operational Component for Robotic Devices"), 61/640,879 (filed on May 1, 2012), Ser. No. 13/493,725 (filed Jun. 11, 2012 and entitled "Methods, Systems, and Devices Relating to Surgical End Effectors"), Ser. No. 13/546,831 (filed Jul. 11, 2012 and entitled "Robotic Surgical Devices, Systems, and Related Methods"), 61/680,809 (filed Aug. 8, 2012), Ser. No. 13/573,849 (filed Oct. 9, 2012 and entitled "Robotic Surgical Devices, Systems, and Related Methods"), Ser. No. 13/738,706 (filed Jan. 10, 2013 and entitled "Methods, Systems, and Devices for Surgical Access and Insertion"), Ser. No. 13/833,605 (filed Mar. 15, 2013 and entitled "Robotic Surgical Devices, Systems, and Related Methods"), Ser. No. 13/839,422 (filed Mar. 15, 2013 and entitled "Single Site Robotic Devices and Related Systems and Methods"), Ser. No. 13/834,792 (filed Mar. 15, 2013 and entitled "Local Control Robotic Surgical Devices and Related Methods"), Ser. No. 14/208,515 (filed Mar. 13, 2014 and entitled "Methods, Systems, and Devices Relating to Robotic Surgical Devices, End Effectors, and Controllers"), Ser. No. 14/210,934 (filed Mar. 14, 2014 and entitled "Methods, Systems, and Devices Relating to Force Control Surgical Systems), Ser. No. 14/212,686 (filed Mar. 14, 2014 and entitled "Robotic Surgical Devices, Systems, and Related Methods"), and Ser. No. 14/334,383 (filed Jul. 17, 2014 and entitled "Robotic Surgical Devices, Systems, and Related Methods"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), U.S. Published Application No. 2016/0074120 (filed Sep. 14, 2015, and entitled "Quick-Release End Effectors and Related Systems and Methods"), U.S. Published Application No. 2016/0135898 (filed Nov. 11, 2015 entitled "Robotic Device with Compact Joint Design and Related Systems and Methods"), U.S. patent application Ser. No. 15/227,813 (filed Aug. 3, 2016 and entitled "Robotic Surgical Devices, Systems, and Related Methods"), U.S. Provisional Application No. 62/379,344 (filed Aug. 25, 2016 and entitled "Quick-Release End Effector Tool Interface and Related Systems and Methods"), U.S. Provisional Application No. 62/425,149 (filed Nov. 22, 2016 and entitled "Improved Gross Positioning Device and Related Systems and Methods"), U.S. Provisional Application No. 62/427, 357 (filed Nov. 29, 2016 and entitled "Controller with User Presence Detection and Related Systems and Methods"), U.S. Provisional Application No. 62/433,837 (filed Dec. 14, 2016 and entitled "Releasable Attachment Device for Coupling to Medical Devices and Related Systems and Methods"), and U.S. Provisional Application No. 62/381,299 (filed Aug. 30, 2016 and entitled "Robotic Device with Compact Joint Design and an Additional Degree of Freedom and Related Systems and Methods") a all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

Certain embodiments disclosed or contemplated herein can be used for colon resection, a surgical procedure performed to treat patients with lower gastrointestinal diseases such as diverticulitis, Crohn's disease, inflammatory bowel disease and colon cancer. Approximately two-thirds of known colon resection procedures are performed via a completely open surgical procedure involving an 8- to 12-inch incision and up to six weeks of recovery time. Because of the complicated nature of the procedure, existing robot-assisted surgical devices are rarely used for colon resection surgeries, and manual laparoscopic approaches are only used in one-third of cases. In contrast, the various implementations disclosed herein can be used in a minimally invasive approach to a variety of procedures that are typically performed 'open' by known technologies, with the potential to improve clinical outcomes and health care costs. Further, the various implementations disclosed herein can be used in place of the known mainframe-like laparoscopic surgical robots that reach into the body from outside the patient. That is the less-invasive robotic systems, methods, and devices disclosed herein feature small, self-contained surgical devices that are inserted in their entireties through a single incision in the patient's abdomen. Designed to utilize existing tools and techniques familiar to surgeons, the devices disclosed herein will not require a dedicated operating room or specialized infrastructure, and, because of their much smaller size, are expected to be significantly less expensive than existing robotic alternatives for laparoscopic surgery. Due to these technological advances, the various embodiments herein could enable a minimally invasive approach to procedures performed in open surgery today.

The various embodiments are disclosed in additional detail in the attached figures, which include some written description therein.

The various system embodiments described herein are used to perform robotic surgery. The systems are used for general surgery applications in the abdominal cavity, including colon resection. In certain implementations, the various systems described herein are based on and/or utilize techniques used in manual laparoscopic surgery including insufflation of the abdominal cavity and the use of ports to insert tools into the abdominal cavity.

Major components of the various system embodiments include a robot and a surgeon control console. The robot implementations are configured to be inserted into the insufflated abdominal cavity. Certain robot embodiments have an integrated camera system that captures a view of the surgical target. The surgeon can then use that view on a display to help control the robot's movements. In certain implementations, the camera is designed so that it can be removed so it can be cleaned and used in other applications.

The surgeon console, according to some embodiments, has a display to view the feedback from the camera. This display can also have overlays to provide some additional information to the surgeon including the robot's state and other information. The console can also have a touch screen used to control various system functions. In addition, the various console embodiments can also have user input devices (e.g. haptic joysticks) that the surgeon can use to control the movement of the robot's arms and other movement. Further, the console can also has one or more pedals used to control various robot control and functions.

In other embodiments as will be discussed in further detail herein, the system can include disposable or permanent sleeves, an electro-surgery cautery generator, an insertion port, a support arm/structure, a camera, remote surgical displays, end-effectors (tools), an interface pod, a light source, and other support components.

Figure 1B:
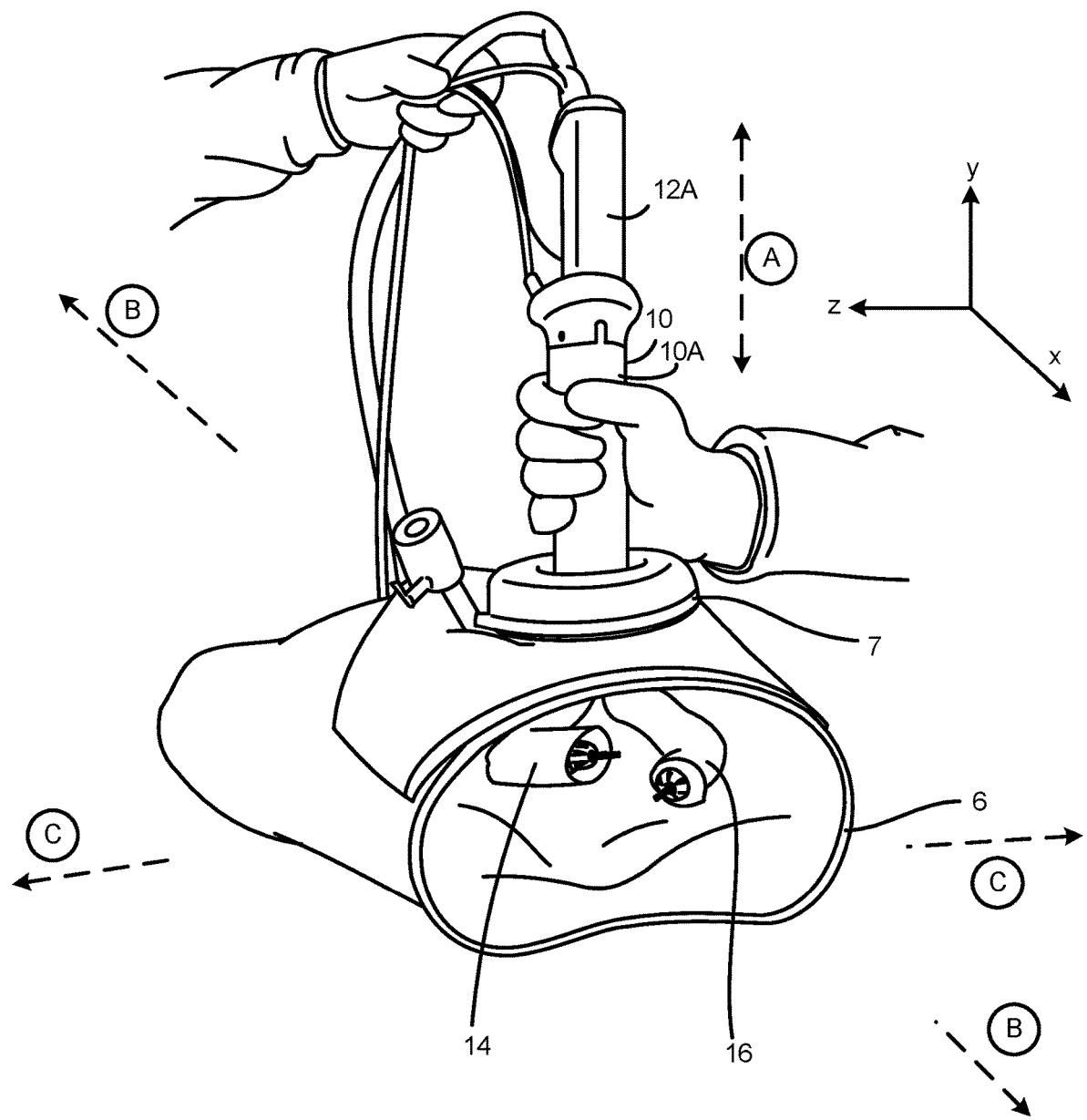
FIG. 1B is a front view of the device of FIG. 1A inserted into the body cavity.

FIGS. 1A and 1B depict one embodiment of the system 1 with a robot or robotic device 10 with a camera 12. As shown in FIG. 1A, the robotic device 10 has two robotic arms 14, 16 operably coupled thereto and a camera component or "camera" 12 disposed between the two arms 14, 16 and positionable therein. That is, device 10 has a first (or "right") arm 14 and a second (or "left") arm 16, both of which are operably coupled to the device 10 as discussed in additional detail below. The device 10 as shown has a casing (also referred to as a "cover" or "enclosure") 11. The device 10 is also referred to as a "device body" 10A and has two rotatable cylindrical components (also referred to as "shoulders" or "turrets"): a first (or "right") shoulder 14A and a second (or "left") shoulder 16A. Each arm 14, 16 also has an upper arm (also referred to herein as an "inner arm," "inner arm assembly," "inner link," "inner link assembly," "upper arm assembly," "first link," or "first link assembly") 14B, 16B, and a forearm (also referred to herein as an "outer arm," "outer arm assembly," "outer link," "outer link assembly," "forearm assembly," "second link," or "second link assembly") 14C, 16C. The right upper arm 14B is operably coupled to the right shoulder 14A of the body 10A at the right shoulder joint 14D and the left upper arm 16B is operably coupled to the left shoulder 16A of the body 10 at the left shoulder joint 16D. Further, for each arm 14, 16, the forearm 14C, 16C is rotatably coupled to the upper arm 14B, 16B at the elbow joint 14E, 16E.

As shown in FIG. 1B, the robotic device 10 has been inserted into a model of the abdominal cavity 6 through a gel port 7 in a fashion similar to the way it would be inserted into a patient's abdominal cavity 6. The gel port 7 allows for an irregularly shaped robotic device 10 to be inserted while maintaining insufflation pressure. In this implementation, a standard manual laparoscopic port 7 is used in addition to the robot 10. Alternatively, two or more such ports can be utilized (not shown). In a further alternative, no standard manual laparoscopic ports are used.

In FIG. 1B, the device body 10A is shown having been inserted in a ventral-dorsal orientation into the abdominal cavity such that the longitudinal body axis (as is shown by reference arrow A) is generally perpendicular relative to the rostrocaudal/anteroposterior and mediolateral axes (reference arrows B and C, respectively). It is understood that following insertion, the device body 10A can be variously positioned, so as to be rotated, tilted or angled relative to the cavity 6 to alter the device workspace and access various regions of the cavity, as is described in detail below in relation to FIGS. 6A-8C.

Figure 2:
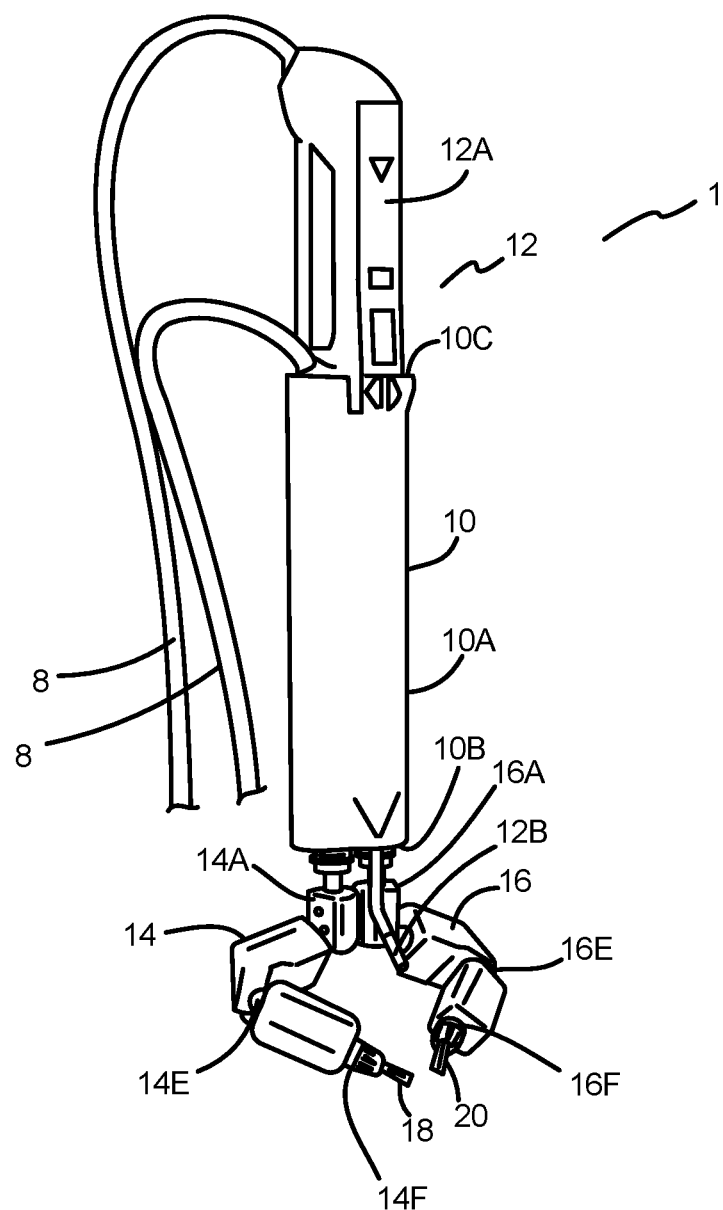
FIG. 2 is a front view of a surgical device, according to one embodiment.

FIG. 2 shows the robot with the integrated camera system, according to one embodiment. The robot of FIG. 2 has two arms 14, 16 and a body 10A (or torso) having a distal end 10B and proximal end 10C. The arms 14, 16 each have active degrees of freedom and an additional active joint 14F, 16F to actuate the end effectors, or tools 18, 20. It is understood that more or less degrees of freedom could be included. The device in this embodiment has a connection line 8 (also referred to as a "pigtail cable") (partially shown) that includes electrical power, electrocautery, and information/communication signals. In certain implementations, the device has distributed control electronics and software to help control the device 10. Some buttons can be included to support insertion and extraction of the device into and out of the abdominal cavity. In this embodiment, the integrated camera 12 is also shown inserted in the device body 10A. When inserted into the body 10A, the camera 12 has a handle or body 12A that extends proximally from the proximal body end 10C and a flexible camera imager 12B extending from the distal body end 10B.

Figure 3:
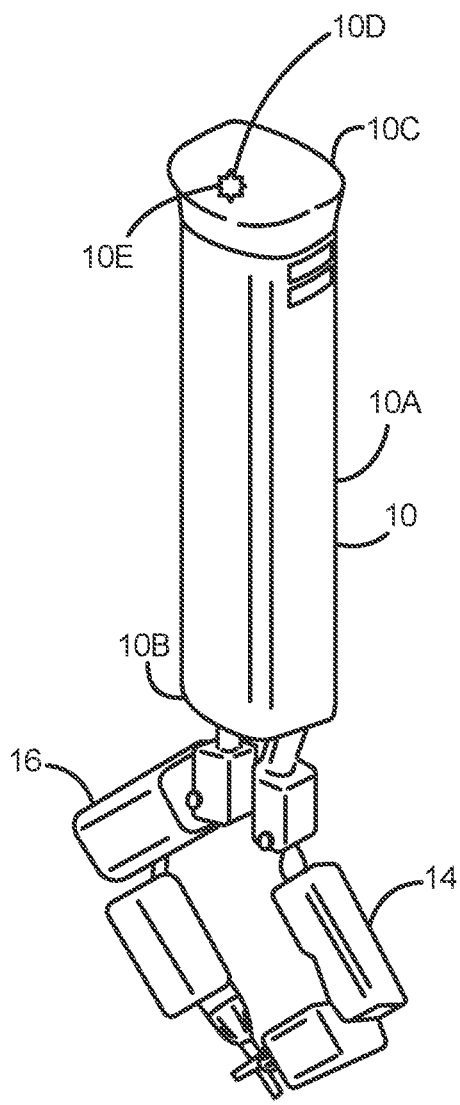
FIG. 3 is a three-quarters perspective view of the robot of the implementation of FIG. 2 without the camera.
Figure 4:
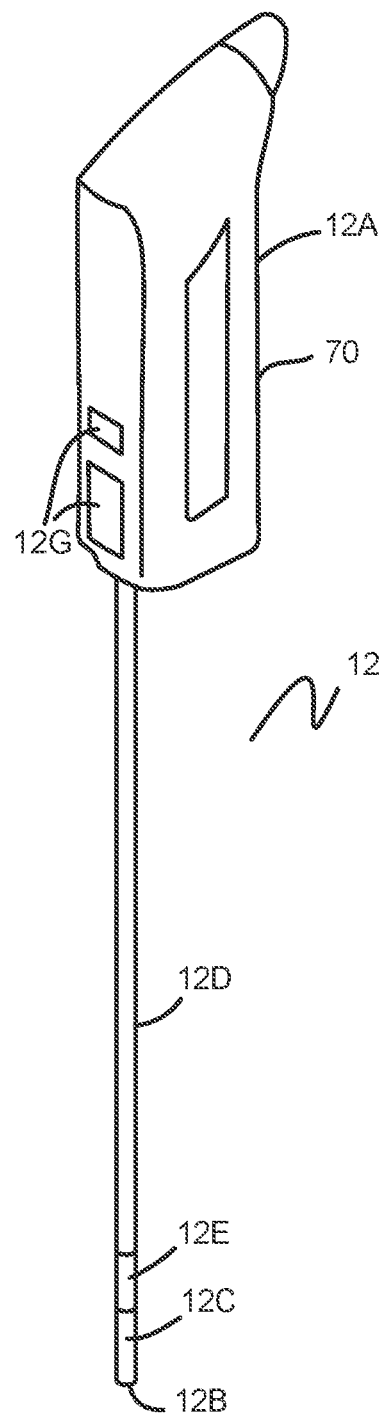
FIG. 4 is a three-quarters perspective view of the camera of the implementation of FIG. 2 without the robot.

FIGS. 3 and 4 depict the robotic device 10 with the camera assembly 12 removed, according to one embodiment. In these embodiments, and as shown in FIG. 2 and FIGS. 3-4, the camera imager 12B is designed to be positioned between the two arms 14, 16 and capture that view between the two arms 14, 16. In these implementations, the camera 12 extends through the robot body 10A such that the camera imager 12B exits near the joints between the body and the robotic arms (the "shoulder" joints 14A, 16A). The camera 12 has a flexible, steerable tip 12C to allow the user to adjust the viewing direction. The end effectors 18, 20 on the distal end of the arms 14, 16 can include various tools 18, 20 (scissors, graspers, needle drivers, etc). In certain embodiments, the tools 18, 20 are designed to be removable by a small twist of the tool knob that couples the end effector to the arm 14, 16.

As is shown in FIGS. 3-4, the camera assembly 12 has a handle 12A and a long shaft 12D with the camera imager 12B at the distal tip 12C. In various implementations, the flexible tip 12C and therefore camera imager 12B can be steered or otherwise moved in two independent directions in relation to the shaft 12D at a flexible section 12E (black section on shaft) to change the direction of view. In certain implementations, the camera 12 has some control buttons 12G as shown. In some embodiments, the camera assembly 12 can be used independently of the robotic device 10 as shown in FIG. 4.

Alternatively, the assembly can be inserted into the robot 10 though a lumen 10D defined through the body 10A of the robotic device 10 as shown. In certain embodiments, the lumen 10D includes a seal/port 10E to ensure that the patient's cavity remains insufflated (as shown in relation to FIG. 1B). According to one embodiment, the robotic device 10 can have a sensor to determine if the camera is positioned in the camera lumen 10D of the device 10.

FIG. 5 depicts a robotic device 10 according to one embodiment in a configuration in which the positionable arms 14, 16 are positioned such that the tools 18, 20 are positioned in line with the camera tip 12C. That is, in this embodiment the arms 14, 16 are disposed in the workspace so as to be within the field of view of the camera imager 12B (designated by reference lines "V$_1$" and "V$_2$"). In the implementation of FIG. 5, the device 10 is positioned within the cavity of the patient at an angle—that is, such that the longitudinal axis of the device body 10A (designated by reference line A) is not perpendicular to the body of the patient (as shown, for example, in FIG. 1B).

Figure 5A:
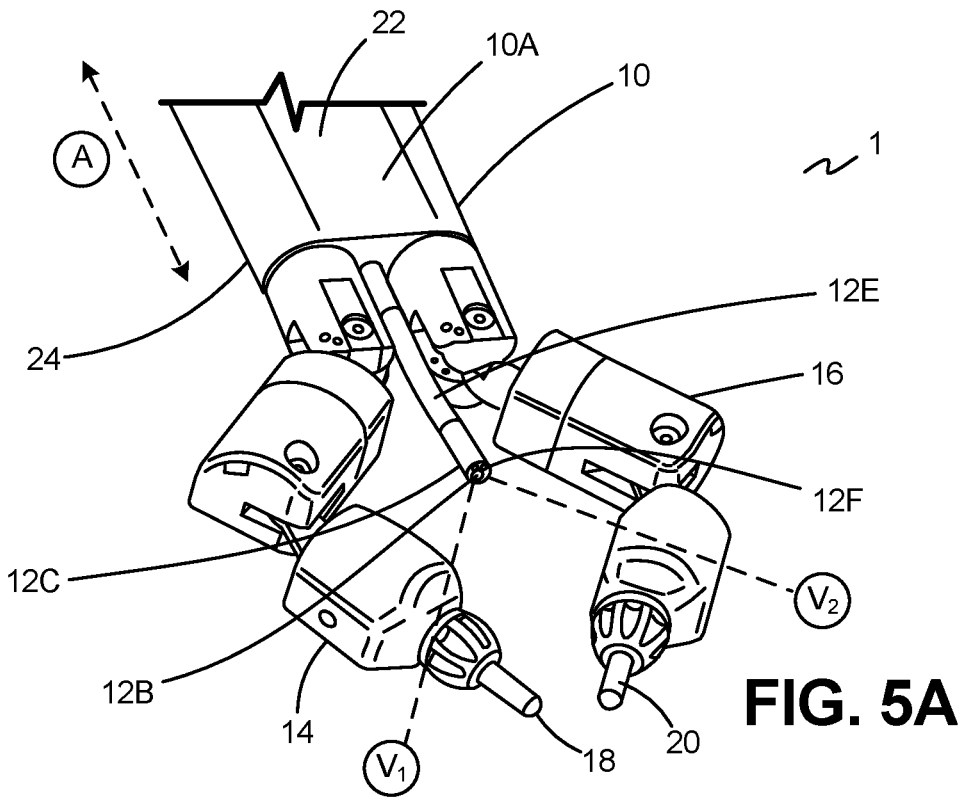
FIG. 5A is a close-up perspective view of a surgical device, according to one embodiment.

In the implementation of FIG. 5A, the device body 10A is therefore oriented so as to have a "top," "upper," or "front" side 22 and a "bottom," "lower," or "back" side 24. It is understood that further configurations are possible, and as described in detail herein, the camera 12 and arms 14, 16 are capable of extending into either side 22, 24 so as to provide large workspaces without the need to rotate the device body 10A.

Figure 5B:
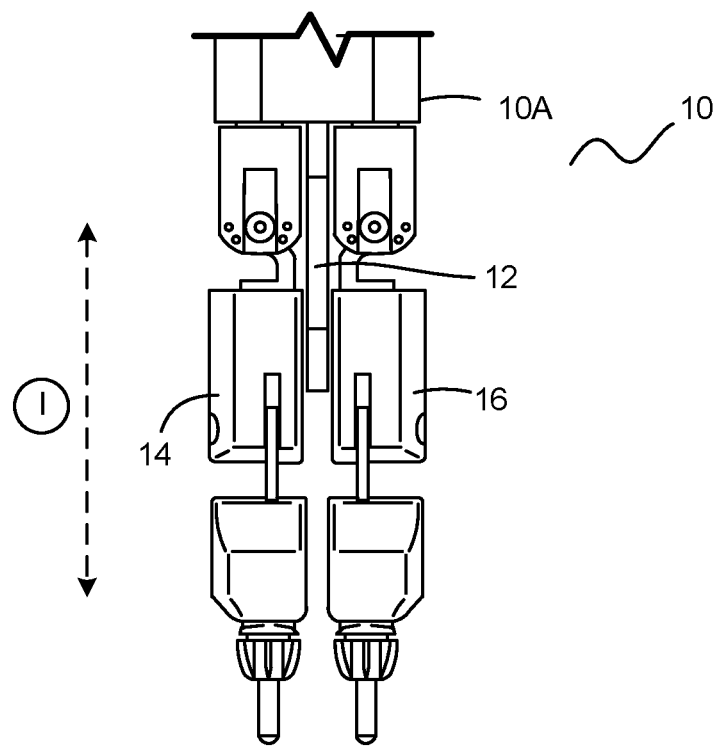
FIG. 5B is front view of the embodiment of FIG. 5A, wherein the arms and camera are in the "insertion" position.

In the implementation shown in FIG. 5B, the arms 14, 16 of the robotic device 10 are positioned in an "insertion" configuration. As shown, in the insertion configuration, the arms 14, 16 and camera 12 are all primarily aligned with the robotic device body 10A such that the longitudinal axes of each of the components are substantially parallel to one another (as shown by reference arrow I) for insertion through the port (as is shown, for example, in FIG. 1B at 7). It is understood that the insertion configuration minimizes the overall "footprint" of the device 10, so as to allow the smallest possible incision. In certain implementations, during insertion the device 10 can be passed through a variety of positions while being inserted, as has been previously described in U.S. patent application Ser. No. 15/227,813 filed Aug. 3, 2016 and entitled "Robotic Surgical Devices, Systems, and Related Methods," which is incorporated by reference herein in its entirety.

A principle advantage of the system 1 in certain implementations is a wide workspace range for the arms, including embodiments wherein the arms are positioned "behind" the device. In use, increasing the workspace range of each of the arms can reduce the need to reposition to the device, and therefore lead to greater efficiency and faster total surgery times and recovery. Several implementations showing the increased arm range are described herein.

FIGS. 6A, 6B, 7A, 7B, and 7C schematically depict the entire workspace 30 as well as the individual reachable workspaces 30A, 30B of each of the arms 14, 16 of a robotic device 10, according to certain embodiments. In these embodiments, "workspace" 30 means the space 30 around the robotic device 10 in which either arm and/or end effector 18, 20 can move, access, and perform its function within that space.

Figure 6A:
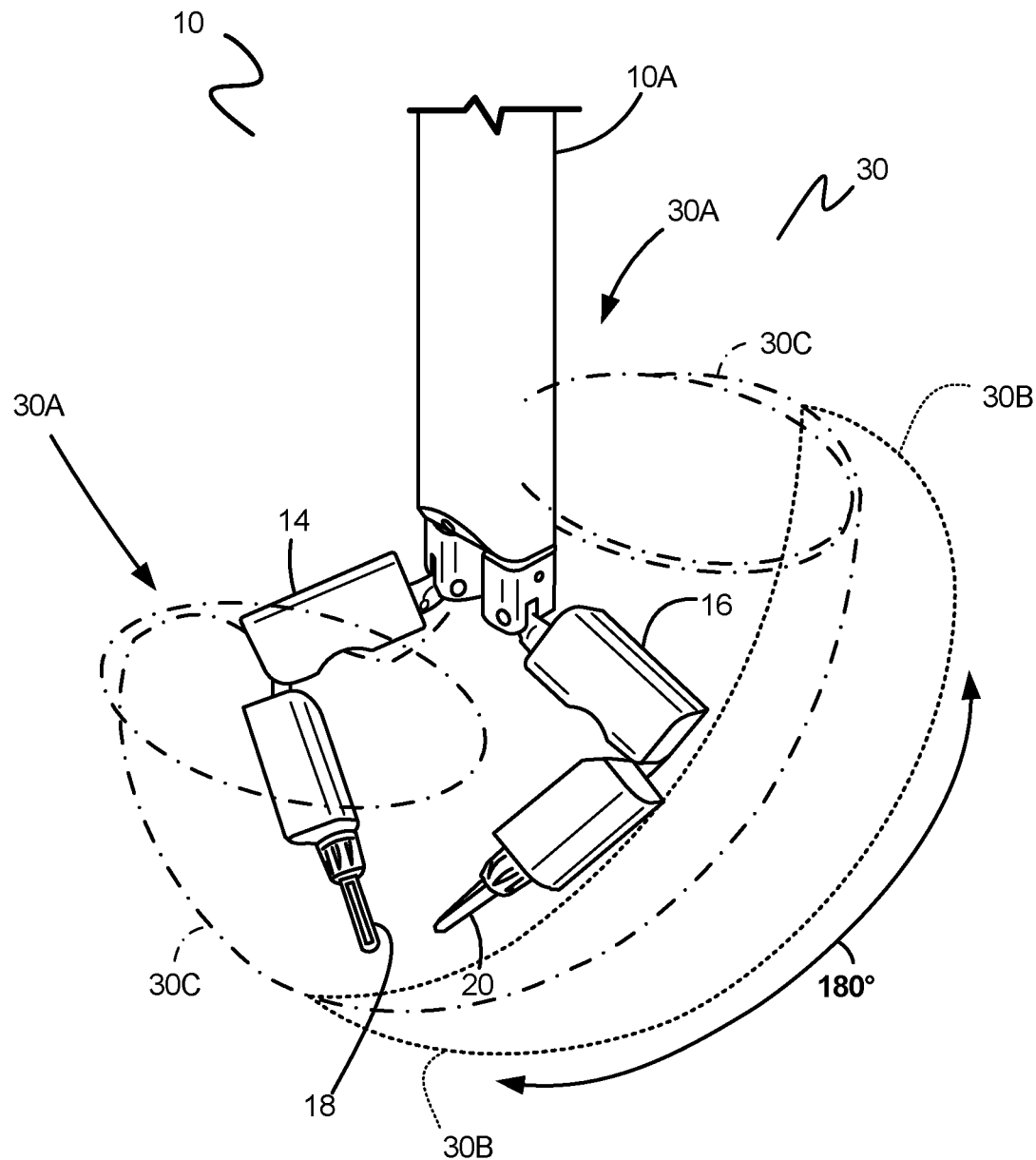
FIG. 6A is a perspective view of a surgical device showing various workspaces for the arms, according to one embodiment.

More specifically, FIG. 6A depicts a perspective view of the device body 10A and further schematically shows the entire workspace 30 as well as the individual workspaces 30A, 30B of the first arm 14 and second arm 16, respectively. Note that the each arm 14, 16 has a range of motion and corresponding workspace 30A, 30B that extends from the front 22 of the device to the back 24 of the device 10. Thus, the first arm 14 equally to the front 22 and the back 24, through about 180° of space relative to the axis of the device body 10A for each arm 14, 16. This workspace 30 allows the robotic device to work to the front 22 and back 24 equally well without having to reposition the body 10A.

Figure 6B:
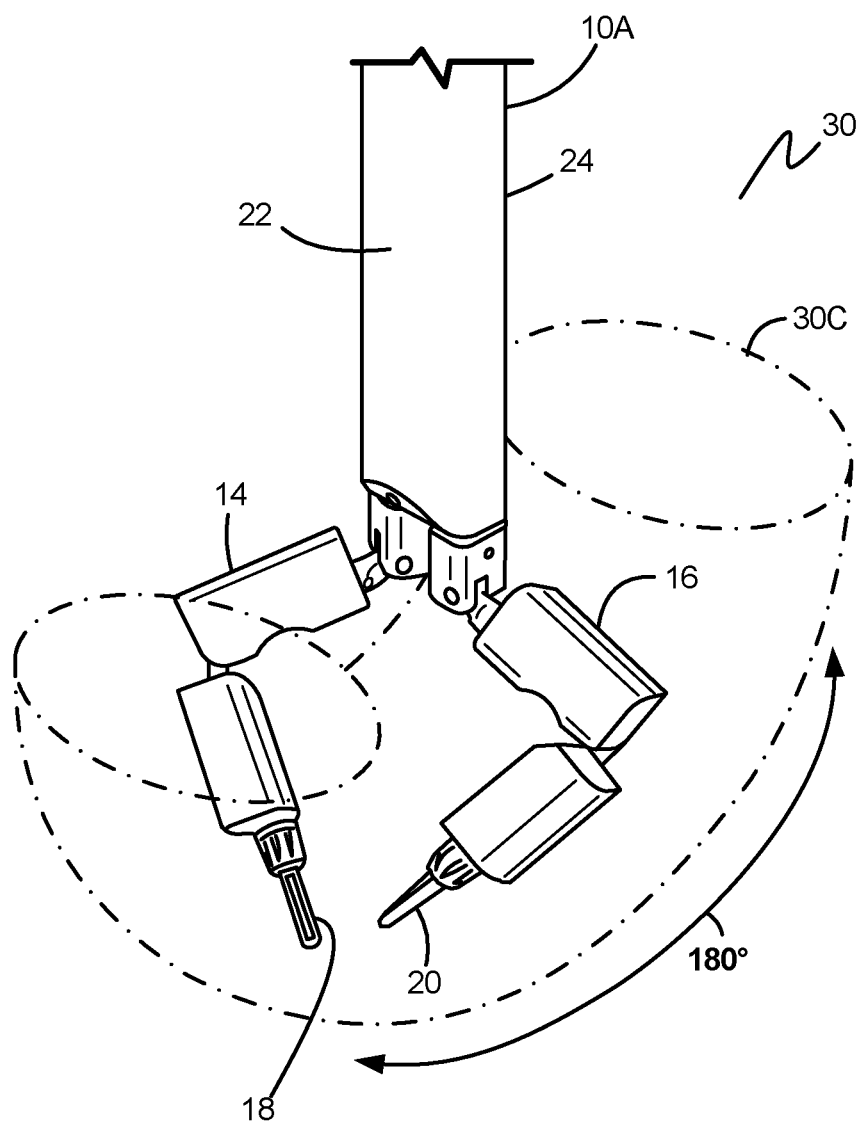
FIG. 6B is a further perspective view of the surgical device of FIG. 6A, showing the workspace of one arm.

As best shown in FIG. 6B, the overlap of the ranges of motion for the individual arms in these implementations also enables an intersecting workspace 30C (as is also shown in FIG. 6A). It is understood that the intersecting workspace 30C in these implementations encompasses the workspace 30C reachable by both arms 14, 16 and end effectors 18, 20 in any individual device 10 position. Again, in these implementations, the intersecting workspace 30C includes a range of about 180° of space relative to the axis of the device body 10A.

Figure 7A:
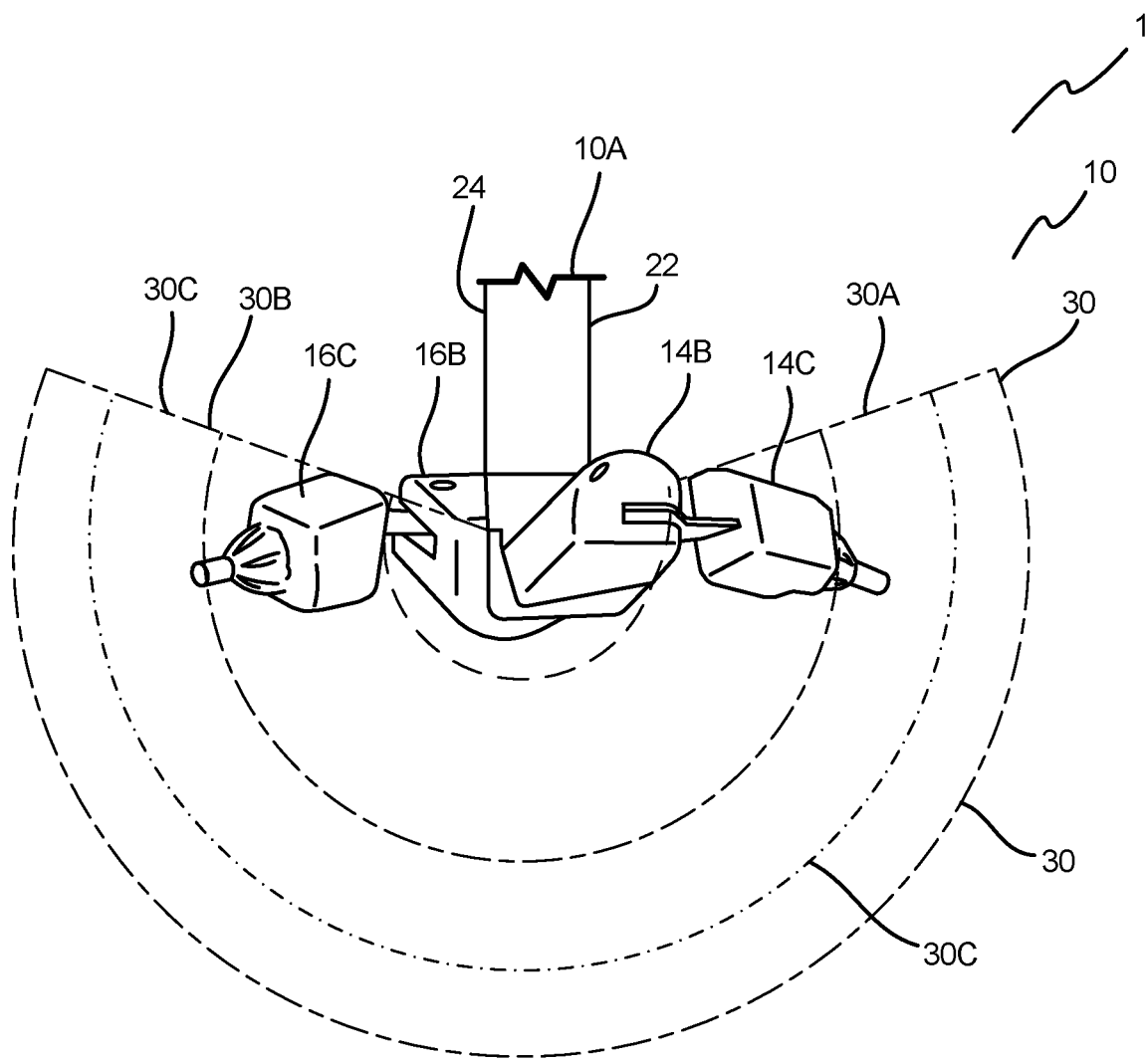
FIG. 7A is a side view of the robot according to one embodiment, showing the range of motion of the arms and the associated workspaces, according to one embodiment.

FIG. 7A depicts a side view of the device body 10A and further schematically shows the workspace 30A of the first arm 14. Note that the first arm 14 has a range of motion that extends from the front 22 of the device to the back 24 of the device 10. Thus, the first arm 14 equally to the front 22 and the back 24. This allows the robotic device to work to the front 22 and back 24 equally well without having to reposition the body 10A. With respect to the actual position of the arms 14, 16, FIG. 7A depicts the first arm 14 extending out from the front 22 of the device while the second arm 16 is extending out from the back 24.

Figure 7B:
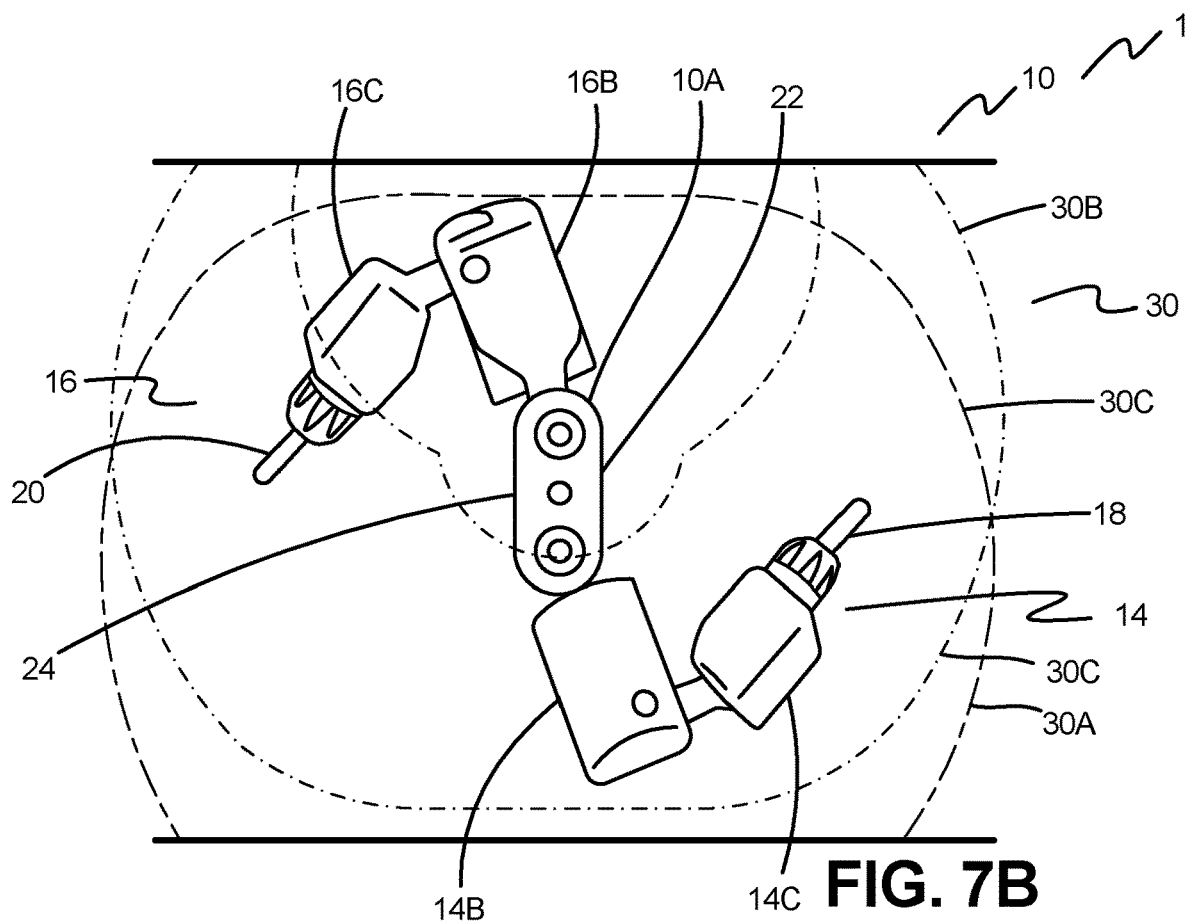
FIG. 7B is a top view of the implementation of FIG. 7A, showing the range of motion of the arms and the associated workspaces.
Figure 7C:
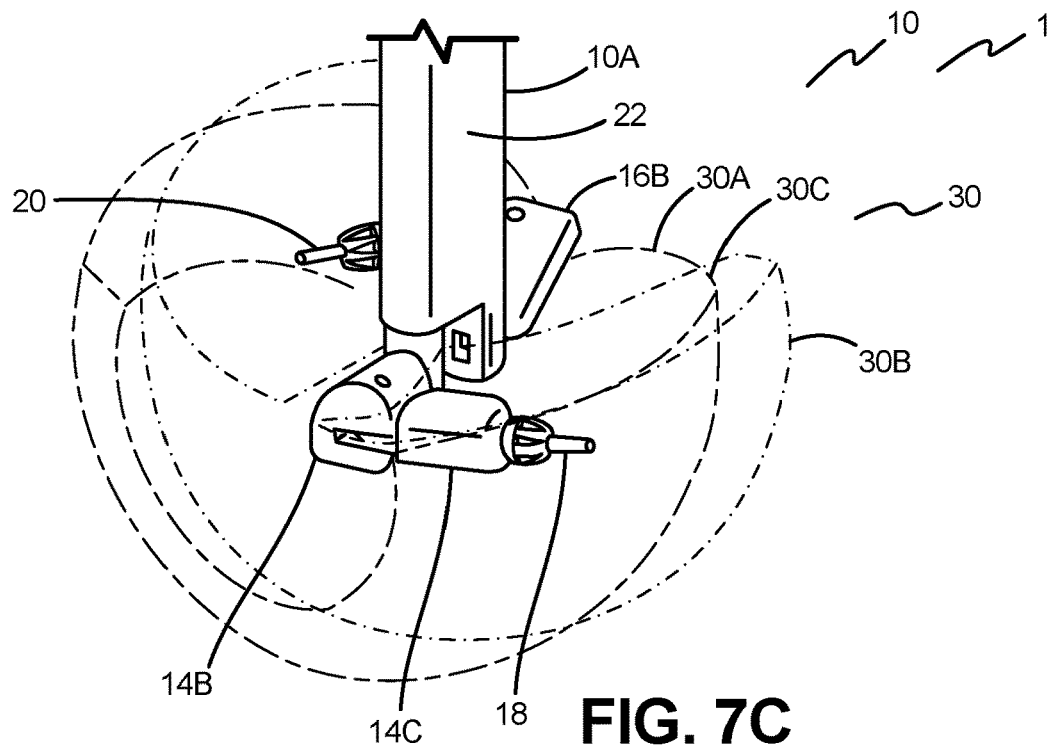
FIG. 7C is a perspective view of the implementation of FIG. 7A, showing the range of motion of the arms and the associated workspaces.

Similarly, FIGS. 7B and 7C depict different views of the device body 10A and arms 14, 16 of FIG. 7A. For example, FIG. 7B depicts a top view of the body 10A and arms 14, 16. In this embodiment, both the workspace 30A of the first arm 14 and the workspace 30B of the second arm 16 are shown from a top view. Further, FIG. 7C depicts the body 10A and arms 14, 16 from a perspective view that shows another angle of the workspaces 30A, 30B.

In each of FIGS. 7A-7C, the same configuration of the body 10A and arms 14, 16 is shown, with the first arm 14 extending out from the front 22 of the device while the second arm 16 is extending out from the back 24 (as best shown in FIG. 7A). This wide range of motion demonstrated by the workspaces 30A, 30B for both of its arms 14, 16 gives the robotic device 10 a relatively large workspace when compared to the length of its arms 14, 16.

Figure 8A:
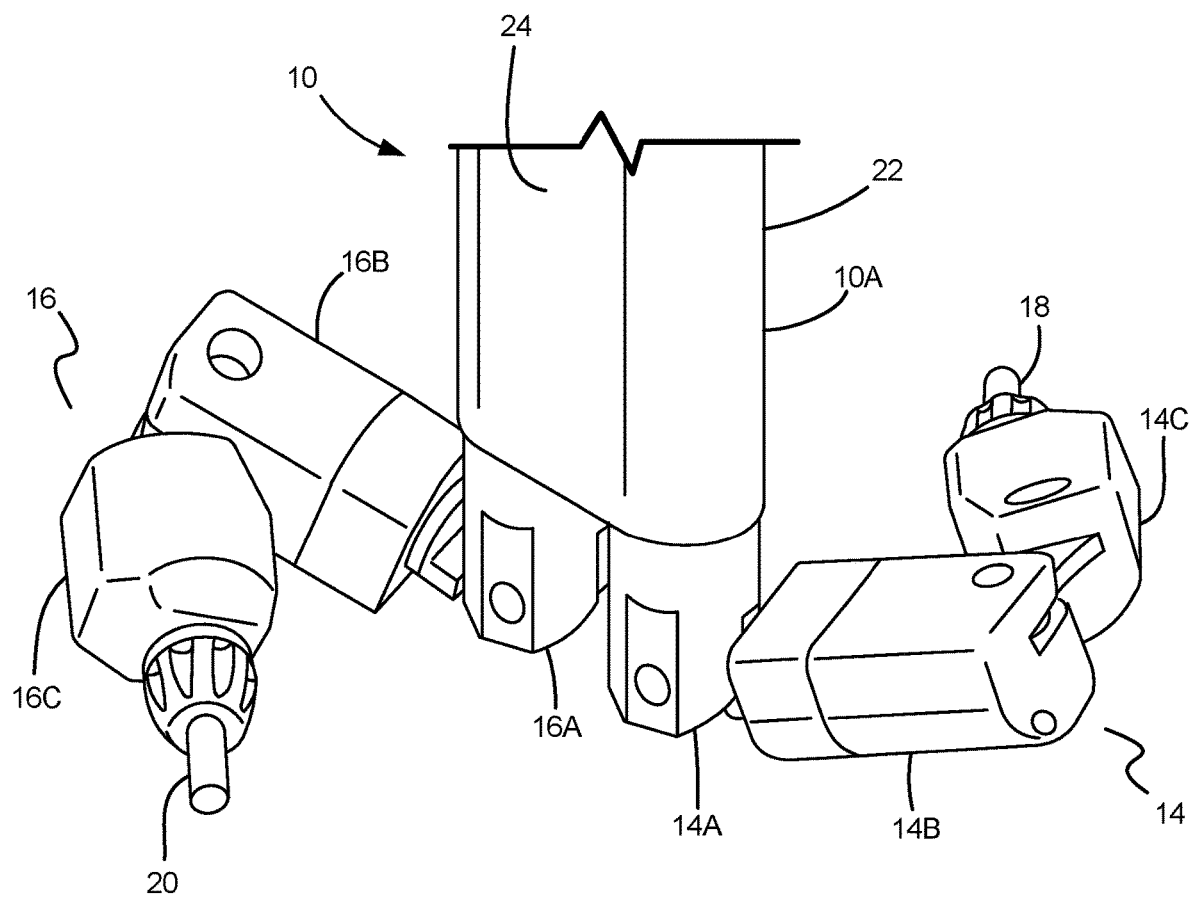
FIG. 8A is a rear perspective view of one implementation of a surgical device, showing the positioning of the arms to the ahead and behind the device, according to one embodiment.
Figure 8B:
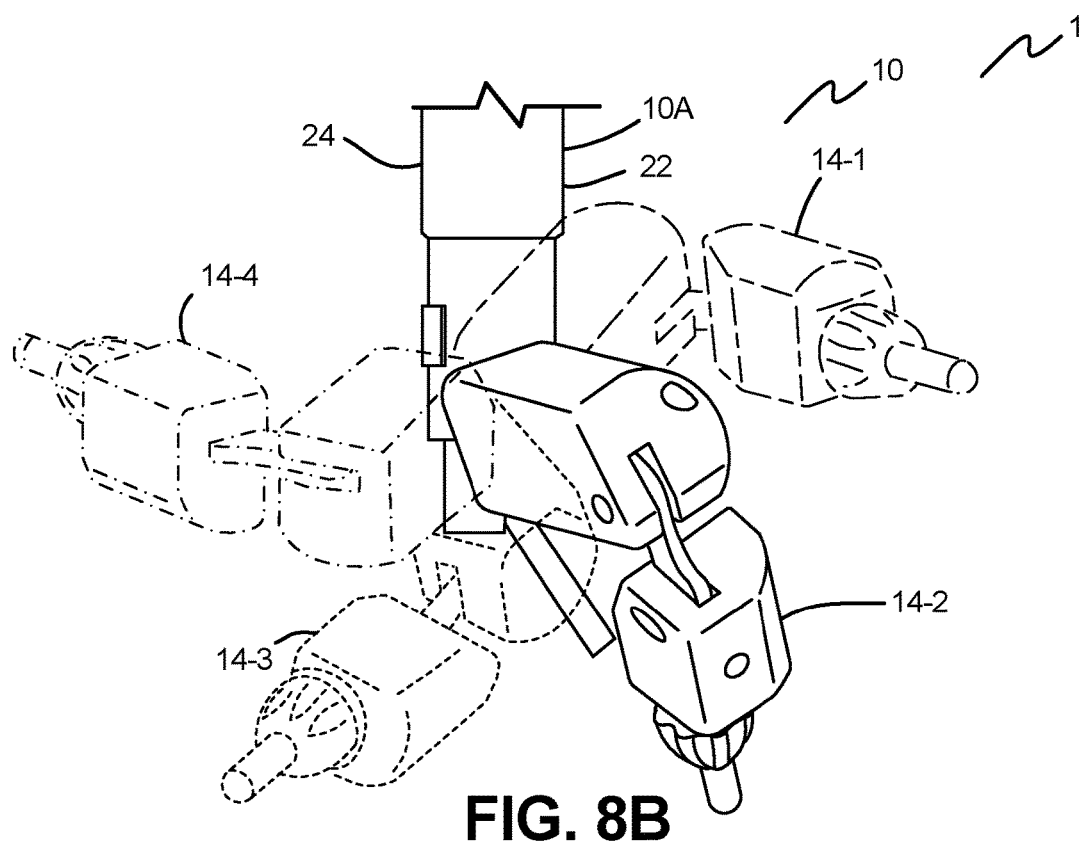
FIG. 8B is a three-quarters rear view of the device of FIG. 8A, showing several possible arm positions.
Figure 8C:
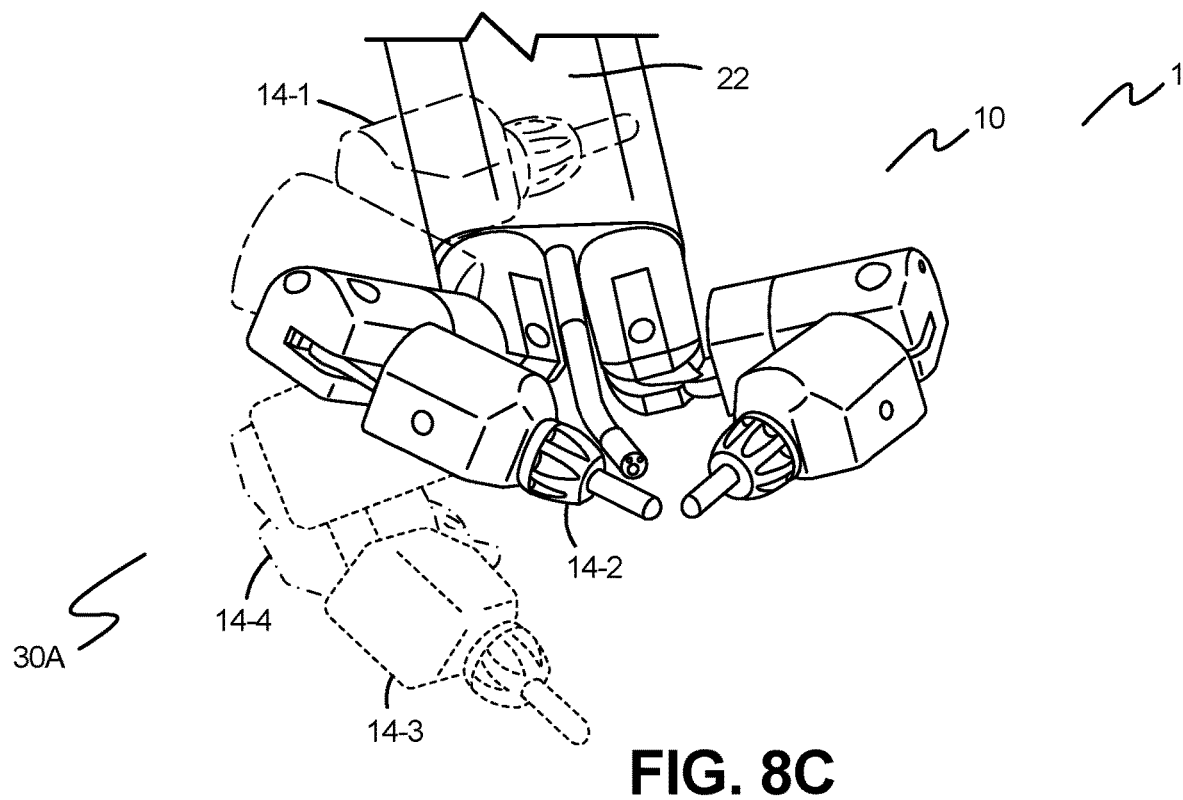
FIG. 8C is a lower perspective front view of the device showing the arm positions of FIG. 8B.

FIGS. 8A, 8B, and 8C further depict the wide range of motion that can be achieved by the arms of this specific device 10, according to one embodiment. FIG. 8A depicts a perspective view of the back of the device 10 in which the arms 14, 16 are both depicted in a single position that is substantially similar to that depicted in FIGS. 7A-7C: a first arm 14 extends away from the front 22 of the device body 10A, while the second arm 16 extends away from the back 24 of the device body 10A.

FIG. 8B depicts a side view of the device 10 in which the first arm 14 is depicted in multiple different positions, including a first position 14-1, a second position 14-2, a third position 14-3, and a fourth position 14-4, thereby providing some examples of the range of motion of which the arms (in this case, the first arm 14) are capable.

The implementation of FIG. 8C depicts a perspective front view of the device 10 in which the first arm 14 is again depicted in the same positions as shown in FIG. 8B, including the first 14-1, second 14-2, third 14-3, and fourth 14-4 positions within the workspace 30A. One of skill in the art would appreciate that many additional positions between those shown are also possible, and that these positions of the first arm 14 are also possible for the second arm 16.

Figure 9:
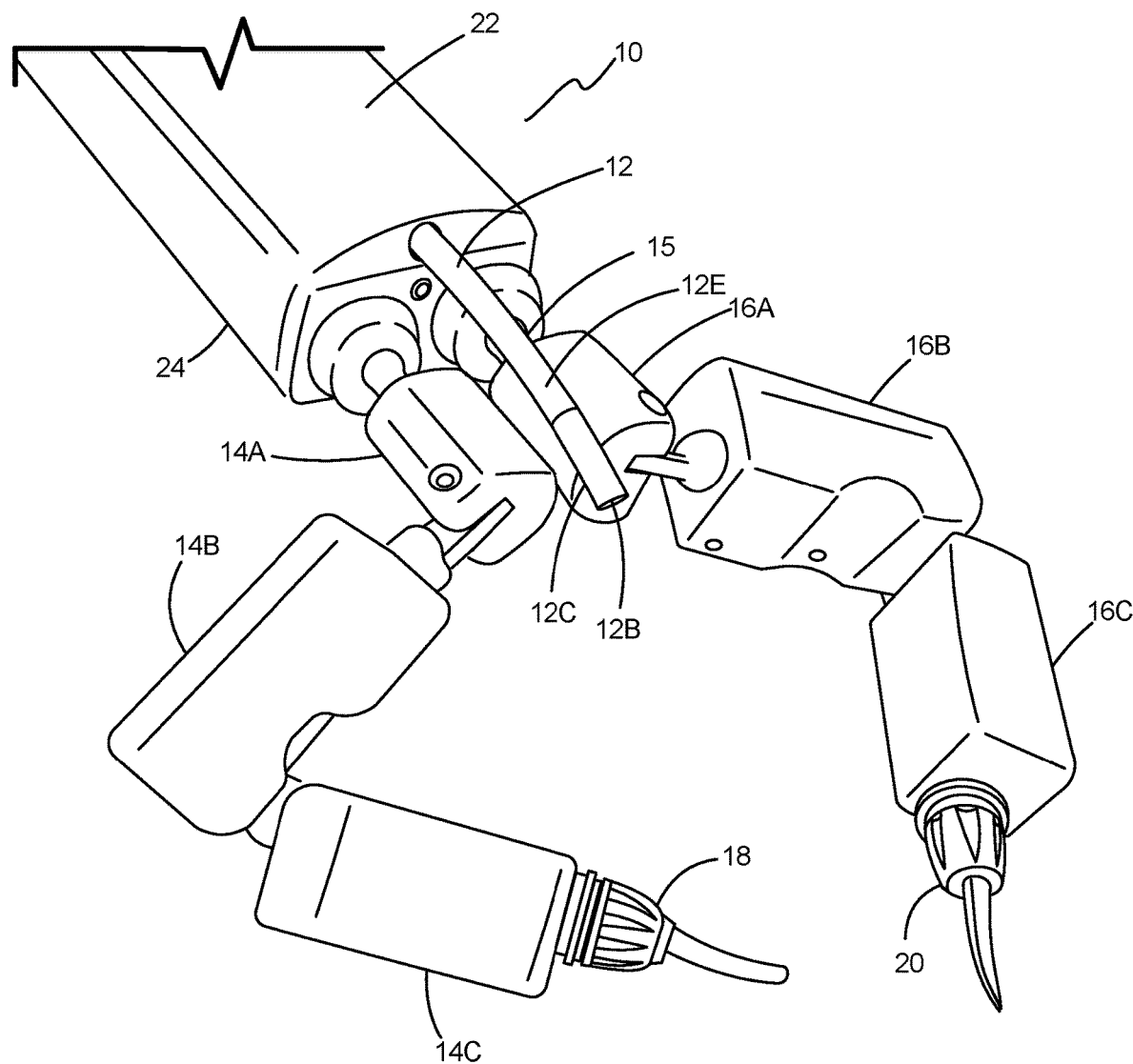
FIG. 9 is a perspective view of a surgical device according to one embodiment showing the camera and arms oriented in a central "down" work position.

FIG. 9 is a perspective front view of an implementation of the device 10 with an articulating, or flexible camera 12 extending from the distal end 10B of the device body 10A. In these implementations, the camera 12 has a distal lens 12B on the tip portion 12C, as well as a flexible sheath 15 enclosing the flexible section 12E. In FIG. 9A, the camera 12 and arms are generally oriented in a slightly "down" working position, wherein the tip portion 12C is oriented away from the front 22 of the body 10A. Again, it is understood that in these implementations, the camera 12 can therefore be positioned to best view the end effectors, or tools 18, 20. It is further understood that in these implementations the robot 10 exits the body on the forward surface 22.

FIG. 910 depicts a further implementation of the device 10 with the arms in an "up" or "normal" position, where the camera is angled slightly toward the front 22 of the body 10A. Further, the device of FIG. 10 has proximal sleeve attachments 32, 34 between the shoulders 14A, 16A and device body 10A. The sleeve attachments 32, 34 can be "grooves," where two flanges 32A, 32B, 34A, 34B are disposed around each shoulder shaft 36, 38. It is understood that flanges 32A, 32B, 34A, 34B are configured or otherwise constructed and arranged so that a permanent and/or disposable sleeve (not shown, but as is discussed in the incorporated references) can be attached and held in place between the respective flanges 32A, 32B, 34A, 34B. Corresponding distal mating areas 40, 42 for each sleeve (not shown) are disposed on the distal ends of the forearms 14C, 16C and at the base of each tool 18, 20.

Figure 10:
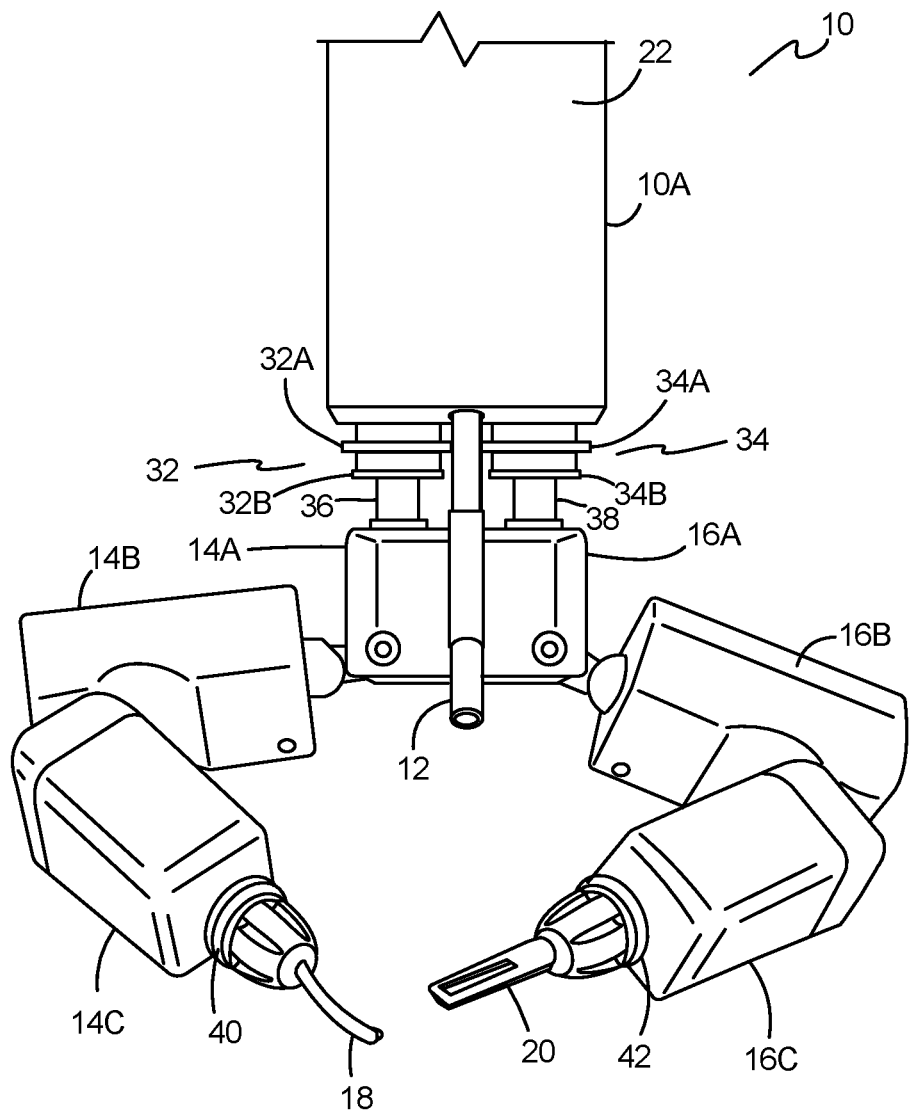
FIG. 10 is a front view of the device of FIG. 9 showing the arms in an central "up" position.
Figure 11:
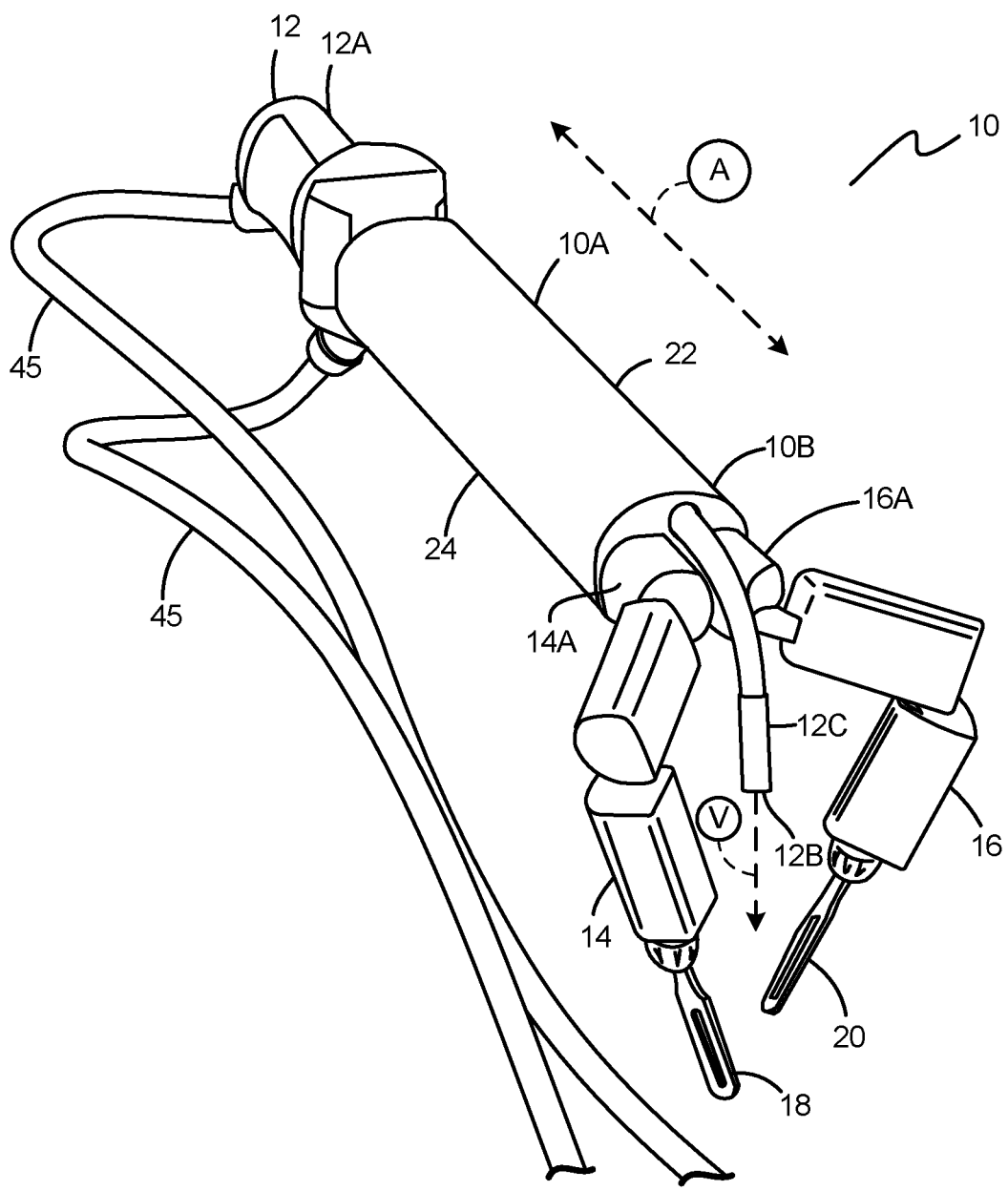
FIG. 11 is a perspective view of a surgical device according to one embodiment showing the arms in a "down" position.

FIG. 11 depicts a further implementation of a robot 10 having arms 14, 16 positioned substantially "down," compared to the positions of FIGS. 9 and 10. That is, in FIG. 11, the camera tip 12C is oriented perpendicularly from the longitudinal axis (reference arrow A) of the robot body 10A on the back side 24 (as opposed to the front side 22) within a region of the workspace 30, and that the camera 12 disposed such that the arms 14, 16, and more specifically the tools, or end effectors 18, 20 are within the field of view (shown generally with reference arrow V). In this implementation, various operations cables 45 are also shown as being connected to the device body 10A and camera 12.

Figure 12A:
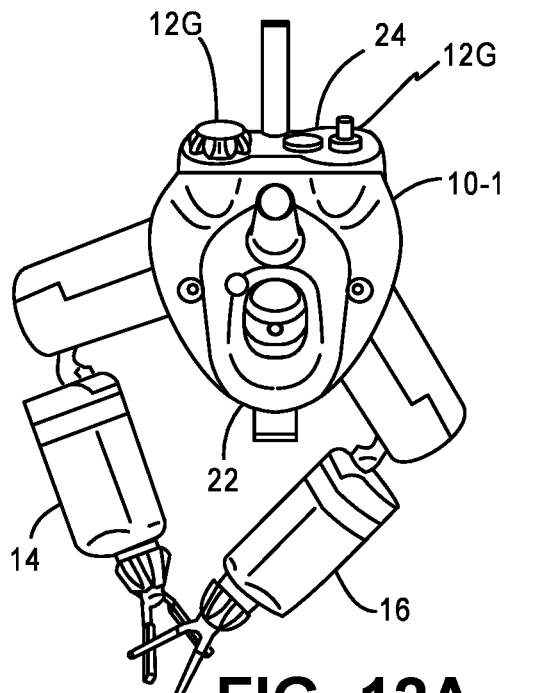
FIG. 12A is a top view of a surgical device, according to one implementation.
Figure 12B:
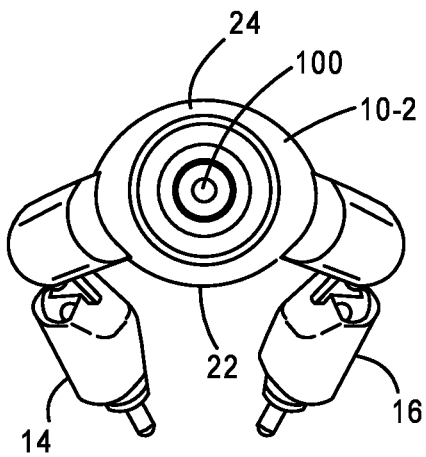
FIG. 12B is a top view of a surgical device, according to another implementation.
Figure 12C:
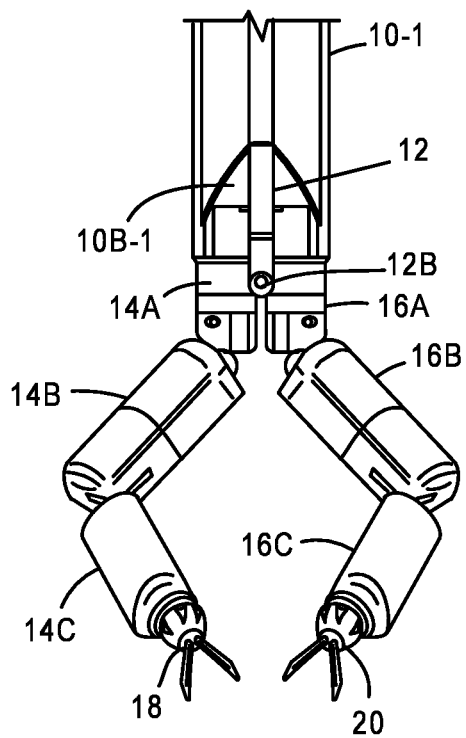
FIG. 12C is a front view of a surgical device, according to one implementation.
Figure 12D:
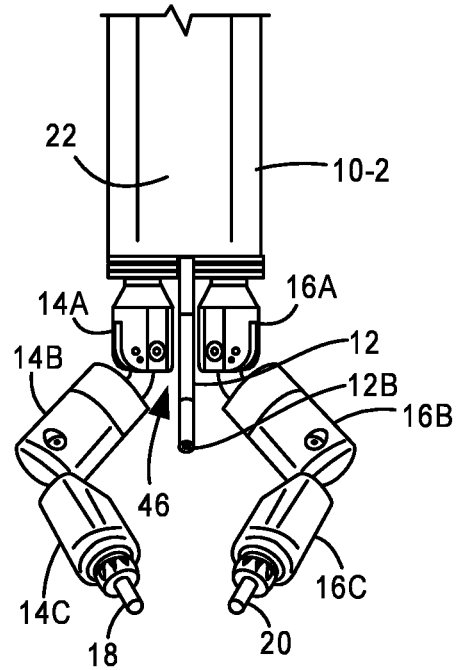
FIG. 12D is a front view of a surgical device, according to another implementation.
Figures 12E, 12F:
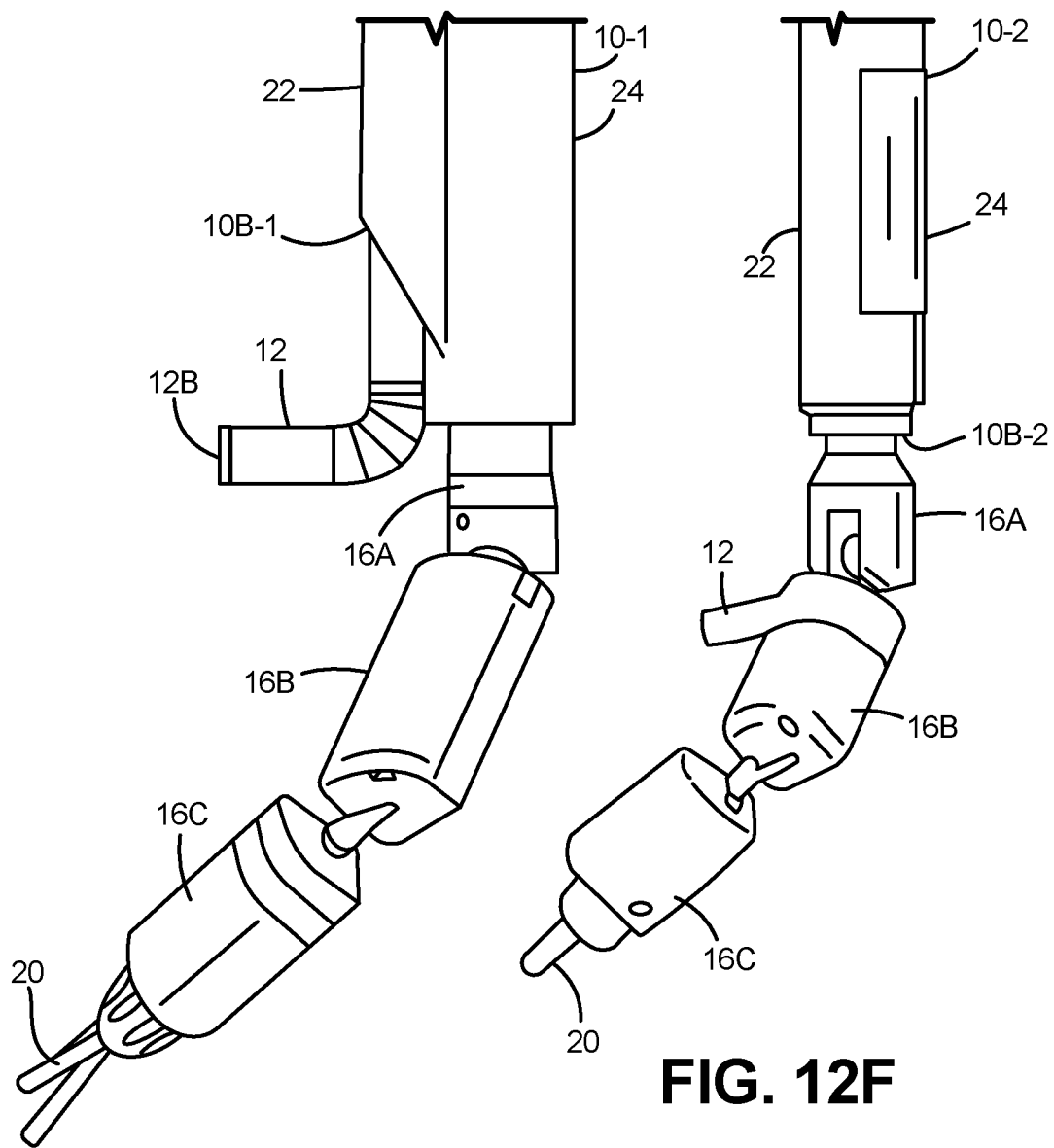
FIG. 12E is a side view of a surgical device, according to one implementation.
FIG. 12F is a side view of a surgical device, according to another implementation.
Figure 13A:
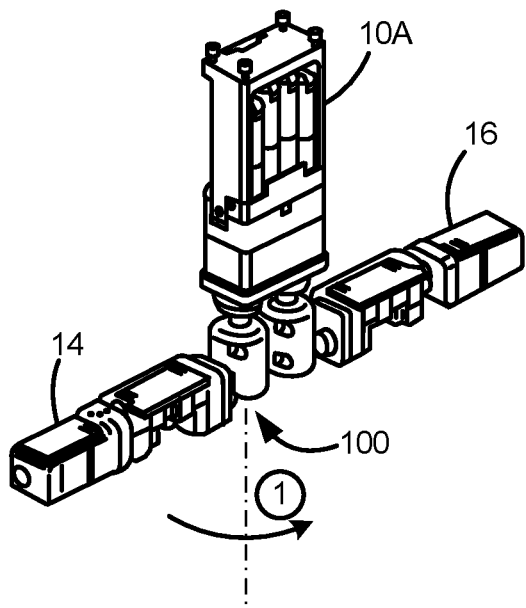
FIG. 13A is a perspective view of a surgical device according to one embodiment, showing the movement of the first joint.
Figure 13B:
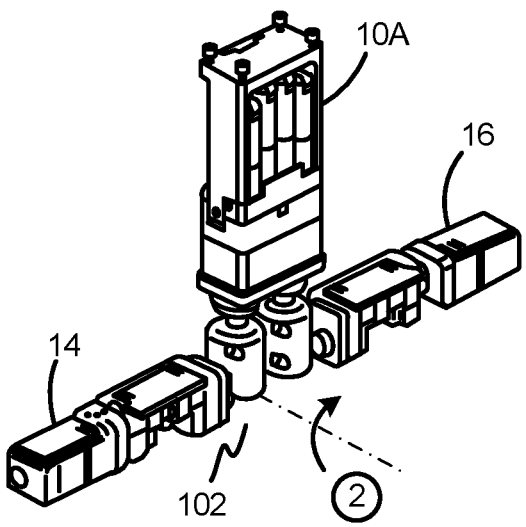
FIG. 13B is a perspective view of a surgical device according to one embodiment, showing the movement of the second joint.
Figure 13C:
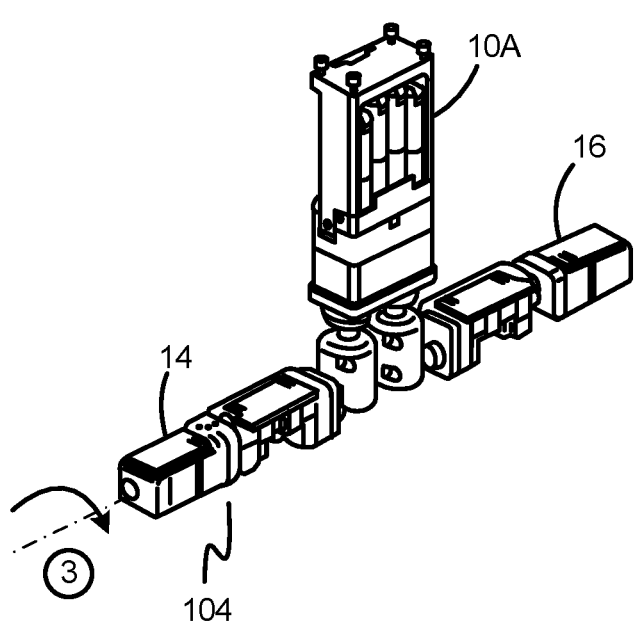
FIG. 13C is a perspective view of a surgical device according to one embodiment, showing the movement of the third joint.
Figure 13D:
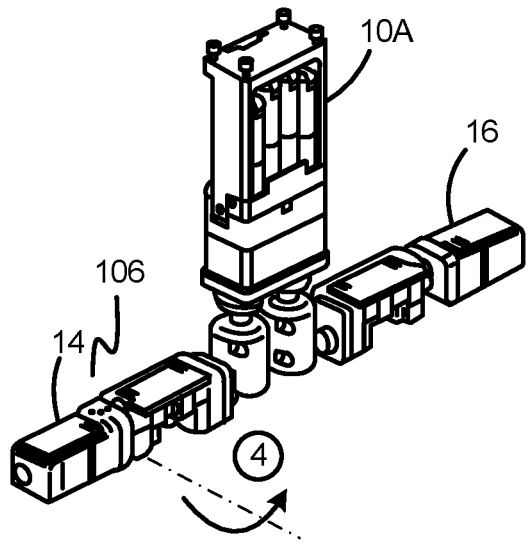
FIG. 13D is a perspective view of a surgical device according to one embodiment, showing the movement of the fourth joint.

FIGS. 12A-F depict alternate implementations of the robot 10-1, 10-2. In the first implementation, and as shown in FIGS. 12A, 12C and 12E, the robot 10-1 has a sloped distal body 10B-1 portion 48 the camera 12 extends from within. In the second implementation, as shown in FIGS. 12B, 12D and 12F, the robot 10-2 camera 12 extends from the distal body end 10B-2. In these implementations, the arms 14, 16 have generally cylindrical upper links, or shoulders 14A, 16A disposed in parallel—laterally and separately—on the distal body end 10B such that there is a "gap" or opening 46 between the shoulders 14A, 16A. In these implementations, the camera 12 extends from the distal end of the device body 10B within the opening 46, so as to be directly between the generally cylindrical shoulders 14A, 16A and equidistant between the front side 22 and back side 24. In these implementations, the camera 12 can therefore be curved to view forward and rearward equally, as is shown, for example, in relation to FIG. 6A-8C.

FIGS. 13-30 depict the internal components of the body 10A, which is shown in these figures without its casing or housing 11. It is understood that in use, these implementations are covered, as is shown in relation to FIG. 1A. FIGS. 13-30 include the internal structural or support components of the body 10A. These components maintain the structure of the body 12 and provide structural support for the components disposed therein.

In use, there are many ways to actuate the robot 10 and its associated components, such as DC motors, AC motors, Permanent magnet DC motors, brushless motors, pneumatics, cables to remote motors, hydraulics, and the like. A more detailed description of one possible system is described in relation to FIGS. 13-30. Other technologies described in the previously-filed and incorporated applications and patents can also be implemented to actuate the various components, as would be understood.

FIG. 13 shows an implementation of the robot 10 and each joint of one arm—here, the left arm 16. it is understood that the right arm 14 of this implementation is a mirror image of the left 16. It is understood that the internal components in the left arm 16 that operate/control/actuate the left arm 16 are substantially the same as those depicted and described herein and that the descriptions provided below apply equally to those components as well.

Figure 14:
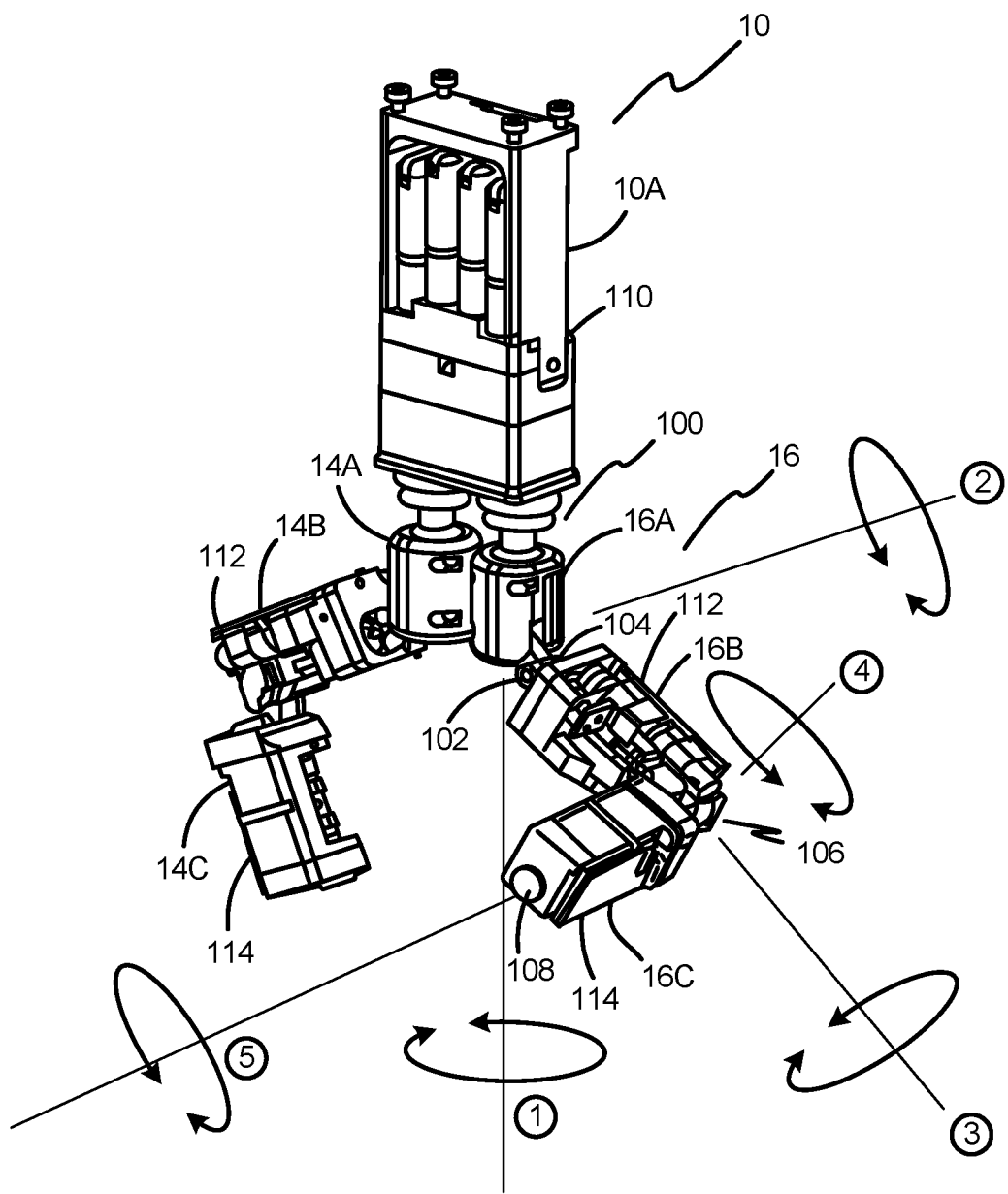
FIG. 14 is a perspective view of a surgical robotic device showing the internal components, according to one implementation.

In the implementation of FIG. 14, a shoulder yaw joint 100 actuates a yaw joint 100 in the robot shoulder 14A, 16A. In this implementation, the robot 10 also has a shoulder pitch joint 102, that is, a pitch joint 102 on the robot shoulder 14A, 16A. In these implementations, an upper arm roll joint 104, an elbow joint 106, and a tool roll joint 108 are also provided which enable the range of motion described in relation to Table 1, below. In various implementations, a tool actuation joint (not shown) interfaces with the tool (not shown) to actuate open and close of the tool, as has been previously described.

In various implementations, these joints 100, 102, 104, 106 have practical defined ranges of motions that, together with the robot geometry, lead to the final workspace of the robot 10. For the examples given herein, the joint limits allow for a significant robot workspace, as is described above. This workspace allows the various implementations of the robot to use both arms and hands effectively in several locations within the body cavity of the patient. The joint ranges of motion defined in the implementations of FIGS. 13A-27 are given in Table 1. It is understood that further ranges are possible, and so this set of ranges is not limiting, but rather representative of a particular embodiment. Further, alternate embodiments are possible.

The direction of rotation and zero positions are shown in FIGS. 13A-D. In FIGS. 13A-D, the robot 10 is shown with each of the first four angles in the zero location. In these implementations, each joint (the shoulder yaw joint 100, shoulder roll joint 102, upper arm roll joint 104 and elbow joint 106) is shown with an axis of rotation (dotted) and a zero location. An arrow is then used to indicate the direction of positive joint angle about the axis of rotation. Since the tool roll joint 108 and tool actuation joints 109 are allow continuous rotation the zero location is arbitrary and not shown.

TABLE 1

Joint Ranges of Motion

| Joint No. | Range of Motion |
| --- | --- |
| 1 | −90 to +90 |
| 2 | −90 to +30 |
| 3 | −90 to +90 |
| 4 | 0 to 150 |
| 5 | Continuous |
| 6 | Continuous |

In the implementation of FIG. 14, the body 10A and each link (meaning the upper arm 16B, and forearm 16C) contain Printed Circuit Boards ("PCBs") 110, 112, 114 that have embedded sensor, amplification, and control electronics. One PCB is in each forearm and upper arm and two PCBs are in the body. Each PCB also has a full 6 axis accelerometer-based Inertial Measurement Unit and temperature sensors that can be used to monitor the temperature of the motors. Each joint can also have either an absolute position sensor or an incremental position sensor or both. In certain implementations, the some joints contain both absolute position sensors (magnetic encoders) and incremental sensors (hall effect). In other implementations, certain joints only have incremental sensors. These sensors are used for motor control. The joints could also contain many other types of sensors. A more detailed description of one possible method is included here.

In this implementation, a larger PCB 110 is mounted to the posterior side of the body 10A. This body PCB 110 controls the motors 116 in the base link, or body 10A (the shoulder yaw joint 100 and shoulder pitch joint 102 for left and right arms, respectively). Each upper arm has a PCB 112 to control the upper arm roll joint 104 and elbow joint 106. Each forearm has a PCB 114 to control the tool roll joint 108 and tool actuation joint (not shown). In the implementation of FIG. 14, each PCB 110, 112, 114 also has a full six axis accelerometer-based inertial measurement unit and several temperature sensors that can be used to monitor the temperature of the various motors described herein.

Figure 15:
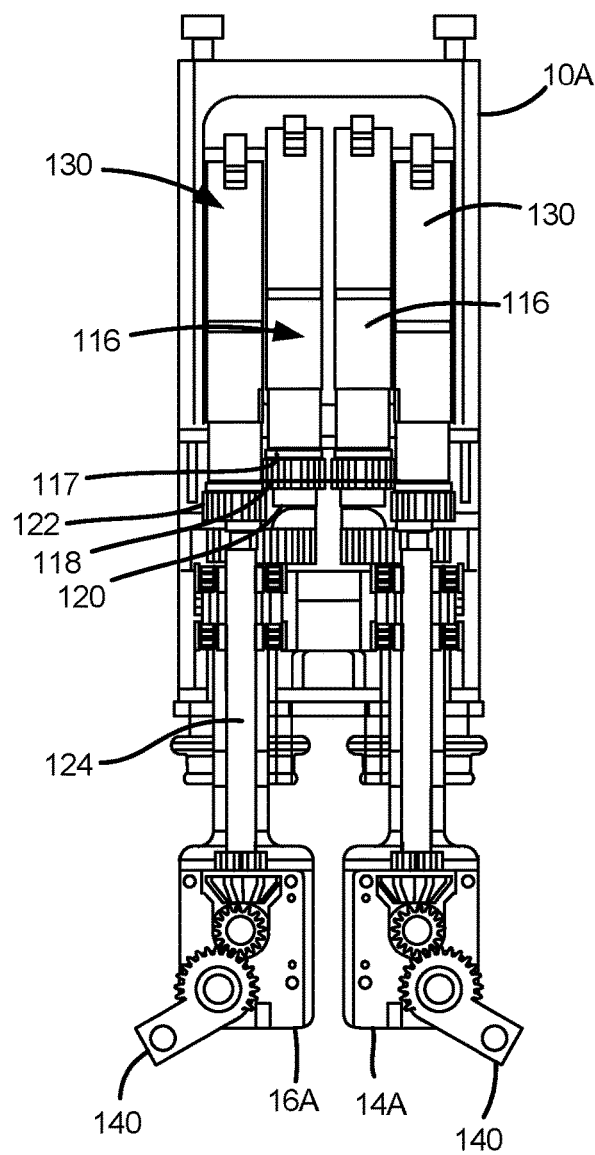
FIG. 15 is a front view showing the internal components of the body and shoulders, according to one embodiment.
Figure 22:
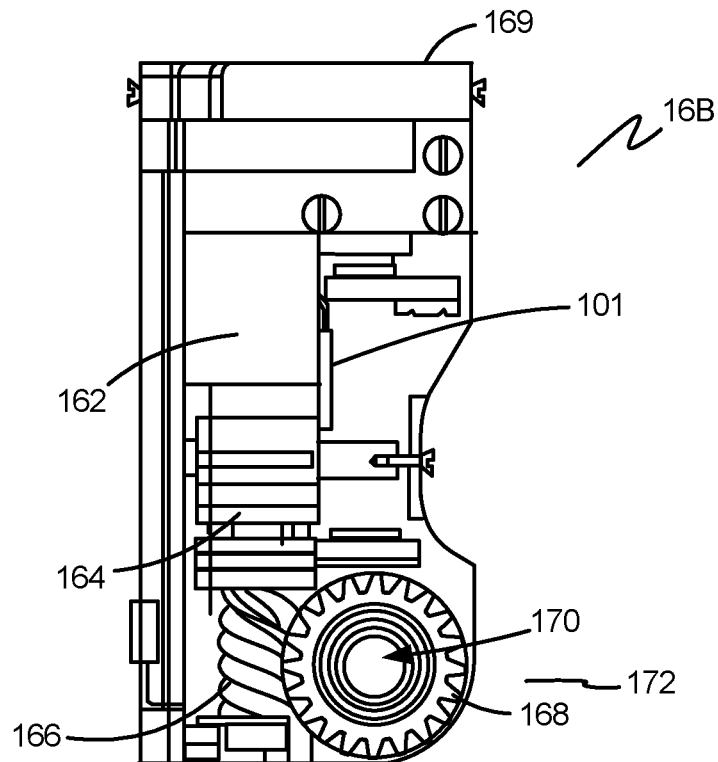
FIG. 22 is a front view showing further internal components of the upper arm, according to one embodiment.

In these embodiments, each joint 100, 102, 104, 106, 108 can also have either an absolute position sensor or an incremental position sensor or both, as described and otherwise disclosed in U.S. Provisional Application 61/680, 809, filed on Aug. 8, 2012, which is hereby incorporated herein by reference in its entirety. In one implementation, and as shown in FIG. 15 and elsewhere the various actuators or motors 116, 130, 154, 178 described herein have at least one temperature sensor 101 disposed on the surface of the motor, for example by temperature-sensitive epoxy, such that the temperature sensors (as shown in FIG. 22 at 101) can collect temperature information from each actuator for transmission to the control unit, as discussed below. In one embodiment, any of the motors discussed and depicted herein can be brush or brushless motors. Further, the motors can be, for example, 6 mm, 8 mm, or 10 mm diameter motors. Alternatively, any known size that can be integrated into a medical device can be used. In a further alternative, the actuators can be any known actuators used in medical devices to actuate movement or action of a component. Examples of motors that could be used for the motors described herein include the EC 10 BLDC+GP10A Planetary Gearhead, EC 8 BLDC+GP8A Planetary Gearhead, or EC 6 BLDC+GP6A Planetary Gearhead, all of which are commercially available from Maxon Motors, located in Fall River, Mass. There are many ways to actuate these motions, such as with DC motors, AC motors, permanent magnet DC motors, brushless motors, pneumatics, cables to remote motors, hydraulics, and the like. Further implementations can be used in conjunction with the various systems, methods and devices disclosed in U.S. patent application Ser. No. 15/227,813 filed Aug. 3, 2016 and entitled "Robotic Surgical Devices, Systems, and Related Methods," which is incorporated by reference in its entirety.

In this implementation, joints 1-4 have both absolute position sensors (magnetic encoders) and incremental sensors (hall effect). Joints 5 & 6 only have incremental sensors. These sensors are used for motor control. It is understood that the joints could also contain many other types of sensors, as have been described in detail in the incorporated applications and references.

Figure 16:
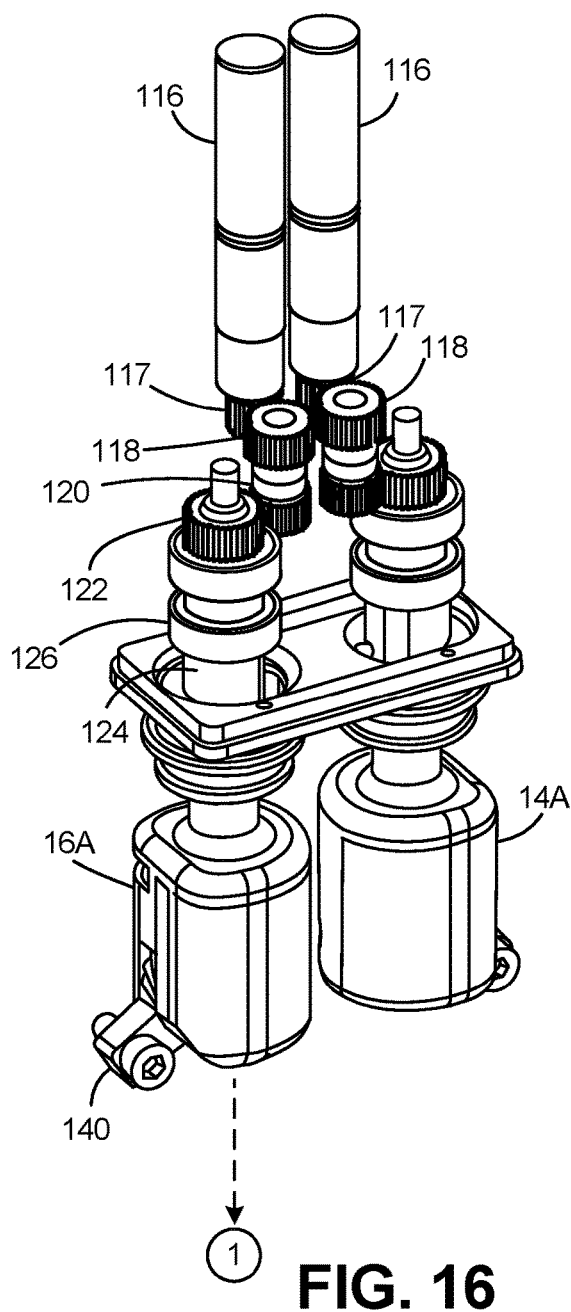
FIG. 16 is a perspective view showing the internal components of the body, according to one embodiment

According to one implementation, certain other internal components depicted in the implementation of FIGS. 15-16 are configured to actuate the rotation of the shoulder yaw joint 100 of the body 10A around axis 1, as shown in FIG. 14. It is understood that two of each of the described components are used—one for each arm—but for ease of description, in certain depictions and descriptions, only one is used.

As best shown in FIG. 15, a shoulder yaw joint 100 motor 116 and gearhead combination drives a motor gear 117 first spur gear set 118, which is best shown in FIG. 16. The first spur gear set 118 drives a shaft supported by bearings 120 to drive a second spur gear set 122. In turn, this second spur gear set 122 drives an output shaft 124 that is also supported by bearings 126. This output shaft 124 then drives a turret 14A, 16A (representing the shoulder of the robot 10) such that the shoulder 16A rotates around axis 1, as best shown in FIG. 14.

Figure 17:
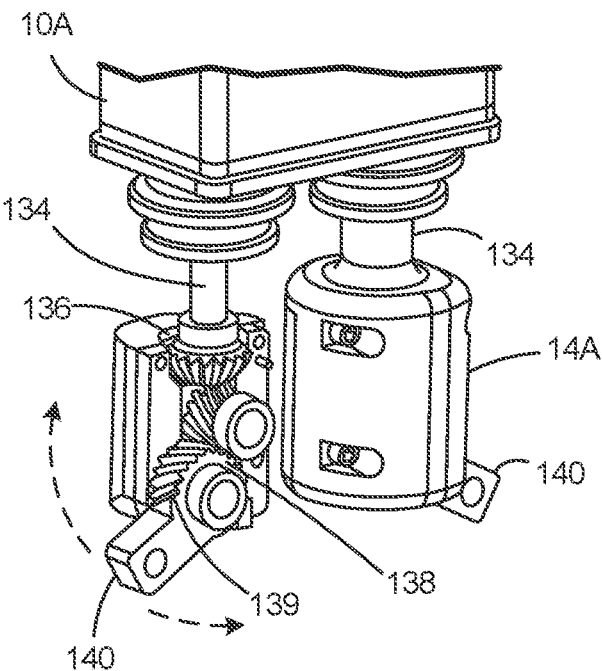
FIG. 17 is a perspective view showing the internal components of the shoulders, according to one embodiment.
Figure 18:
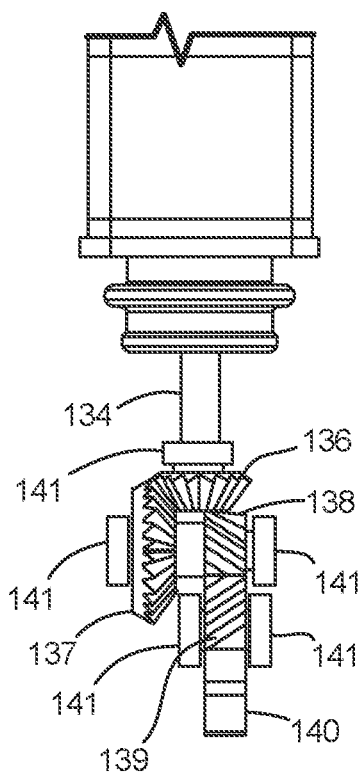
FIG. 18 is a side view showing the internal components of the shoulders, according to one embodiment.
Figure 19:
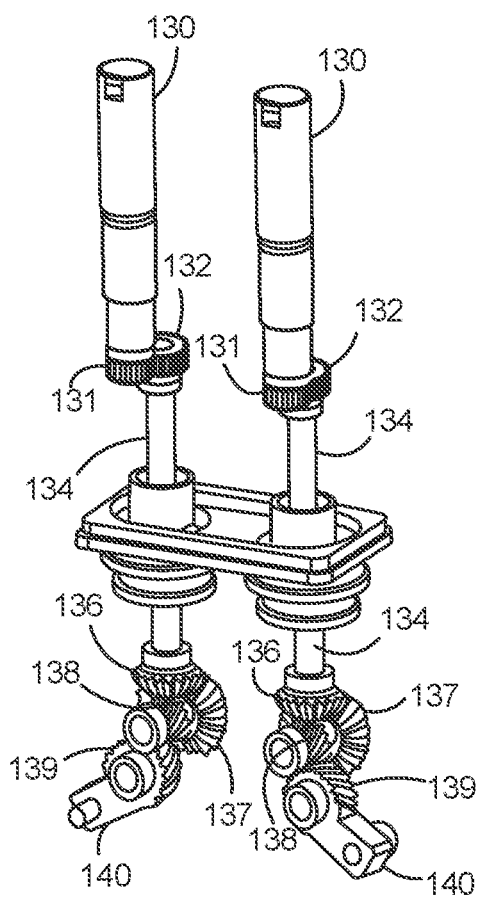
FIG. 19 is a reverse perspective view showing the internal components of the body and shoulders, according to one embodiment.

According to one implementation, certain internal components depicted in the implementation of FIGS. 17-19 are configured to actuate the shoulder pitch joint 102 of the body 10A and/or shoulder 14A, 16A around axis 2, as is shown in FIG. 14. In these implementations, the pitch joint 102 is constructed and arranged to pivot the output link 140 so as to move the upper arm (not shown) relative to the shoulder 14A, 16A.

In this implementation, a motor 130 and gearhead combination drives a motor gear 131 and spur gear 132 that in turn drives a first shaft 134. This shaft 134 then drives a bevel (or miter) gear pair 136, 137 inside the shoulder turret (depicted in FIG. 19). The bevel (or miter) gear pair 136, 137 accordingly drives a helical spur set 138, 139 directly connected to the shoulder pitch joint 102 output link 140, such that the upper arm 16B rotates around axis 2, as best shown in FIG. 14. In this implementation, the shoulder yaw joint 100 and the shoulder pitch joint 102 therefore have coupled motion. In these implementations, a plurality of bearings 141 support the various gears and other components, as has been previously described.

FIGS. 20-23 depict various internal components of the upper arm 16B constructed and arranged for the movement and operation of the arm 16. In various implementations, multiple actuators or motors 142, 154 are disposed within the housing (not shown) of the forearm 16C. FIGS. 24-27 depict various internal components of the forearm 16C constructed and arranged for the movement and operation of the end effectors. In various implementations, multiple actuators or motors 175, 178 are disposed within the housing (not shown) of the forearm 16C.

In one implementation, and as shown in FIG. 22 and elsewhere the various actuators or motors 116, 130, 154, 178 described herein have at least one temperature sensor 101 disposed on the surface of the motor, for example by temperature-sensitive epoxy, such that the temperature sensors can collect temperature information from each actuator for transmission to the control unit, as discussed below. In one embodiment, any of the motors discussed and depicted herein can be brush or brushless motors. Further, the motors can be, for example, 6 mm, 8 mm, or 10 mm diameter motors. Alternatively, any known size that can be integrated into a medical device can be used. In a further alternative, the actuators can be any known actuators used in medical devices to actuate movement or action of a component. Examples of motors that could be used for the motors described herein include the EC 10 BLDC+GP10A Planetary Gearhead, EC 8 BLDC+GP8A Planetary Gearhead, or EC 6 BLDC+GP6A Planetary Gearhead, all of which are commercially available from Maxon Motors, located in Fall River, Mass. There are many ways to actuate these motions, such as with DC motors, AC motors, permanent magnet DC motors, brushless motors, pneumatics, cables to remote motors, hydraulics, and the like.

Figure 20:
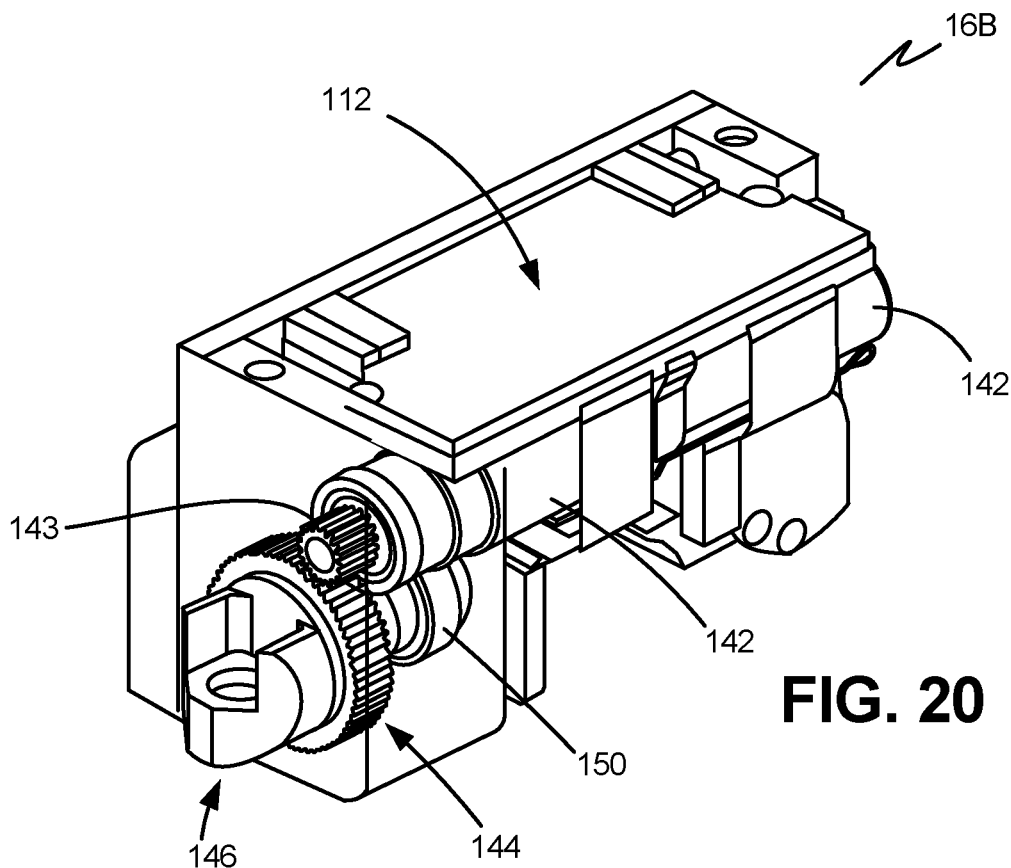
FIG. 20 is a perspective view showing the internal components of the upper arm, according to one embodiment.
Figure 21:
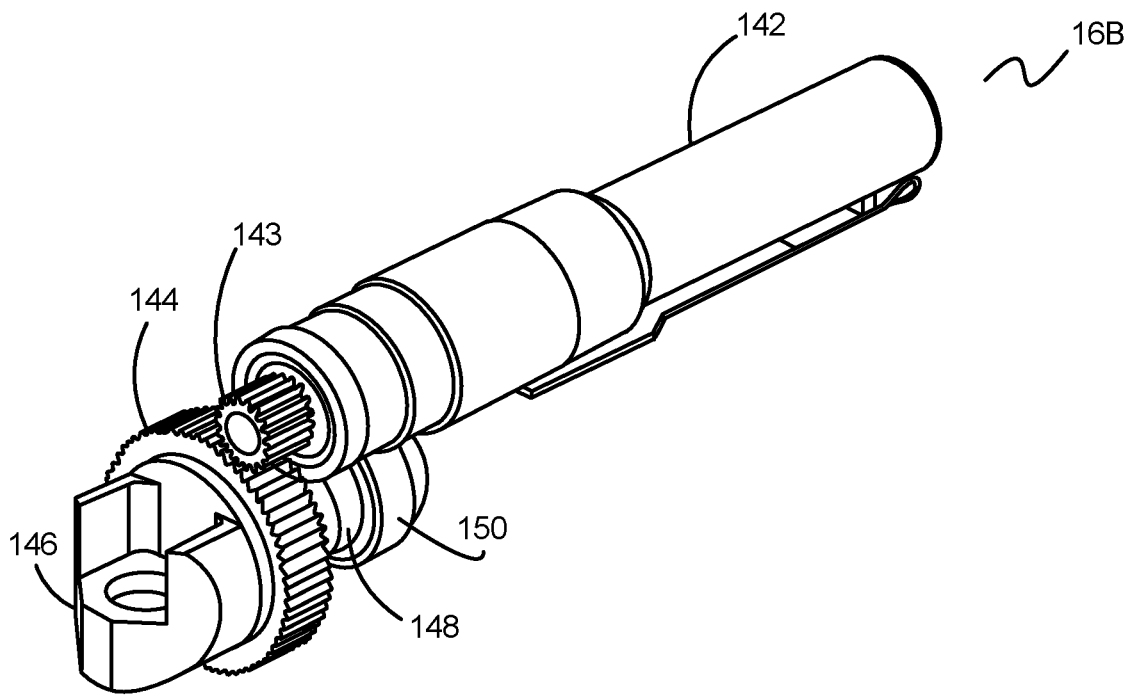
FIG. 21 is a perspective view showing further internal components of the upper arm, according to one embodiment.

One implementation of the internal components of the upper arm 16B constructed and arranged to actuate the upper arm roll joint 104 is shown in FIGS. 20-21. In this implementation, a motor 142 and gearhead combination controlled by a PCB 112 drives a motor gear 143 and corresponding spur gear 144 where the output spur gear 144 is supported by a shaft 148 and bearings 150. The output shaft 152 and output spur gear 144 can have a mating feature 146 that mates to the shoulder pitch joint 102 output link 140 (shown in FIG. 17).

Figure 23:
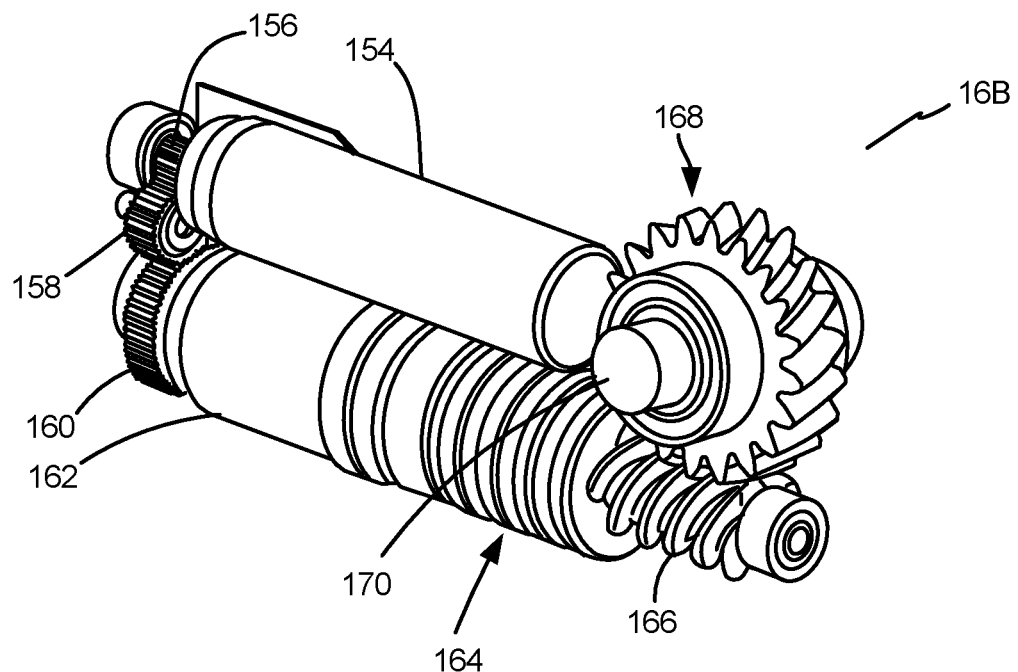
FIG. 23 is a perspective view showing further internal components of the upper arm, according to one embodiment.

One implementation of the internal components of the upper arm 16B configured to operate the elbow joint 106 is shown in FIGS. 22-23. In this implementation, a base motor 154 directly drives a driven spur gear set that includes three gears 156, 158, 160. This spur gear set 156, 158, 160 transfers the axis of rotation from the axis of the motor 154 to the axis of a worm gear 166.

As best shown in FIG. 23, the output spur gear 160 from this set drives a motor gearhead 162 that drives a worm shaft 164 that has a worm gear 166 mounted on it. This worm gear 166 then drives a worm wheel 168 that is connected to the Joint 4 output shaft 170. It should also be noted that the upper arm unit (as shown in FIG. 22) shows a curved concave region 172 on the right side. It is understood that this region 172 is configured to allow for a larger motion of Joint 4 so as to allowi the forearm to pass through the region 172.

Figure 24:
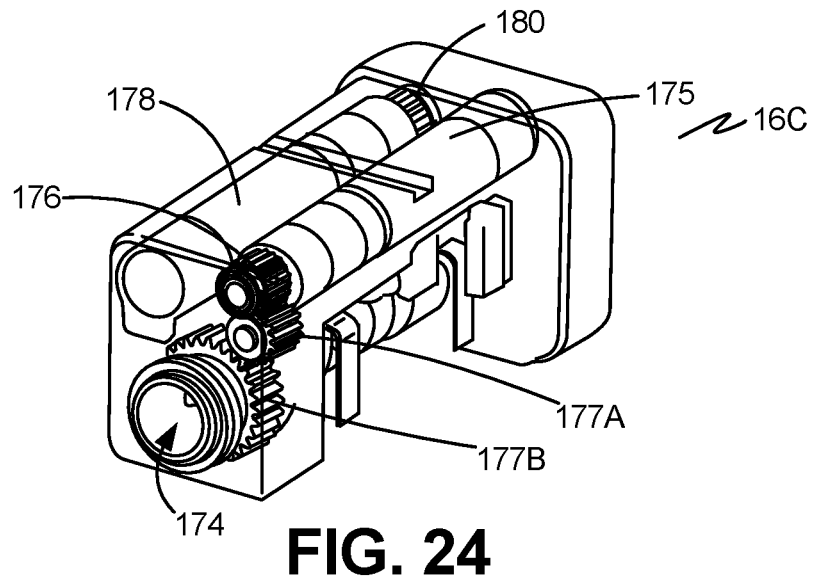
FIG. 24 is a perspective view showing internal components of the lower arm, according to one embodiment.
Figure 25:
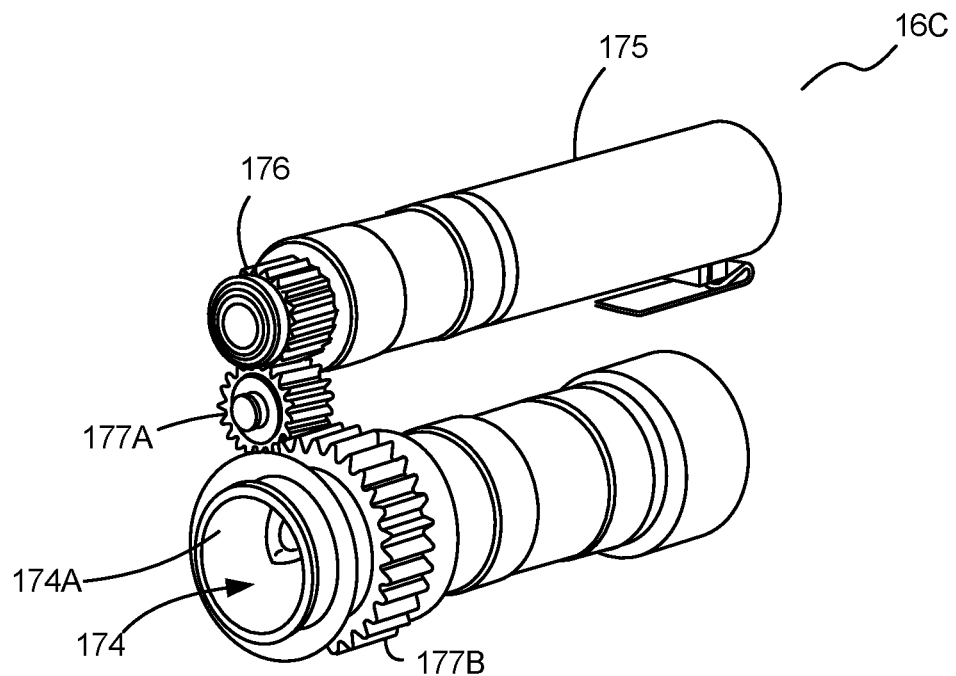
FIG. 25 is a perspective view showing further internal components of the upper arm, according to one embodiment.

One implementation of the internal components of the forearm 16C configured or otherwise constructed and arranged to operate the tool roll joint 108 is shown in FIGS. 24-25. In these implementations, the tool roll joint 108 drives a tool lumen 174 that holds the tool (shown, for example, at 18, 20 in FIGS. 1A-1B). The tool lumen 174 is designed to mesh with the roll features on the tool to cause the tool to rotate about its axis, as shown as axis 5 in FIG. 14. In this implementation, a tool roll motor 175 with a gearhead is used to drive a motor gear 176 and spur gear chain with two gears 177A, 177B. The last gear of this chain 177B is rigidly mounted to the tool lumen 174, so as to rotate the inner surface 174A of the tool lumen, and correspondingly any inserted end effector.

Figure 26:
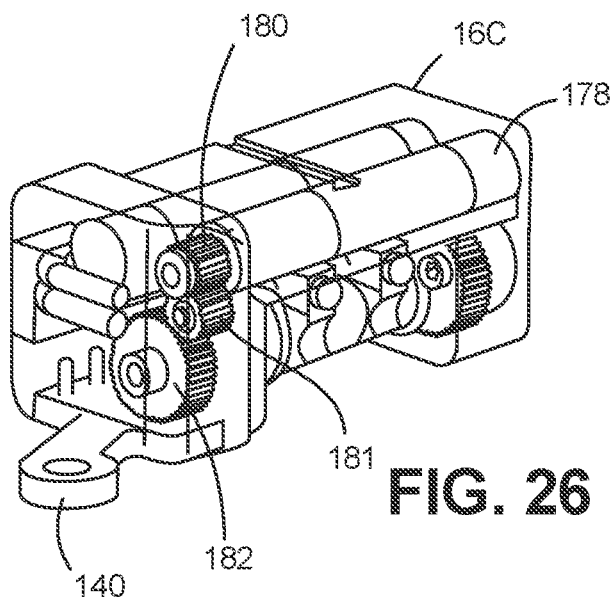
FIG. 26 is a perspective view showing further internal components of the upper arm, according to one embodiment.
Figure 27:
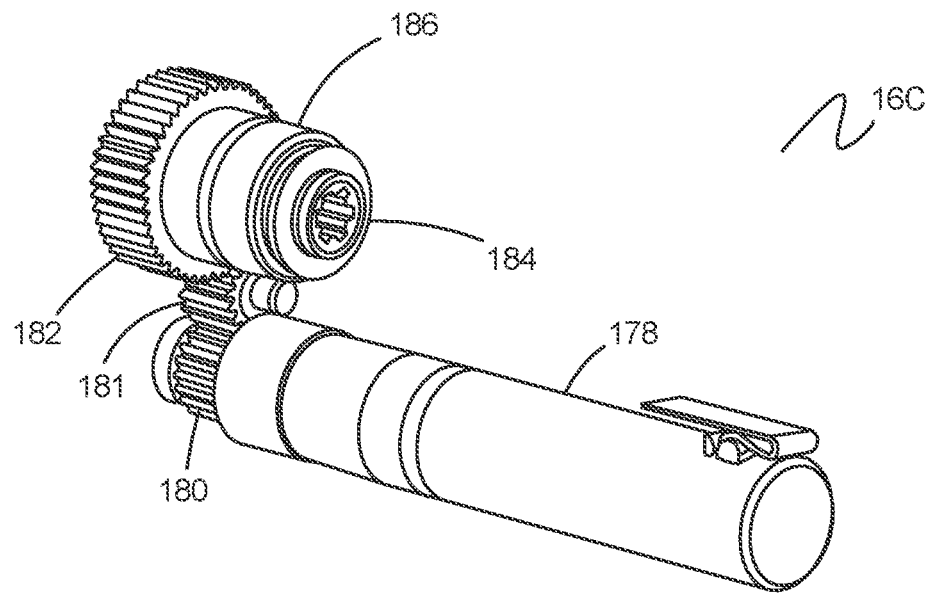
FIG. 27 is a perspective view showing yet further internal components of the upper arm, according to one embodiment.

One implementation of a tool actuation joint 109 is shown in FIGS. 26-27. In this implementation, the Joint 6 motor 178 does not visibly move the robot. Instead, this tool actuation joint 109 drives a female spline 184 that interfaces with the tool (Shown, for example, at 18, 20 in FIGS. 1A-1B) and is configured to actuate the end effector to open and close. This rotation of the end effector arms such that the end effector opens and closes is also called "tool drive." The actuation, in one aspect, is created as follows. An actuator 178 is provided that is, in this implementation, a motor assembly 178. The motor assembly 178 is operably coupled to the motor gear 180, which is a spur gear in this embodiment. The motor gear 180 is coupled to first 182 and second 183 driven gears such that rotation of the motor gear 180 causes rotation of the driven gears 182, 183. The driven gears 182, 183 are fixedly coupled to a female tool spline 184, which is supported by bearing pair 186. The female tool spline 184 is configured to interface with a male tool spline feature on the end effector to open/close the tool as directed.

According to one implementation, the end effector (shown at FIGS. 1A-1B at 18, 20) can be quickly and easily coupled to and uncoupled from the forearm 16C in the following fashion. With both the roll and drive axes fixed or held in position, the end effector 18, 20 can be rotated, thereby coupling or uncoupling the threads (not shown). That is, if the end effector is rotated in one direction, the end effector is coupled to the forearm 16B, and if it is rotated in the other direction, the end effector is uncoupled from the forearm 16B.

Various implementations of the system 10 are also designed to deliver energy to the end effectors so as to cut and coagulate tissue during surgery. This is sometimes called cautery and can come in many electrical forms as well as thermal energy, ultrasonic energy, and RF energy all of which are intended for the robot.

In exemplary implementations of the system 1 and various devices 10, the camera 12 is configured or otherwise constructed and arranged to allow for both pitch (meaning "up" and "down") movements and yaw (meaning "side to side" movements) within the workspace 30, and in exemplary implementations, the yaw or "pan" functionality is accomplished via mechanical articulation at the distal tip 12C, rather than via rotating the camera shaft 12D and/or handle 12A, as has been done previously. Accordingly, various implementations of the camera component 12 of this implementation have two mechanical degrees of freedom: yaw (look left/right) and tilt (look up/down). In use, the camera component 12 has pan and tilt functionality powered and controlled by the actuators and electronics in the handle 12A, as has been previously described in U.S. patent application Ser. No. 15/227,813. In these implementations of the system, the camera 12 is therefore able to allow the user to observe the device arms and end effectors throughout the expanded workspace. Several devices, systems and methods allowing for this improved range of vision and camera movement are described herein.

Figure 28A:
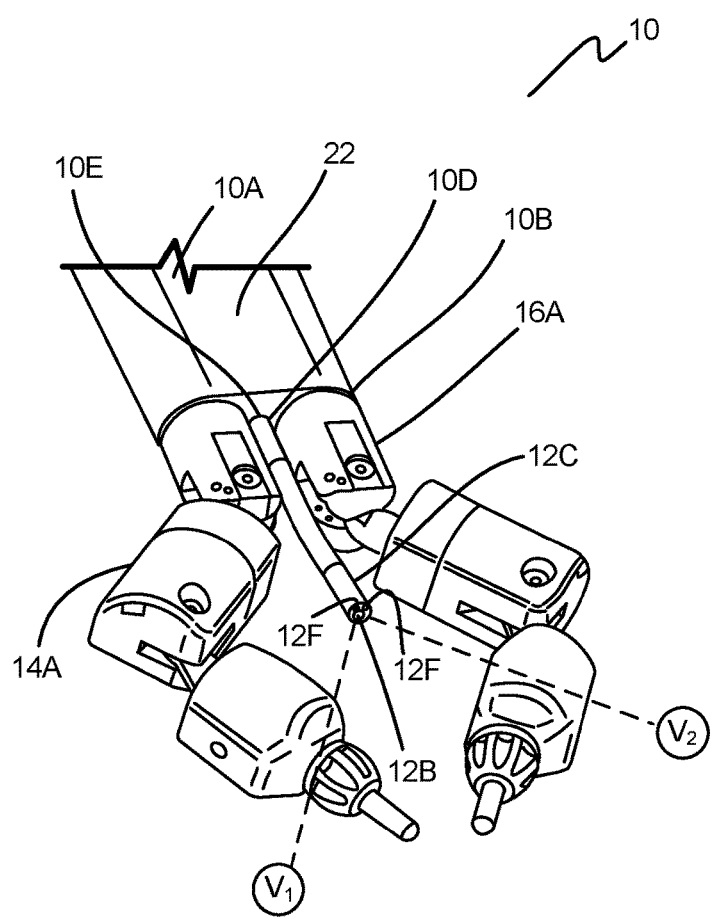
FIG. 28A is a front perspective view of a surgical device having an articulating camera, according to one embodiment.

Various implementations and components of the camera are shown in FIGS. 28A-36C and elsewhere. As discussed above, the camera 12 of certain implementations is designed to function with the robot 10, as is shown in FIG. 2. The robot camera 12 can also be used independent of the robot, as shown FIG. 4. In various implementations, the camera 12 is inserted into the proximal end 10C of the robot body 10A, and as is shown in FIG. 28A, the camera tip 12C exits through the distal end 10B of the robot body 10A near the attachment location between the body and arms, as described above in relation to FIG. 6. In certain implementations, and as discussed in relation to FIG. 3, a seal 10E is included in the robot body 10A so as not to lose insufflation when the camera 12 is removed from the robot 10. Several diameters are possible, but one implementation has a 5 mm camera that is inserted into a 6 mm lumen 10D in the robot, as is shown in FIG. 28A.

Figure 28B:
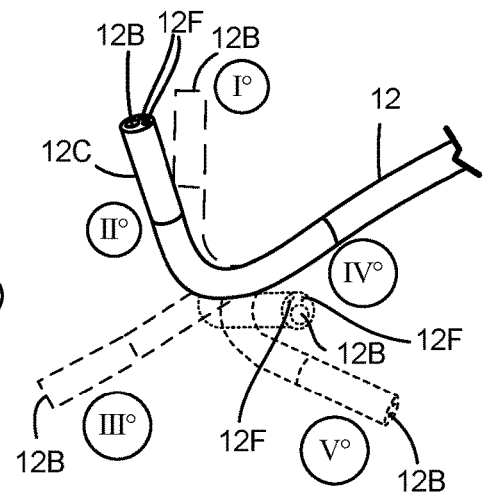
FIG. 28B is a close-up perspective view of the camera of FIG. 28A showing a variety of possible movements.
Figure 28I:
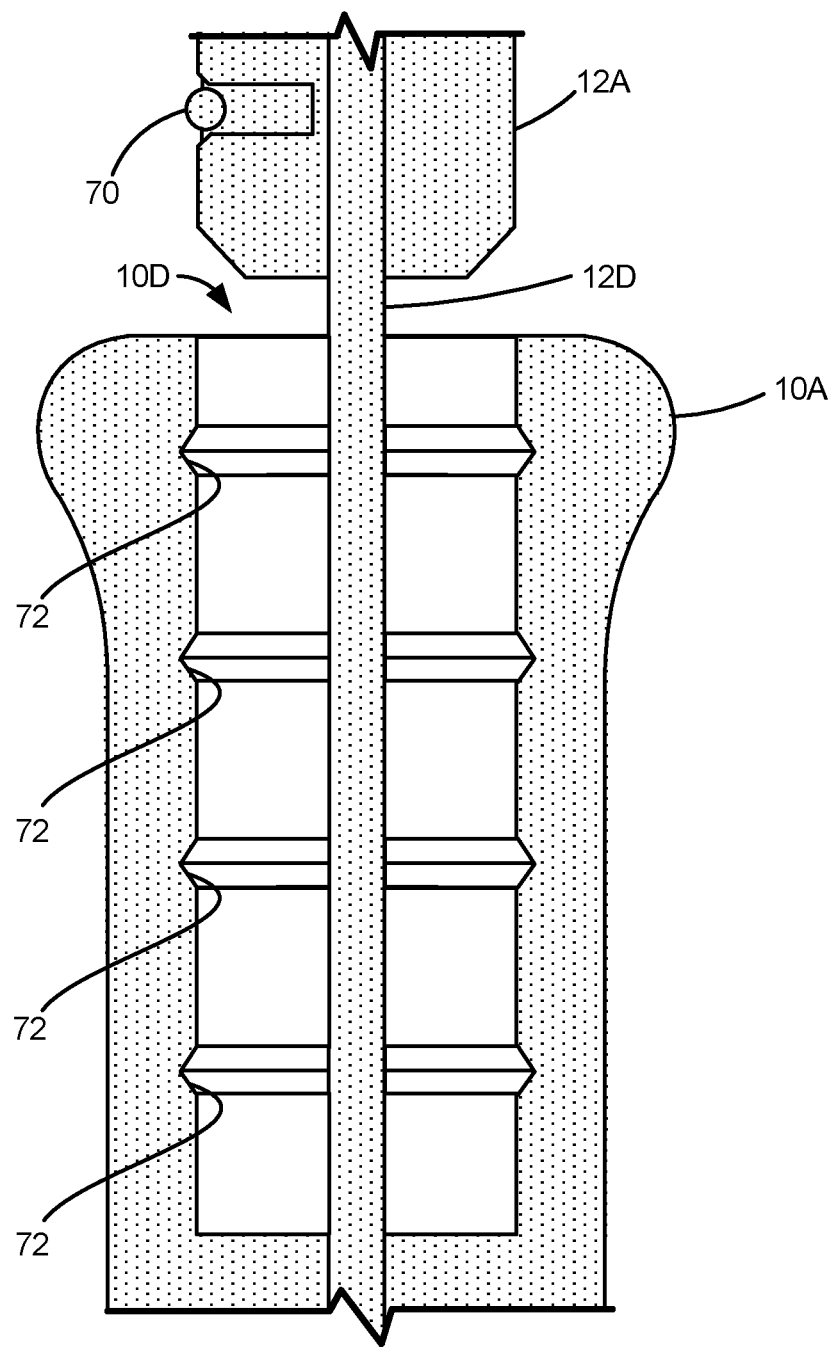
FIG. 28I is a cross-sectional view of the body lumen, according to one embodiment.

In the implementations of FIGS. 28A-B, the camera 12 is designed to flex in two independent degrees of freedom at the distal end 12C. This allows the user to visualize the robot tools at any position within the robot workspace via the imager 12B, as shown at I°-V° in FIG. 28B. In these implementations, the robot lumen 10D may be centered with respect to the robot body 10A, as shown in FIGS. 28A-B, allowing for symmetric points of view with respect to the robot arms, or it may be more anterior, as shown in the implementation of FIG. 1A, or posterior or in other locations.

Additionally, as shown in FIGS. 28A-28B the camera 12 tip 12C contains one or more lighting components 12F to light the viewing target (as discussed in relation to FIG. 1). In these implementations, the lighting components 12F can be illuminated via an independent light box or some other known light source (not shown, but one non-limiting example is high bright LEDs) in the camera handle or other forms of light sources. The light can then be directed through the camera shaft 12 via fiber optic cables, as has been previously described, for example in relation to U.S. patent application Ser. No. 15/227,813 filed Aug. 3, 2016 and entitled "Robotic Surgical Devices, Systems, and Related Methods," which is incorporated by reference.

An additional feature of certain implementations allows the camera 12 to be inserted into the body 10A with various depths. These implementations allow for better visualization during various activities. For example, FIGS. 28C-28E, 28F-28H and FIG. 28I show several implementations of a camera 12 that can be inserted at several depths, which can include fixed locations to hold the camera 12 using one ore more projections 70 such as spring balls 70 disposed on the exterior surface of the camera body 12A, and corresponding fixed ring detents 72 (best shown in FIG. 28I) disposed at a variety of depths inside the body lumen 10D. In use, the detents 72 that engage the balls 70 at various degrees of insertion depth (reference arrow H). This would allow the camera to be more proximal with respect to the robot arms (FIGS. 28C-E) or more distal with respect to the robot arms (FIG. 28F-28H). It is understood that in alternate implementations, other methods of disposing the camera 12 are possible, including a continuous movement and other systems actuated with various actuation and control mechanisms.

In various implementations of the camera handle 12, over molds may be provided for user comfort. Various connector and button and pigtail combinations are possible. In certain implementations, the camera handle 12A holds at least one motor to actuate the flexible tip 12C. In one version these motors can then be controlled via the surgeon console (as described below) or other input devices to control the motion of the camera 12. This control could also include other camera functions such as zoom, brightness, contrast, light intensity, and many other features.

Figure 29A:
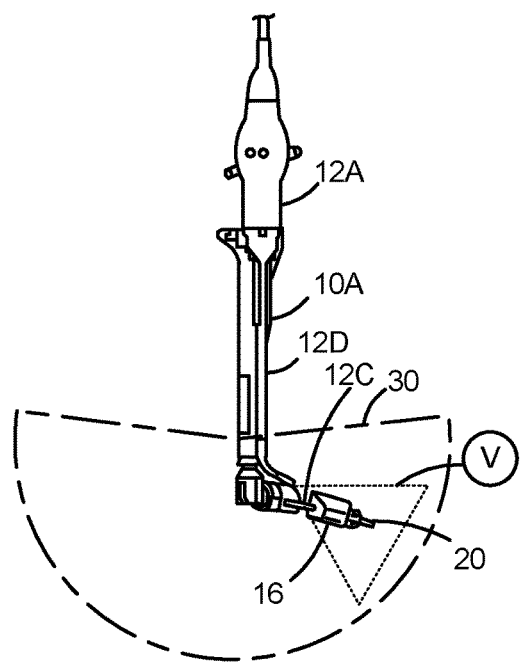
FIG. 29A depicts a surgical device workspace and field of view, according to exemplary implementation.
Figure 29B:
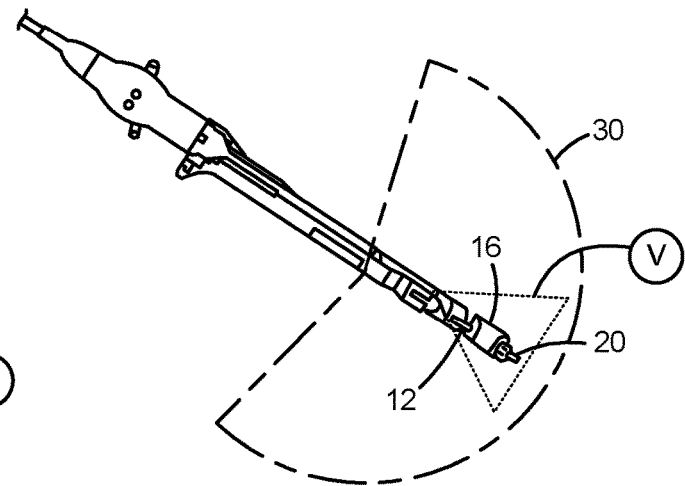
FIG. 29B depicts a surgical device workspace and field of view, according to another exemplary implementation.

As shown in FIGS. 29A-29B, the camera system's flexible articulated tip 12C allows the camera 12 to achieve fields of view (reference arrow V) over substantially all of the robot workspace 30. In these implementations, a cross section of one possible workspace in the sagittal plane is shown. FIGS. 29A-29B demonstrate the movement of the robot arms 14, 16 can move about a large workspace 30 and the camera system 12 must be able to visualize the robot tools 18, 20 at all times.

FIGS. 30A-33C depict several embodiments of the device 10, wherein the camera 12 is alternately oriented to allow for consistent tool visualization throughout the surgical theater. It is understood that this visualization requirement can be met through various implementations, and that many imager configurations are possible.

The imager 12B-1 of the implementations of FIGS. 30A-30F is referred to as a "zero degree scope" imager 12B-1, meaning that the line of viewing (shown with reference area V) is aligned normally with the distal tip 12C of the camera 12. FIGS. 30A-30F depict the sagittal plane of a robot 10 design with the camera 12C having a zero degree imager 12B-1 following the motion of the robot 10 from "behind" (at −90°) the robot 10 (FIG. 30A) to "bellow" (at 0°) the robot (at FIG. 30D) and in "front" (at 90°) of the robot 602 at FIG. 30F. FIGS. 30B, 30C and 30E depict the device 10 at −60°, −45°, and 45°, respectively. It is understood that in the implementation of FIGS. 30A-30F, the camera tip 12C is oriented so as to place the end effector 20 into the field of view V at each position.

The imager 12B-2 of the implementations of FIGS. 31A-31F is referred to as a "30 degree scope" imager 12B-2, meaning that the line of viewing (shown with reference area V) is aligned 30° from the distal tip 12C of the camera 12, as would be understood by one of skill in the art. FIGS. 31A-31F depict the sagittal plane of a robot 10 design with the camera 12C having a zero degree imager 12B following the motion of the robot 10 from "behind" (at −90°) the robot 10 (FIG. 31A) to "bellow" (at 0°) the robot (at FIG. 31D) and in "front" (at 90°) of the robot 602 at FIG. 31F. FIGS. 31B, 31C and 31E depict the device 10 at −60°, −45°, and 45°, respectively. It is understood that in the implementation of FIGS. 31A-31F, the camera tip 12C is oriented so as to place the end effector 20 into the field of view V at each position.

The imager 12B-3 of the implementations of FIGS. 32A-32F is referred to as a "60 degree scope" imager 12B-3, meaning that the line of viewing (shown with reference area V) is aligned 60° from the distal tip 12C of the camera 12, as would be understood by one of skill in the art. FIGS. 32A-32F depict the sagittal plane of a robot 10 design with the camera 12C having a zero degree imager 12B following the motion of the robot 10 from "behind" (at −90°) the robot 10 (FIG. 32A) to "bellow" (at 0°) the robot (at FIG. 32D) and in "front" (at 90°) of the robot 10 at FIG. 32F. FIGS. 32B, 32C and 32E depict the device 10 at −60°, −45°, and 45°, respectively. It is understood that in the implementation of FIGS. 32A-32F, the camera tip 12C is oriented so as to place the end effector 20 into the field of view V at each position.

FIGS. 33A-33B depict an alternate implementation of the robot 10 wherein the distal camera imager 12B and tip 12C can make an "S-curve" shape. This implementation may require an extra actuated degree of freedom in certain implementations, but it is understood that it has the ability to provide improved viewpoints (shown by reference area V) by allowing the camera 12B to be moved from the plane of (or otherwise being coaxial with) the robot arms 16 and end effectors 20. It is understood that there are various advantages to offsetting the camera tip 12C axis from any individual arm 14, 16 or end effector axis, such as to view various internal tissues, organs and the like within the surgical theater.

Figure 34A:
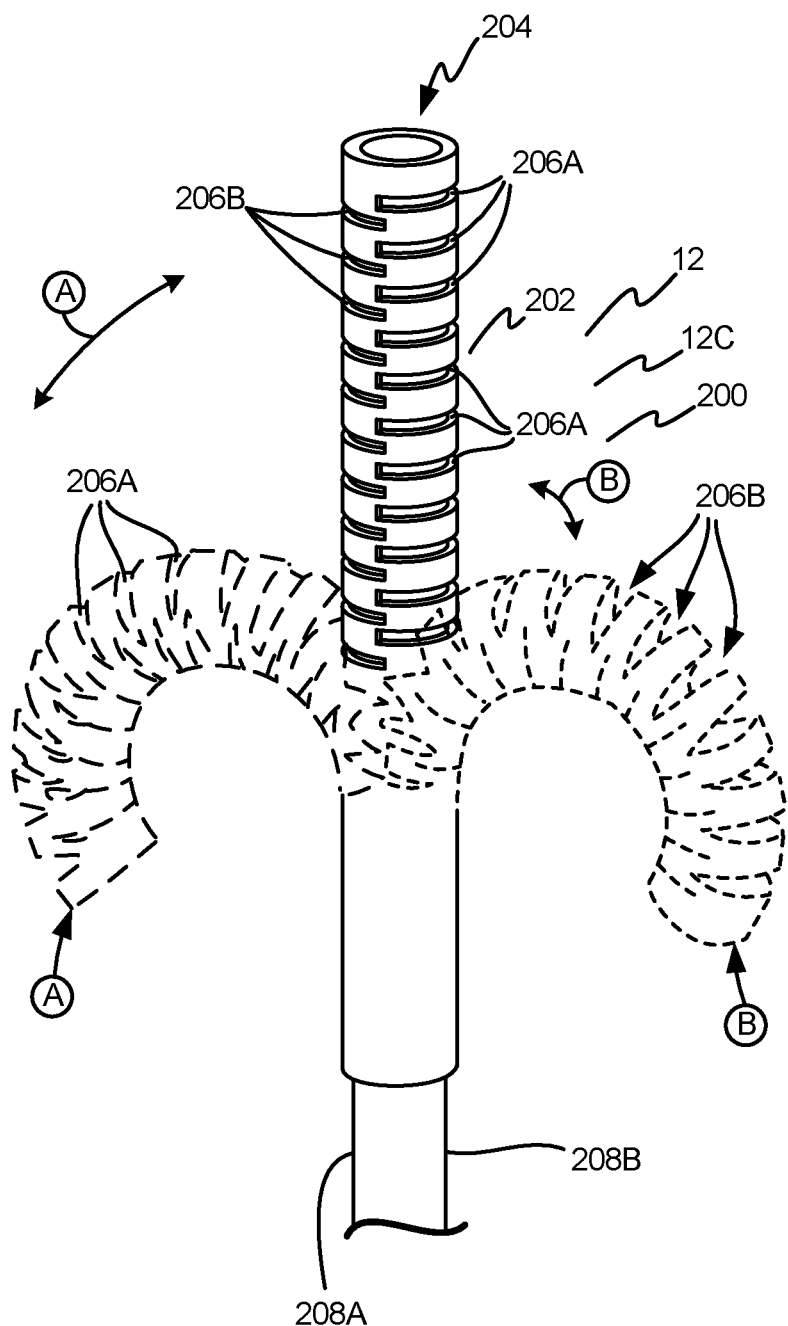
FIG. 34A is one implementation of the articulating camera tip.
Figure 34B:
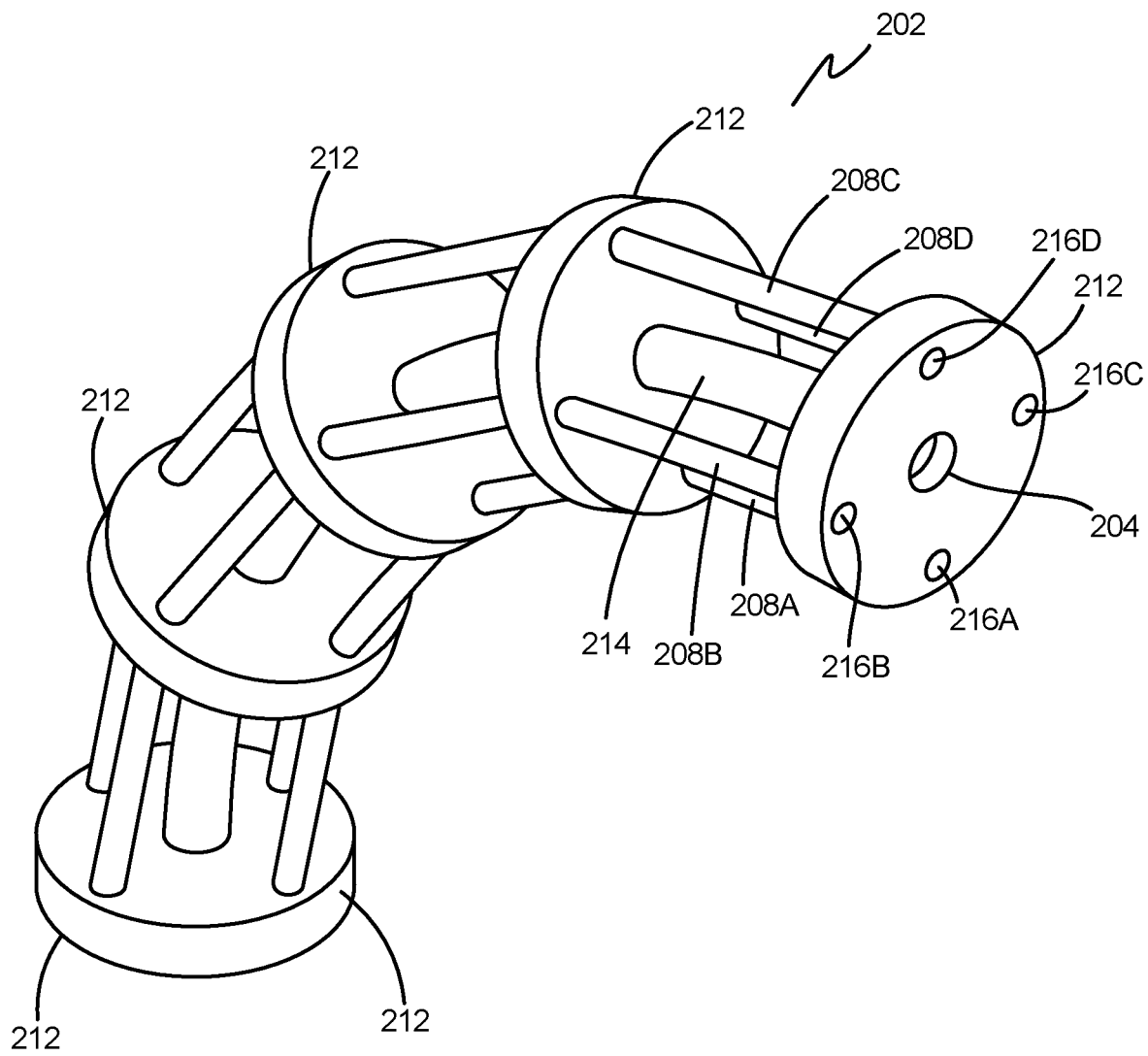
FIG. 34B is another implementation of the articulating camera tip.
Figure 34C:
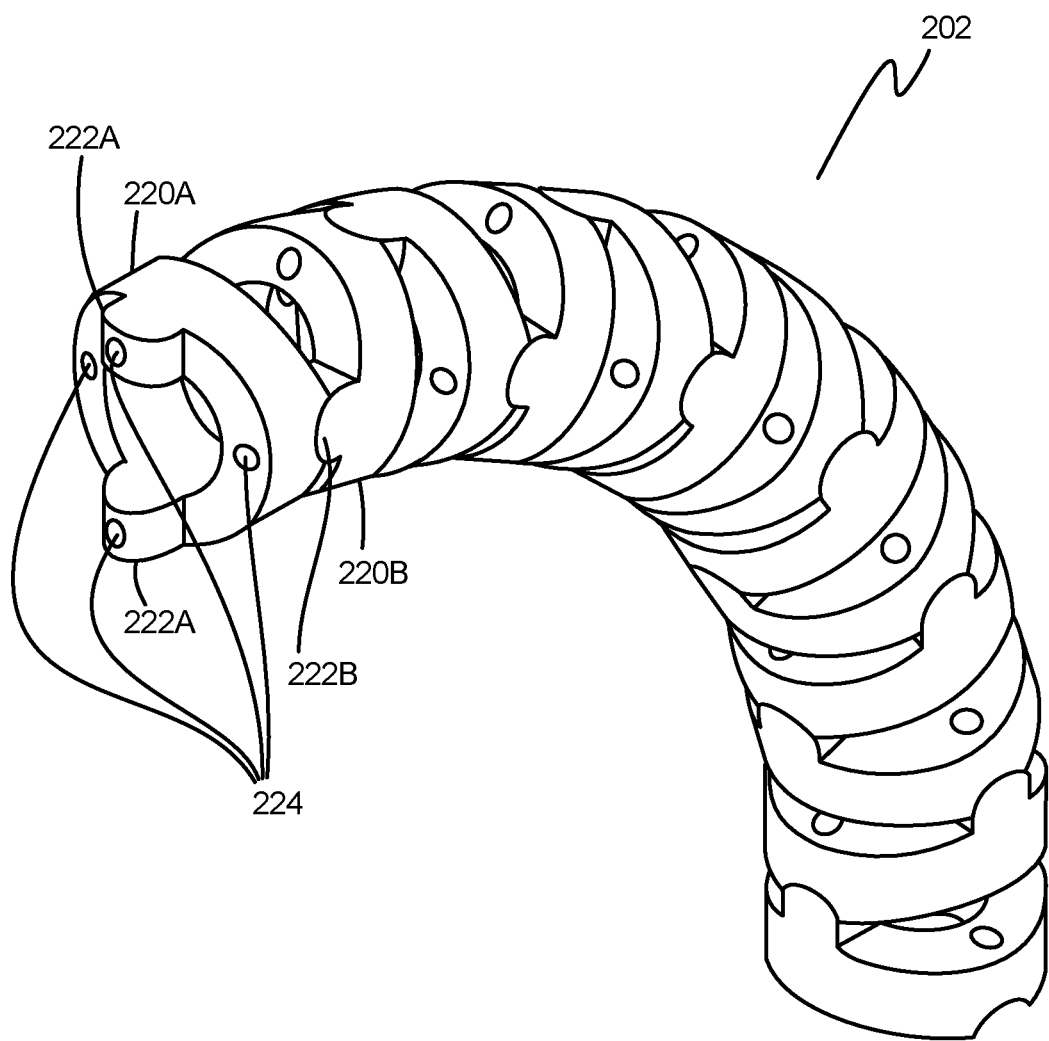
FIG. 34C is yet another implementation of the articulating camera tip.

Turning to the articulation of the camera tip 12C, FIGS. 34A-34C depict various internal components and devices used to achieve the camera 12 movements shown in FIGS. 31A-33B and elsewhere. Again, because of the large workspaces possible in certain implementations (as discussed for example in relation to FIGS. 6A-6B at 30) exemplary implementations of the camera 12 are configured or otherwise constructed and arranged to allow for both pitch (meaning "up" and "down") movements and pan or yaw (meaning "side to side" movements) within the workspace 30. In these implementations of the system, the camera is therefore able to allow the user to observe the device arms and end effectors throughout the expanded workspace. Several devices, systems and methods allowing for this improved range of vision and camera movement are described herein. As would be understood by one of skill in the art, the present examples are non-limiting, and are shown for purposes of illustration without the protective sheath (shown, for example, in FIG. 9A at 15).

The pitch and yaw articulation of the camera tip 12C can be achieved through various implementations, as shown in FIGS. 34A-34C. FIGS. 34A-34B show continuum mechanisms. In the implementation of FIG. 34A, the camera is able to articulate at the tip 12C. In this implementation, the camera tip 12C via an articulating portion 202 defining a camera lumen 204 and comprising a plurality of openings 206A, 206B on either side of the portion so as to allow the device to flex in the possible directions (as shown by reference arrows A and B. It is understood that in these implementations, the articulating portion 202 can be caused to move or articulate in either direction (A or B) via cables 208A, 208B disposed through the camera lumen 204 and actuated via motors disposed within the camera handle 12A. It is further understood that additional components such as wires, fiber optics and the like can also be disposed through this lumen 204.

In the implementation of FIG. 34B, the articulating portion has several spacers 212 surrounding an internal tube 214 defining a camera lumen 204. In these implemenations, a plurality of cables 208A, 208B, 208C, 208D are disposed through openings 216A, 216B, 216C, 216D in the spacers 212. As would be appreciated by one of skill in the art, in these implementations the cables are fixedly attached to the most distal spacer 212 and are allowed to pass through the more proximal spacers, such that proximal movement of the cables 208 results in articulation of the portion 202. Various methods for urging the cables 208 proximally have been previously described, for example in relation to U.S. patent application Ser. No. 15/227,813 filed Aug. 3, 2016 and entitled "Robotic Surgical Devices, Systems, and Related Methods," which is incorporated by reference.

The implementation of FIG. 34C has a "stack" of interlocking linkages 220 disposed within the portion 202. In these implementations, the linkages 220 have corresponding vertical 222A and horizontal 222B articulating links on adjacent links 220A, 220B that are configured to allow the proper degrees of freedom, as would be understood and appreciated by one of skill in the art. In these implementations, cables (not shown) can be run through openings 224 in the links 222, as has been previously described. It is understood that these various implementations of the articulating portion allow for the adjustment of camera pitch and yaw in various degrees of freedom so as to enable the camera to view several fields of view within the workspace without repositioning the camera body or device.

Further, the depth to which the camera 12 is inserted into the device 10 can be varied. FIGS. 35A-C show how the depths of the camera 12 can be varied to change the vantage point (reference arrow V). For example, as shown in FIG. 35A, the camera 12 can be fully inserted into the robot 10A with the imager 12B coaxial with the lumen 10D during insertion to "self visualize" the insertion process. In use, self visualization allows the user to view the tool tips during insertion. When in this "insertion" position, the imager 12B reaches the maximum distance from the "plunge line" 230 (shown by reference arrow A).

As shown in FIGS. 35B-35C, a forward working position (FIG. 35B) and a backward working position (FIG. 35C) are also possible, with the field of view (reference area V) adjusted correspondingly. In the depicted implementation, the camera 12 motion can be manual or motorized and controlled. As is also shown in FIGS. 35B-35C, in certain implementations of the device 10 where the camera extends from a portion on the front side of the device (like that shown in FIG. 1A), the camera tip depth will vary between frontward and backward viewing positions, as is designated by reference arrow B. In certain implementations, and as is also described in relation to FIGS. 28A-I, the height of the camera 12 within the workspace can also be adjusted to correct for this discrepancy.

Various implementations of the system have a variety of tools, or end effectors 18, 20 disposed at the distal ends of the arms. Exemplary implementations feature interchangeable end effectors or "hands". In these implementations, the robot "hands" can include various tools such as scissors, graspers, needle drivers, and the like. In various implementations, the tools are designed to be removable by a small twist of the tool knob 250, such as via a ¼ turn bayonet connection. The tools generally have two actuated and controlled degrees of freedom with respect to the forearm. It is understood that in various implementations, the tools can also have no degrees of freedom or one or more degrees of freedom. In various implementations, the tools are controlled via the user input devices on the control console, as has been previously described. The first degree of freedom allows the tools to roll about their own axis (shown at reference arrow R). One type of tool used in this robot has one degree of freedom. This tool 18, 20, shown in FIG. 36A-B, is based on hook cautery from manual laparoscopic tools, and has a roll interface 252 and monopolar slip ring 254. Certain implementations of the tool 18, 20 can roll (reference arrow R), but does not have an open close function. Many additional end effector implementations are contemplated herein, as are described in the several incorporated references.

In use, according to certain implementations, the distal end 10B of the device body 10A and arms 14, 16 are disposed within the patient body cavity, so as to be operated remotely by the user via console, as is described below. The user—typically a surgeon—positions the device 10 body within the cavity at a fixed initial starting position, and in some implementations, is thereafter able to re-position the device as desired. In certain implementations, and as described herein, the various support systems described herein utilize "remote center" or "point tracing" approaches to maintain the desired position and orientation of the robot relative to a specific point through re-positioning, such as a remote point and/or the incision or insertion point. In certain implementations, the remote centering is maintained by constraining the movements of the support structure as it moves through several degrees of freedom, while certain point tracing implementations impose additional movements onto the support structure to maintain the position. It is understood that certain implementations can involve combinations of these and other approaches. Several illustrative systems and methods for securing, positioning and repositioning the device 10 are described herein.

Figure 37:
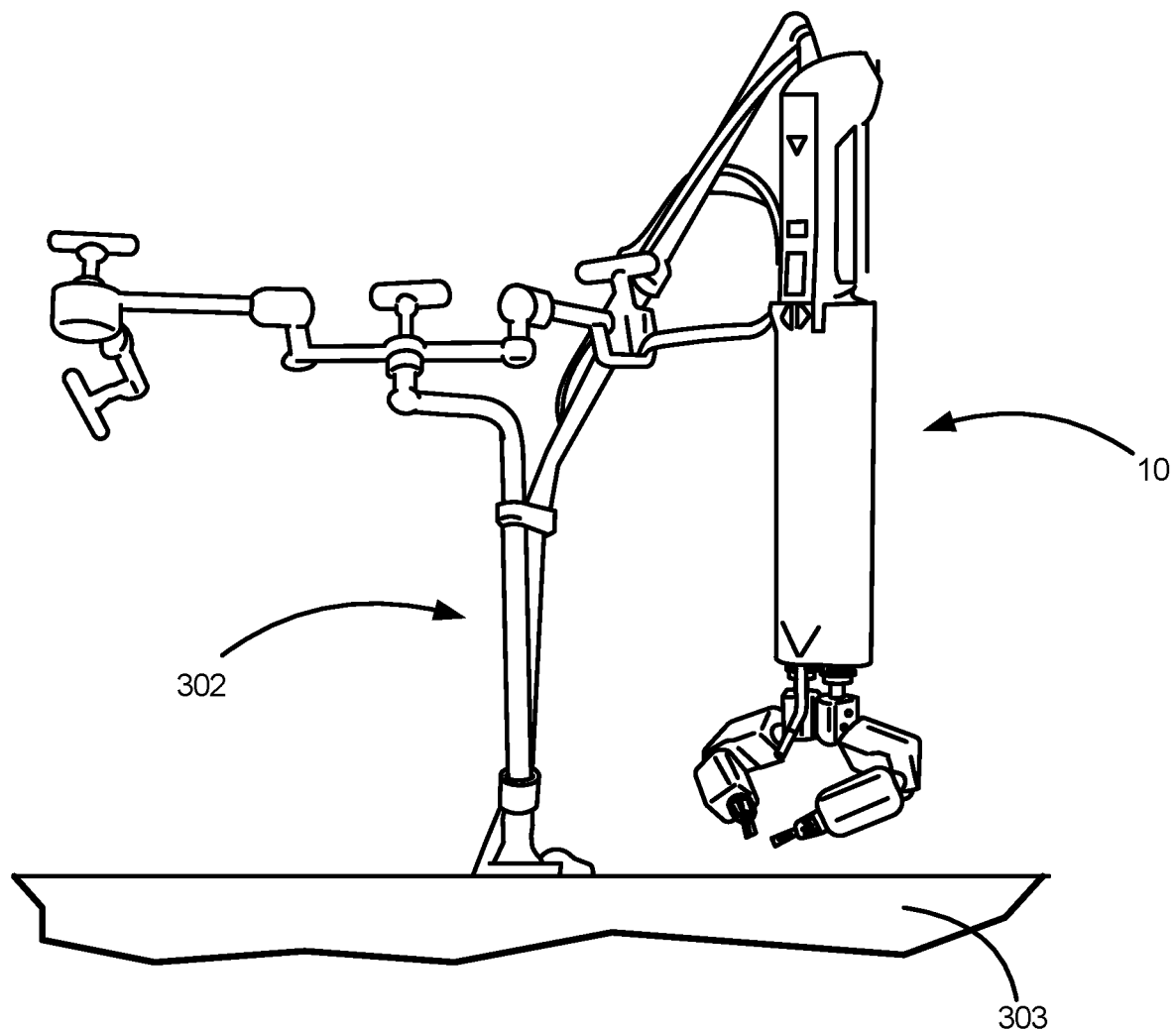
FIG. 37 is a front view of the surgical device on a support structure, according to one implementation.

As shown in FIG. 37, in various implementations the robot 10 can be supported in place with FIG. 37 shows one method or device for supporting the robot 10 with a known clamp/support system 302 attached to the operating room table 303. The clamp system 302 allows for significant adjustment of the location of the robot in all six degrees of freedom possible for the robot body. It is understood that other known, commercially-available support systems can be used to hold any robotic device embodiment disclosed or contemplated herein (such as, for example, robot 10). Such known devices typically hold manual laparoscopic instruments such as scopes, tools, and retractors, and can similarly be used to clamp to or otherwise support the robot 10 or other such robotic device embodiments.

Figure 38:
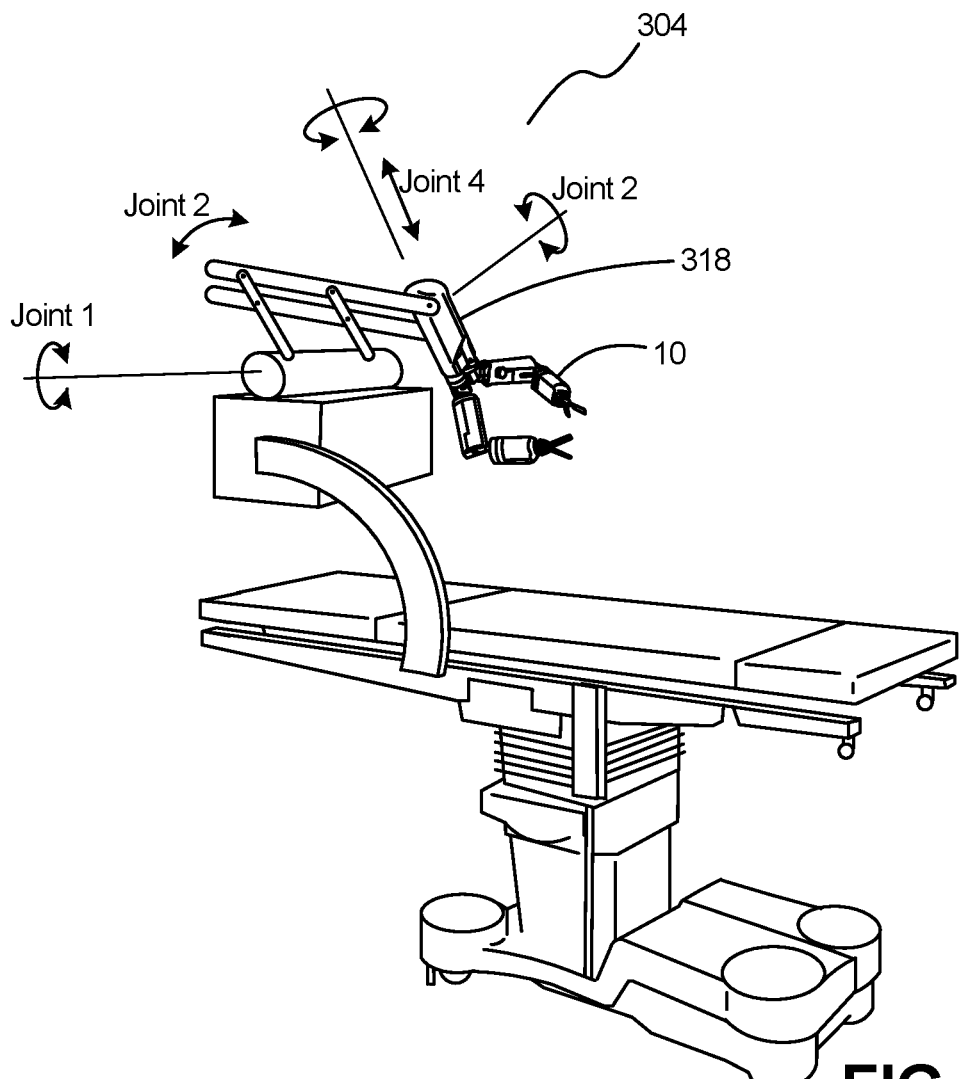
FIG. 38 is a perspective view of the surgical device on a support structure, according to one implementation.
Figure 39:
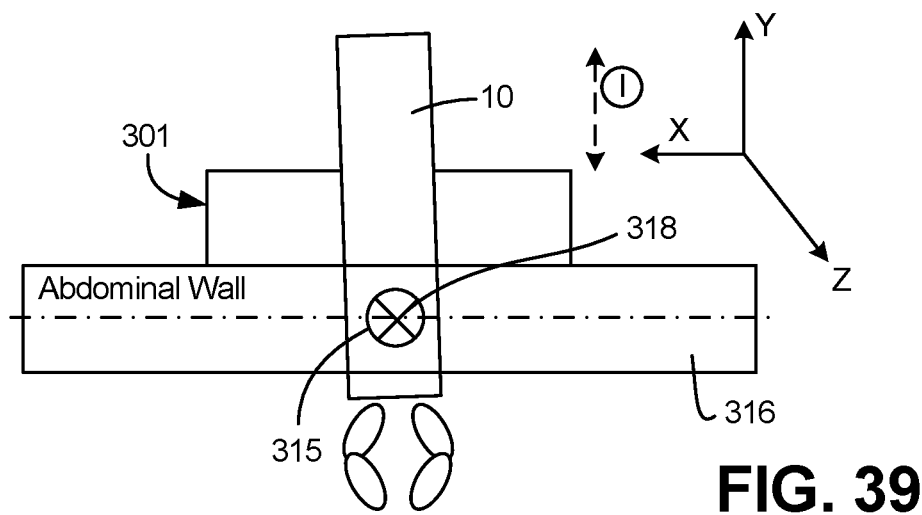
FIG. 39 is a cross-sectional view of the surgical device at the insertion point, according to one implementation.

FIGS. 38-39 show one embodiment of a remote center mechanism 304, sometimes called a "point tracing mechanism," or "positioning system" that could be used to support the robot 10. One advantage of the remote center mechanism 304, in accordance with one implementation, is that the mechanism 304 can be used to move the device 10 while a single point of the robot 10 assembly remains in the same location: the remote center 318 of the mechanism 304 as best shown in FIG. 38. In use, the mechanism 304 is typically positioned such that the remote center 318 is positioned at the insertion point 315 in the patient, as best shown in FIG. 39. With the remote center 318 at the insertion point 315, the robot 10 has about three degrees of freedom about this insertion point 318 and one in/out translation through the insertion point 315 and port 301. In these implementations, the insertion point 315 can be adjusted in several ways such as by moving the mechanism 304 with respect to the operating room bed rail to align the remote center 318 with the insertion point 315 on the patient. The remote center 318 results, in one embodiment, from all joints of the mechanism 304 (shown at Joint 1, 2, 3, & 4 in FIG. 38), being designed to intersect with that remote center 318. As shown in FIG. 38 according to one implementation, joints 1-3 are rotational joints (in which Joint 2 is a special parallelogram mechanism) and joint 4 is a translational joint that controls the robot insertion depth into the abdominal cavity. According to any remote center mechanism implementation as disclosed or contemplated herein, the remote center 318 can eliminate or reduce mechanical interference between the robot 10 and the abdominal wall 316 that might be created when the robot 10 is being moved.

Figure 40A:
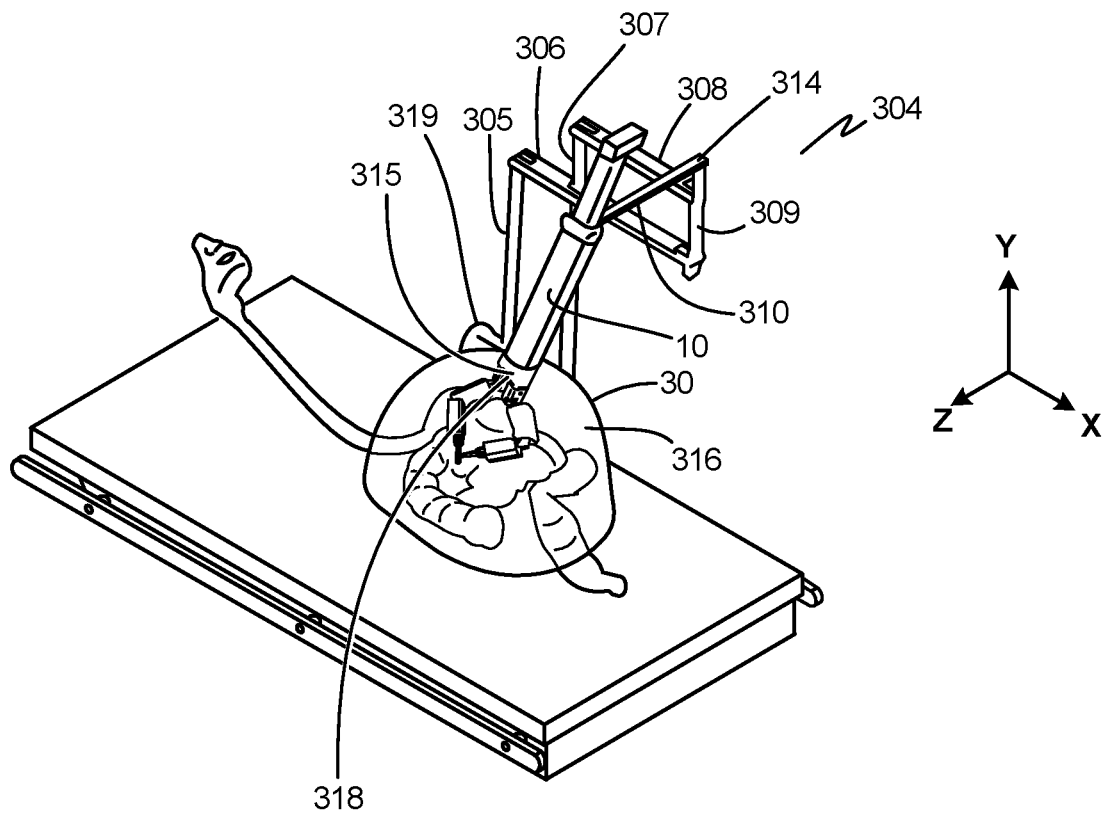
FIG. 40A is a perspective view of the surgical device on a support structure, according to one implementation.
Figure 40B:
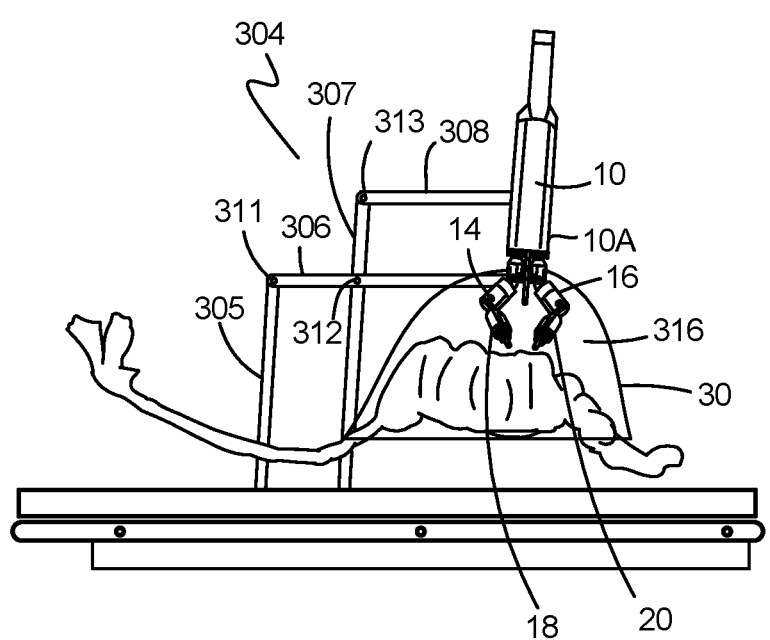
FIG. 40B is a side view of the surgical device on a support structure, according to one implementation.

FIGS. 40A and 40B show the positioning of the robot 10 with respect to the abdominal wall 316, according to certain implementations. In these implementations, a remote center positioning device 304 (and any other positioning device embodiment disclosed or contemplated herein) allow the robotic device 10 to access the full extent of the workspace 30 within the cavity 316. In these implementations, the positioning device 304 has several linkages and links 305, 306, 307, 308, 309 including a support link 310 in mechanical communication with the device 10 and joints 311, 312, 313 including a support joint 314 in mechanical communication with the support link 310. In these implementations, the links 305, 306, 307, 308, 309, 310 and joints 311, 312, 313, 314 are in mechanical communication with one another and with a support pivot 319, so as to be capable of movement in at least three degrees of freedom, and with the rotation of the device 10, a fourth degree of freedom.

That is, the positioning device 304 makes it possible to position the robotic device 10 within the patient's cavity 316 with the body 10A of the device 10 positioned through the incision 315 (or port disposed in the incision 315) such that the end effectors 18, 20 attached to the arms 14, 16 of the robotic device 10 can reach any desired location in the workspace 30 while the links 305, 306, 307, 308, 309, 310 and joints 311, 312, 313, 314 of the positioning device 304 function to create the remote center 318 where the device body 10A passes through the incision 315 such that all movements of the robotic device 22 pass through the remote center 318 at a single point, such as the insertion point 315. In other words, regardless of the positioning of the links 305, 306, 307, 308, 309, 310 and joints 311, 312, 313, 314 and the resulting positioning of the robotic device 10 within the patient's cavity 316, the portion of the device body 10A at the incision 315 (the remote center 318) remains in the same position in all three axes (through the incision 315) as a result of the positioning device 304. This allows operation of a robotic device (such as robotic device 10) within a cavity (such as cavity 316) such that the end effectors (such as end effectors 18, 20) can reach any desired location within the cavity while the entire device 10 is connected to the positioning device 304 via a device body 10A that passes through and never moves from a single point (remote center 318) at the incision 315, thereby making it possible to operate and position the device 10 through that single incision (such as incision 315). Another advantage is that the positioning device 304 makes it possible to use the single in vivo robotic device within the patient's cavity instead of the multiple arms of the known Da Vinci™ system extending from the patient's cavity and thereby taking up a great deal of workspace outside the body of the patient.

Figure 41B:
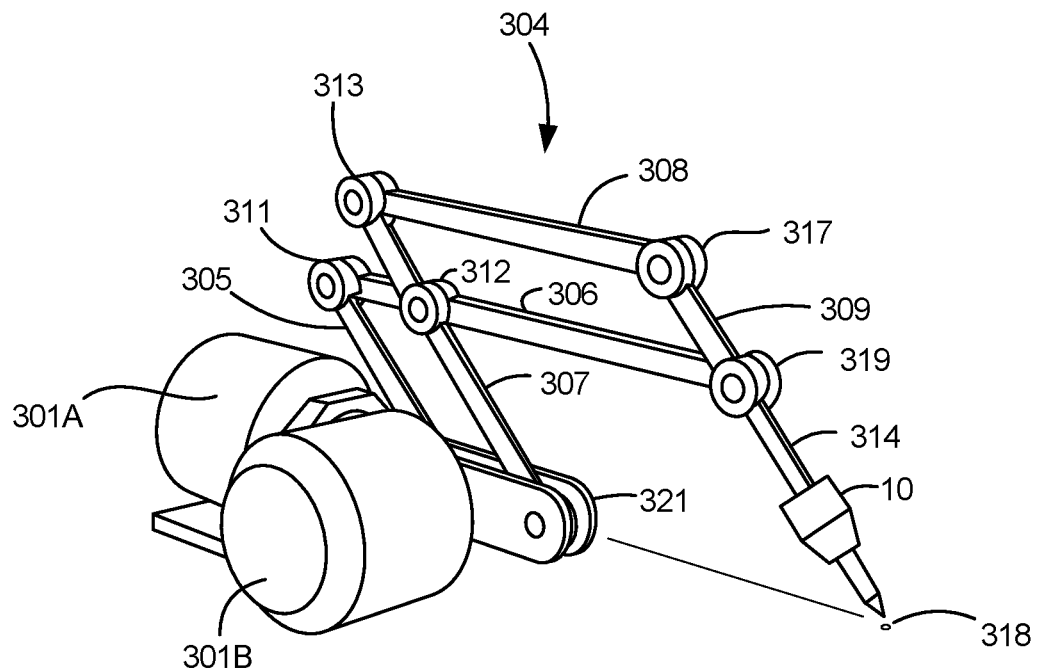
FIG. 41B is a further perspective view of the surgical device on a support structure, according to the implementation of FIG. 41A.
Figure 41B:
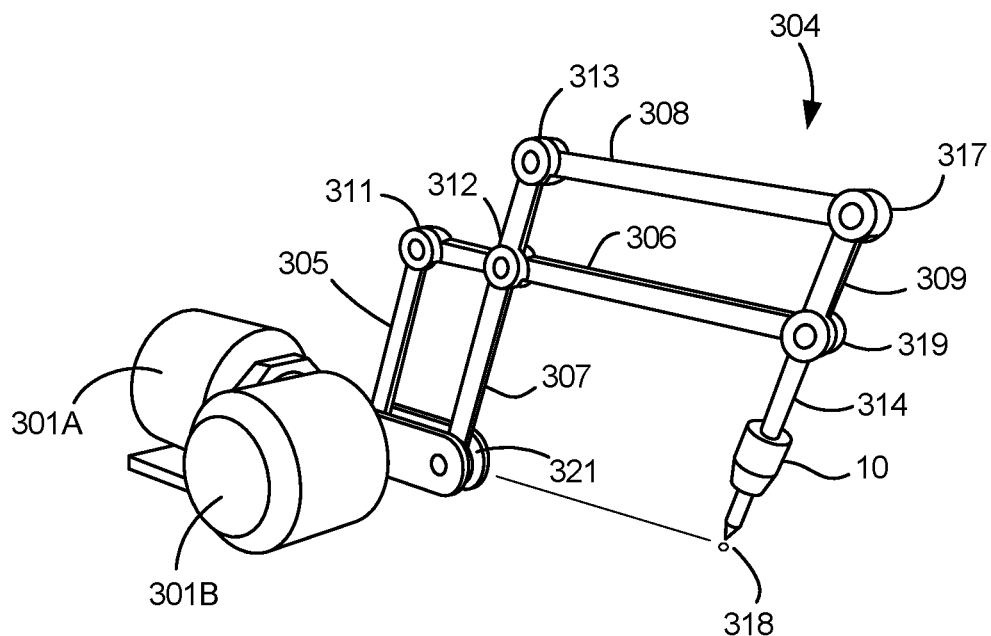

FIGS. 41A and 41B show further implementations of the support device 304 that can be used to support the robot 10. In these implementations, one or more motors 301A, 301B can be operationally integrated with a support mechanism 304 such that the links 305, 306, 307, 308, 309, 310 and joints 311, 312, 313, 314. It is understood that in these implementations, the motors 301A, 301B are able to drive the linkages into various controlled positions, that is to "point trace" on the incision point 318 through three or four (including device roll) degrees of freedom. That is, the actuators or motors 301A, 301B can be configured to drive the links 305, 306, 307, 308, 309, 310 and joints 311, 312, 313, 314 in a coordinated fashion through yaw, pitch and rotational degrees of freedom, so as to maintain the position the robot 10 relative to the remote point 318.

Figure 42A:
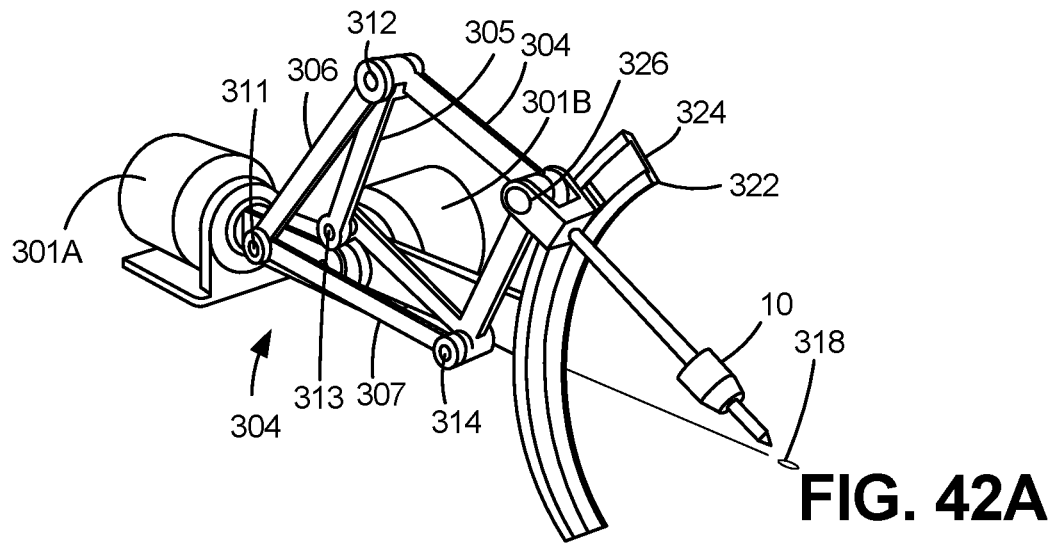
FIG. 42A is a perspective view of the surgical device on another support structure, according to one implementation.
Figure 42B:
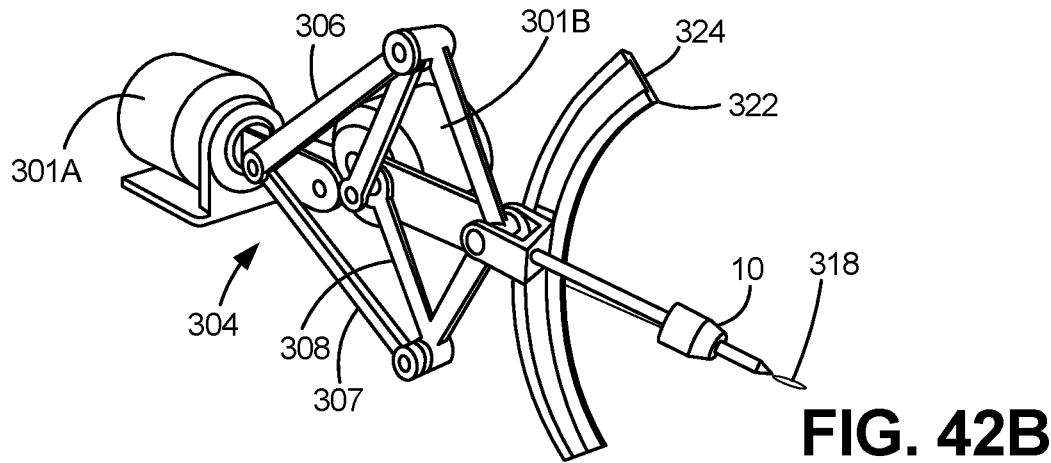
FIG. 42B is a further perspective view of the surgical device on a support structure, according to the implementation of FIG. 42A.
Figure 42C:
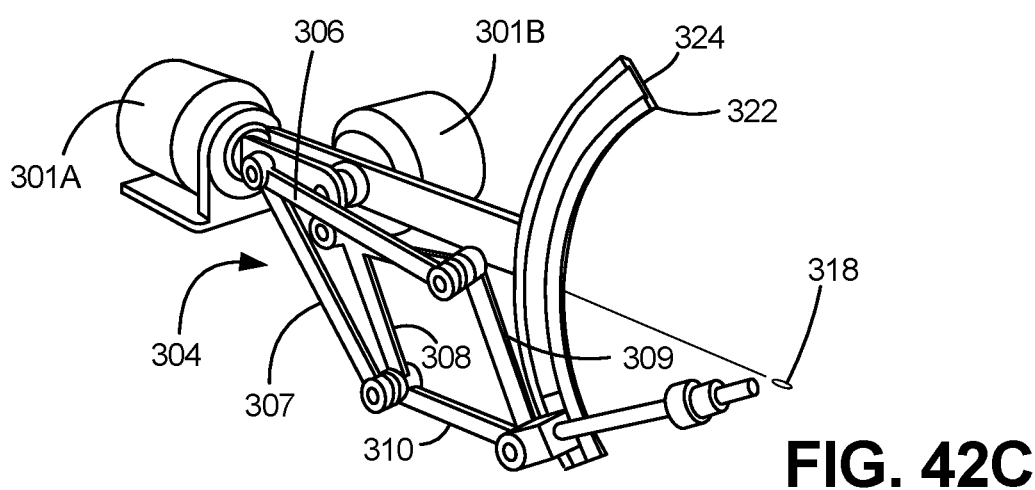
FIG. 42C is yet a further perspective view of the surgical device on a support structure, according to the implementation of FIG. 42A.

The support structure 304 of FIGS. 42A-42C also utilizes one or more motors 301A, 301B to maintain the position of the device 10 relative to the remote point 318, according to certain implementations. Again, in these implementations, the support structure 304 has links 305, 306, 307, 308, 309, 310 and joints 311, 312, 313, 314, includinng a tracked joint 326 that is in operational communication with a pitch track 322 having a track opening 324. It is understood that in these implementations, the movement of the links 305, 306, 307, 308, 309, 310 urges the support joint 326 through various positions on the track opening 324 to reposition the device 10 while point tracing at the remote point 318. It is understood that many implementations of the linkages and/or joints are possible.

Figure 43:
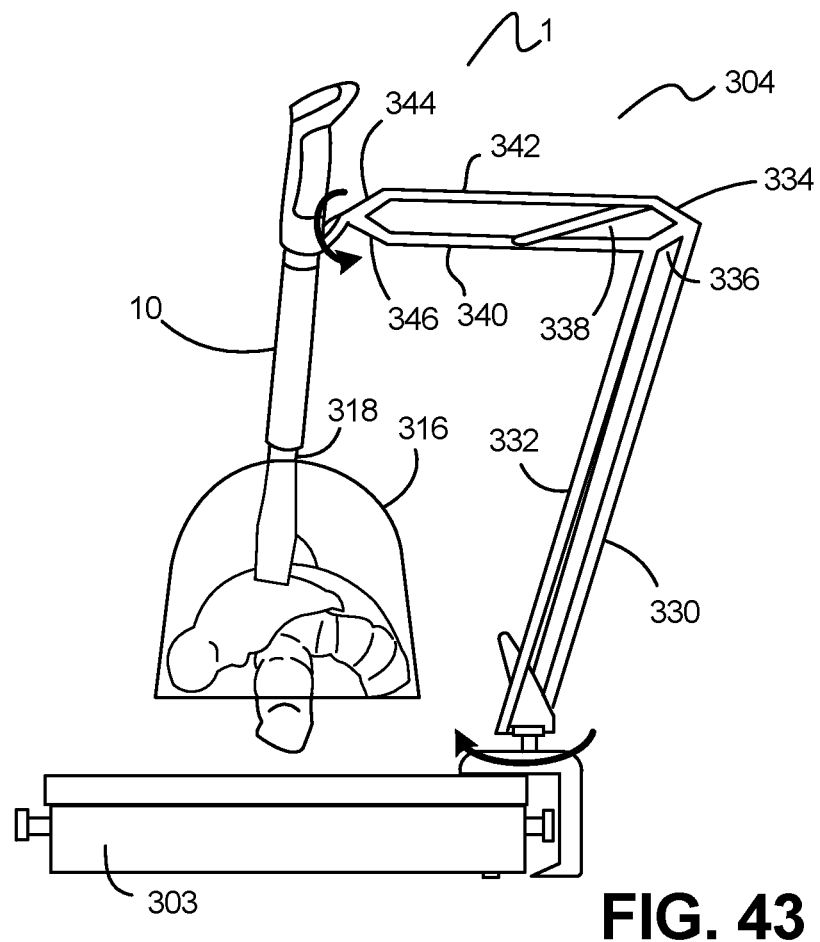
FIG. 43 is a side view of the surgical device on yet another support structure, according to one implementation.
Figure 44:
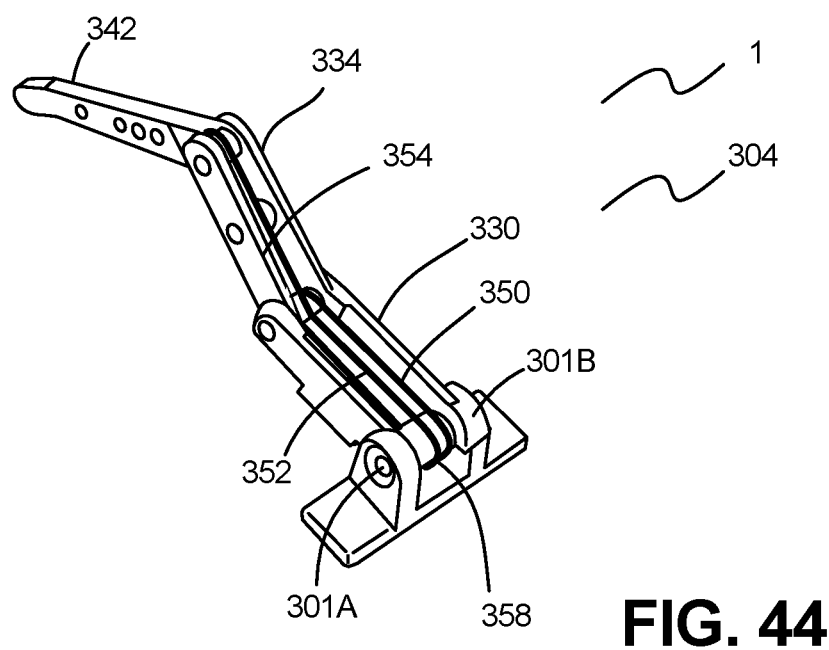
FIG. 44 is yet a further perspective view of the surgical device on a support structure, according to another implementation.

The implementations of FIGS. 43 and 44 depict a positioning and support structure embodiment referred to as the "desk lamp" 304. It is understood that this implementation has similar kinematics to a desk lamp, in that in these implementations, the links 330, 332, 334, 336, 338, 340, 342, 344, 346 are able to move in a controlled fashion relative to the handle 12A and/or robot 10, so as to adjust the pitch or other position of the robot 10 while maintaining a consistent position relative to the insertion point 318. In certain implementations, springs can be used to counterbalance the weight of the robot 10. As shown in FIG. 44, in certain of these support devices 304, a plurality of cables 350, 352, 354 can be used to drive the linkages, such as via an actuated spindle 360 or other device. That is, various implementations, actuators 301A, 301B can be operationally connected to a cables 350, 352, 354 to drive these motions of the links 330, 332, 334, 336, 338, 340, 342, 344, 346.

Of course all of the support mechanisms described herein can be actuated with electric motors or other actuators. Each joint, or any combination of the joints, could be driven by an electric motor. Sensors could also be used at some or all of the joints to create a control system. This control system can then be connected to the robot control system so that the support mechanism control and the robot control could be coordinated to allow both systems to work together so as to extend the workspace of the robotic device through the robot controls (or other controls) on the console or in a separate control system.

As shown in FIG. 45, in further alternate implementations, the robotic device 10 can be supported by an exterior robot 360. Here, the robotic device 10 is supported by an external robot arm 362 having several links 362, 364, 366 that have one or more degrees of freedom each, and can be used to remote center or point trace the robot during the surgical procedure. In various implementations, the arm(s) are actively controlled by motors, sensors, and a control system, such as that described herein. It is understood that this external robot 360 in certain implementations can be another surgical robot 360, an industrial robot, or a custom robot. It is further understood that the external robot 360 in this system 1 could be used in conjunction with other surgical devices and robotic surgical systems, such as laparoscopes 3365 or other known surgical tools and devices. Another version of the external robot support robot 360 could be a parallel linkage external robot 370, as is shown in the implementation of FIG. 46.

The parallel linkage external robot 370 of FIG. 46 has an above-mounted robot 370 that in certain implementations is mounted to the ceiling above the surgical theater. In various implementations, a plurality of radially-disposed proximal links 372 that are actuated by the robot 370 viat actuation joints 371. These proximal links 372 are in mechanical communication with corresponding joints 374 that are in turn supporting or otherwise positioning support arms 376. In these implementations, the support arms are in mechanical and/or operational communication with the surgical robot 10 by way of a support joint 378, such that the movement of the actuation joints 371 is sufficient to urge the support joint laterally, rotationally and/or vertically so as to urge the robot 10 into various additional positions.

FIG. 47 depicts a further alternative embodiment using a ball-like joint 380 supported by a support bar 382 to provide adequate degrees of freedom to the robot 10 near the insertion point 318. In this implementation, the ball-like joint can be used to adjust the three rotations and one translation (in/out) of the robot 10, as would be understood by one of skill. It is further understood that in certain implementations, a lever lock could be used to unclamp the ball and allow all four degrees of freedom to move.

As shown in FIGS. 48A-48D-2, in further alternate implementations, a "hangman" support structure 400 is used to support the robot 10. In this implementation, a curved, pivoting support staff 402 is attached to the operating room table 303 and extends above the patient cavity 316. In this implementation, the support staff 404 is in operational communication with a suspended, articulating "J-hook" 404 that extends over the patient. In this implementation, the J-hook has an additional telescoping link 406 withball joints 408, 410 at either end and is used to support and position the robot 10. In various implementations, and as shown in FIGS. 48B-1 through 48D-2, rotational movement of the support staff causes corresponding movement of the J-hook 404 and associated link 406 and joints 408, 410 so as to "swing" the hangman 400 and, in turn, the device 10 about a central position 318. It is understood that many alternate constructions are possible.

Figure 49:
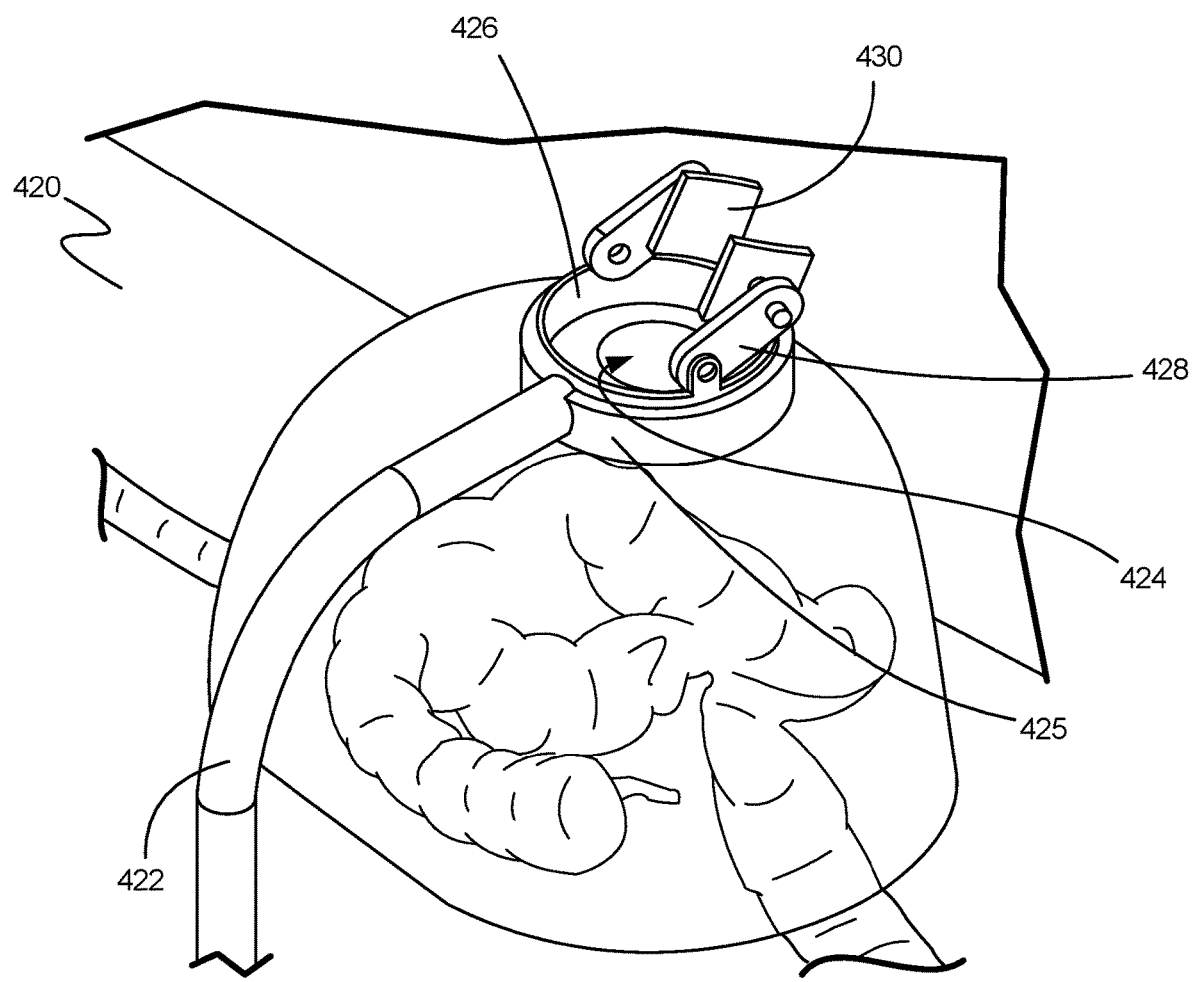
FIG. 49 is a perspective view of a support structure positioning the surgical device, according to one implementation.

FIG. 49 shows a further alternate implementation showing a rotating support (also referred to as a "Lazy Susan support") 420 for the robot. In these implementations, the robot (not shown) is supported by a support arm 422 (similar to FIG. 37, for example) that allows for positioning or adjustment of the support 420 in relation to the insertion point 424 in the patient. That is, a support ring 425 is coupled to a distal end of the support arm 422 and can be positioned adjacent to or on the insertion point 424 of the patient. As is understood in the art, the insertion point 424 can be an incision or a natural orifice in the patient. The support 420 has a "yaw" degree of freedom in the form of a rotational ring 426 that is rotatable in relation to the support ring 425 around the insertion point 424. Further, the support 420 has a "pitch" degree of freedom by way of the cross-links 428 that are rotatable around an axis that is transverse to the axis of the rotatable ring 426. Coupling plates 430 are rotatably attached to the cross-links 428 and are configured to couple to the sides of a robotic device (such as, for example, device 10). According to one implementation, the coupling plates 430 can be any coupling components capable of coupling to a robotic device. The robot (not shown) can be inserted at different depths using the plates 430, which are attached to the cross-links 428 with a passive joint that allows for errors in acting about the insertion point 424 introduced by variations in the abdominal wall thickness. More specifically, each of the cross-links 428 are rotatably coupled at one end to the rotational ring 426 and rotatably coupled at the other end to the plates 430, thereby making it possible for the robot (such as robot 10) to be moveable so as to address any unknown abdominal wall thickness. In one embodiment, the cross-links 428 can be any elongate members that can be rotatably coupled to the rotational ring 426 and the coupling plates 430.

Figure 50A:
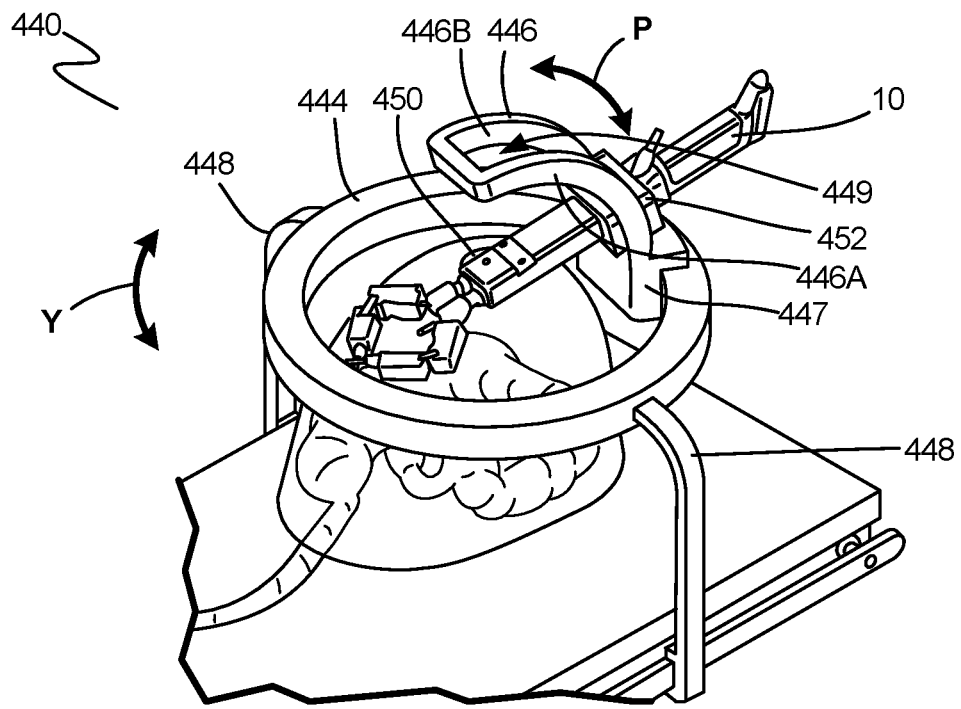
FIG. 50A is a perspective view of another support structure positioning the surgical device, according to one implementation.
Figure 50B:
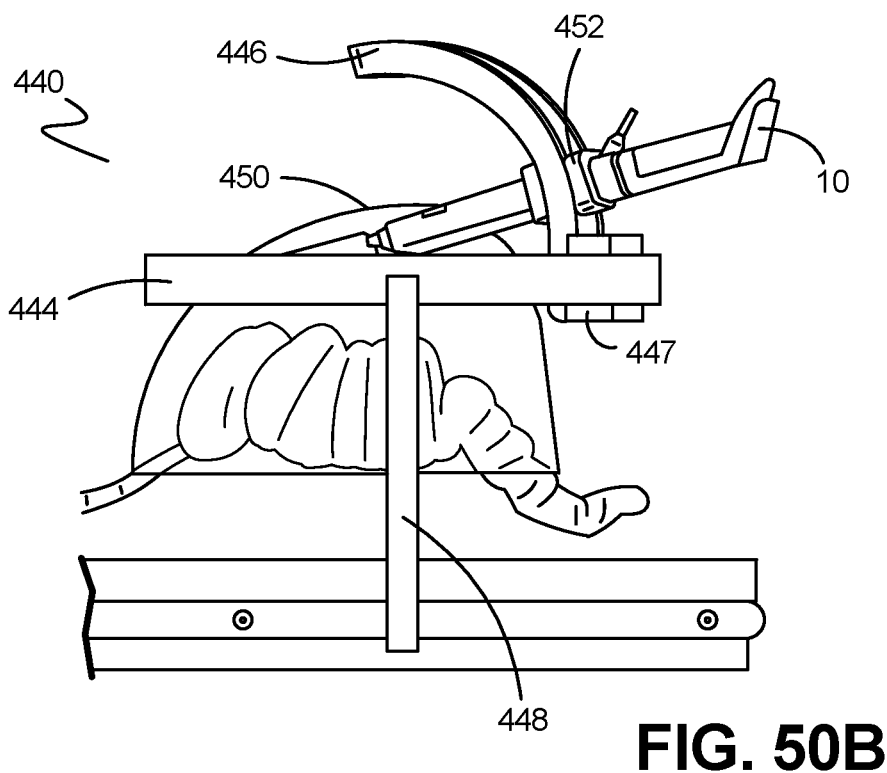
FIG. 50B is a side view of another support structure positioning the surgical device, according to one implementation.
Figure 50C:
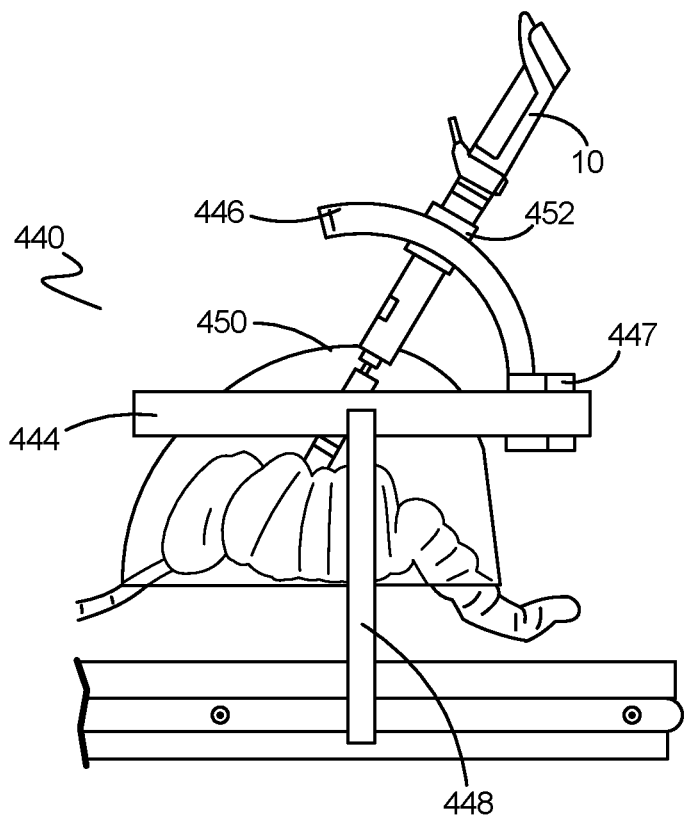
FIG. 50C is a side view of another support structure positioning the surgical device, according to one implementation.
Figure 50D:
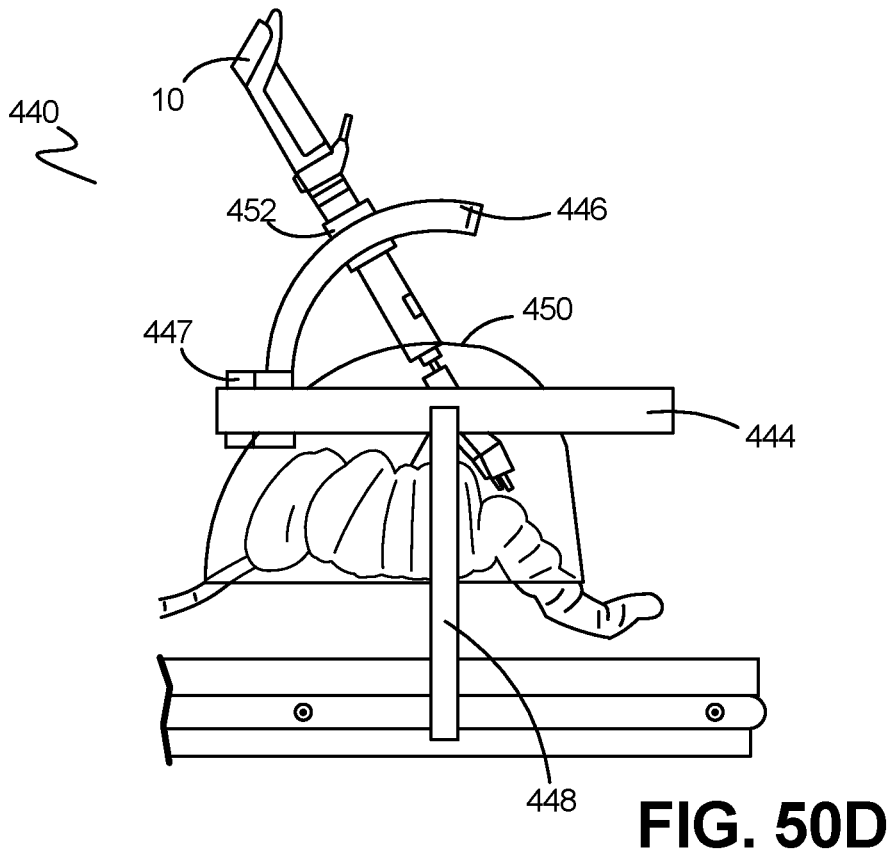
FIG. 50D is a side view of another support structure positioning the surgical device, according to one implementation.

An alternate rotating support 440 implementation for a device (such as device 10) is shown in FIGS. 50A-D. Here, a support ring 444 supported by two support arms 448 and an open arc pitch track (also referred to herein as a "pitch frame") 446 moveably coupled to the ring 444 provides both yaw (y) and pitch (p) degrees of freedom as shown in FIG. 50A. More specifically, the pitch track 446 has a coupling component 447 that is slidably coupled to the support ring 444 such that the pitch track 446 can slide along the ring 444 to different positions around the ring 444 as best shown in FIGS. 50B-50D, thereby providing the yaw (y) degree of freedom for the device 10 in which the device 10 can be rotated around as shown. It is understood that the coupling component 447 can be any mechanism or device that can be slidably coupled to the support ring 444 to allow the pitch track 446 to coupleably slide along the ring 444 as described herein.

The pitch frame 446 can be slidably positioned on the ring 444 and selectively locked into the desired position or location on the ring 444. Further, a carriage 452 is provided that is slidably coupled to the pitch track 446 and which receives the robotic device 10. That is, the robotic device 10 can be slidably coupled to the carriage 452. The carriage 452 can slide along the pitch track 446 in the direction indicated by reference letter p and can be selectively locked into the desired position or location on the track 446, thereby providing the pitch degree of freedom for the device 10 when coupled thereto. Further, because the device 10 is coupled to the carriage 452 such that it can be slidably positioned in the carriage 452 and selectively locked into the desired position in the carriage, the carriage 452 provides the translational degree of freedom for the device 10. The pitch track 446, according to one embodiment, can be any mechanism or device to which the carriage 452 or the robotic device 10 can be slidably coupled so as to provide the pitch degree of freedom. In this implementation, the pitch track 446 has a first arm 446A and a second arm 446B that are positioned to define a track space 449 therebetween such that the carriage 452 can be slidably coupled to the first and second arms 446A, 446B and slide along the track space 449. In various embodiments, the two arms 446A, 446B are curved in an arc as shown to provide for the pitch degree of freedom such that the carriage 452 moves along the arc and thereby transfers the pitch degree of freedom to the device 10.

In certain alternative embodiments, the ring 44 can be supported by one support arm or three or more support arms. In this implementation, the two support arms 448 are positioned to align the ring 444 with the insertion point 450 (which can, as with other embodiments, be an incision or a natural orifice).

Figure 51:
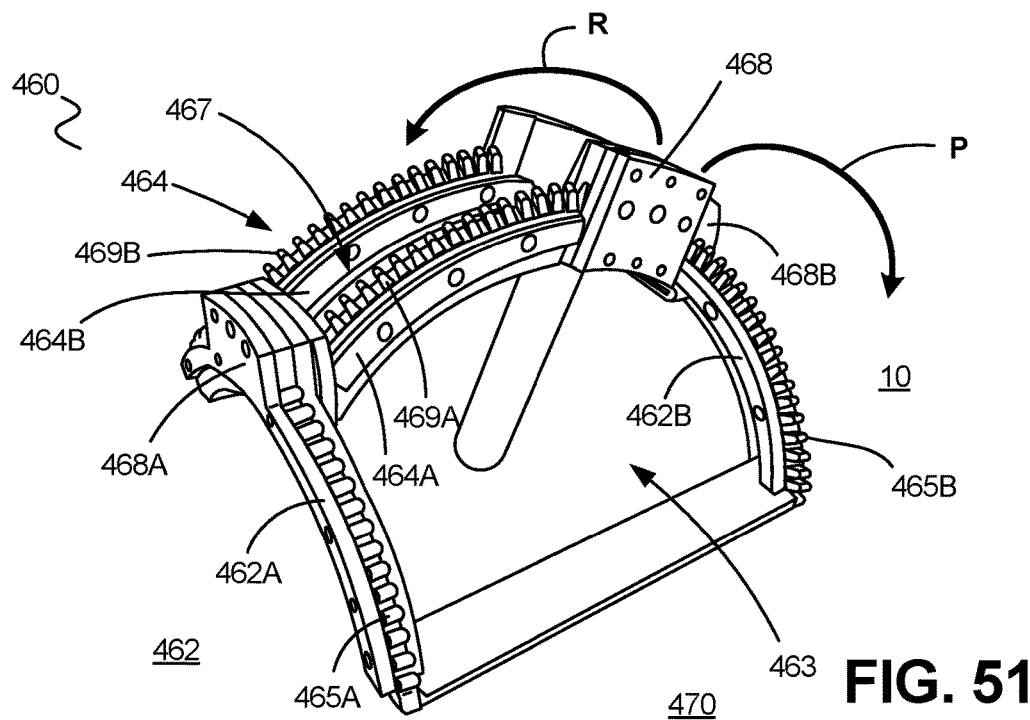
FIG. 51 is a perspective view of another support structure positioning the surgical device, according to one implementation.

Another implementation of a robotic device support 460 can be seen in FIG. 51. In this embodiment, the device support 460 has two frames: a first frame ("first track," "pitch frame," or "pitch track") 462 and a second frame ("second track," "roll frame," or "roll track") 464. The first track 462 is made up of two arms 462A, 462B that are positioned to define a track space 463 therebetween such that the second track 464 can be moveably coupled to the first and second arms 462A, 462B and move along the track space 463. In various embodiments, the two arms 462A, 462B are curved in an arc as shown such that the second track 464 moves along the arc. In this implementation, each of the two arms 462A, 462B has a gear track 465A, 465B coupled to the arms 462A, 462B as shown such that the second track 464 can couple at each end to the gear tracks 465A, 465B and thereby move along the two arms 462A, 462B.

The second track 464 is made up of two arms 464A, 464B that are positioned to define a track space 467 therebetween such that a carriage 466 can be moveably coupled to the first and second arms 464A, 464B and move along the track space 467. In various embodiments, the two arms 464A, 464B are curved in an arc as shown such that the carriage 466 moves along the arc. In this implementation, each of the two arms 464A, 464B has a gear track 469A, 469B coupled to the arms 464A, 464B as shown such that the carriage 466 can couple to the gear tracks 469A, 469B and thereby move along the two arms 464A, 464B. The two arms 464A, 464B have coupling components 468A, 468B at each end thereof that are configured to couple to the arms 462A, 462B (and related gear tracks 465A, 465B) of the first frame 462. More specifically, in this embodiment, the coupling components 468A, 468B have motors and gears (not shown) that allow for the coupling components 468A, 468B to move along the gear tracks 465A, 465B. That is, the gears (not shown) in the coupling components 468A, 468B are coupled to the gear tracks 465A, 465B respectively and the motors (not shown) can actuate those gears to turn in the appropriate direction to cause the second track 464 to move along the two arms 462A, 462B of the first track 462.

The carriage 466 is configured to receive the robotic device 10 in a fashion similar to the carriage 452 discussed above with respect to FIGS. 50A-50D. That is, the carriage 466 is moveably coupled to the second track 464 and receives the robotic device 10 such that the robotic device 10 can be slidably coupled to the carriage 466. The carriage 466 in this embodiment has motors and gears (not shown) that allow for the carriage 466 to move along the gear tracks 469A, 469B of the second track 464 in a fashion similar to the coupling components 468A, 468B described above. Alternatively, the first and second tracks 462, 464 can each be any mechanism or device to which the second track 464 or carriage 466 can be slidably coupled.

According to one implementation, the two frames 462, 464 can provide for three degrees of freedom. That is, the second frame 464 can move along the first track space 463 via the coupling components 468A, 468B moving along the first and second arms 462A, 462B, thereby providing the pitch degree of freedom for the device 10 as represented by the arrow P. Further, the carriage 466 can move along the second track space 467 by moving along the first and second arms 464A, 464B, thereby providing the roll degree of freedom for the device 10 as represented by the arrow R. In addition, the device 10 is slideably positioned in the carriage 466 such that it can moved translationally toward and away from the surgical space, thereby providing the translational degree of freedom for the device 10. It is also understood that a fourth degree of freedom can be provided by coupling this support 460 to a rotatable support ring (such as the ring 444 discussed above) to achieve a yaw degree of freedom, thereby providing for positioning the robot 10 in three degrees of freedom (pitch, roll, and yaw as described herein) around a center of rotation 470, along with the translational degree of freedom.

FIG. 52 depicts another support embodiment 500 having a track 502 along which the robotic device 10 can move in a similar fashion to the carriage embodiments discussed above. It is understood that the track 502 can have any of the features described above with respect to other track embodiments. A handle 504 is coupled to one end of the track 502 and can slide the track 502 translationally or rotate the track 502. More specifically, the handle 504 has an inner component 504B and an outer component 504A that is slideable in relation to the inner component 504B. Further, the handle 504 is coupled to the track 502 such that when the outer component 504A is slid in relation to the inner component 504B, the outer component 504A moves the track 502 in the same translational direction as indicated by arrow T. For example, when the outer component 504A is urged distally toward the surgical space (represented by the sphere S), the track 502 is also urged toward the surgical space in the direction reflected by arrow T, and when the outer component 504A is urged away, the track 502 is also urged away. In addition, the entire handle 504 can also be rotated around its own longitudinal axis, thereby urging the track 502 to rotate in the same direction as arrow P, thereby resulting in the pitch degree of freedom. Further, the device 10 can be slidably or otherwise moveably coupled to the track 502 such that it can be urged translationally toward or away from the surgical space and can be rotated around its own longitudinal axis.

Figure 52A:
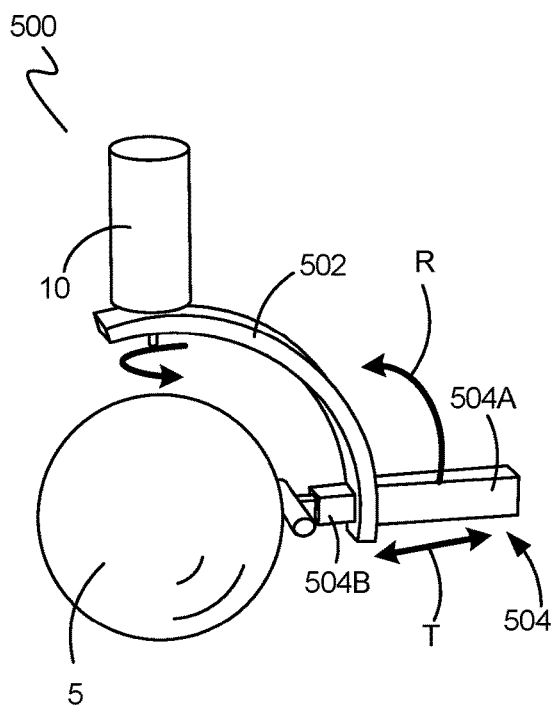
FIG. 52A is a side view of another support structure positioning the surgical device, according to one implementation.
Figure 52B:
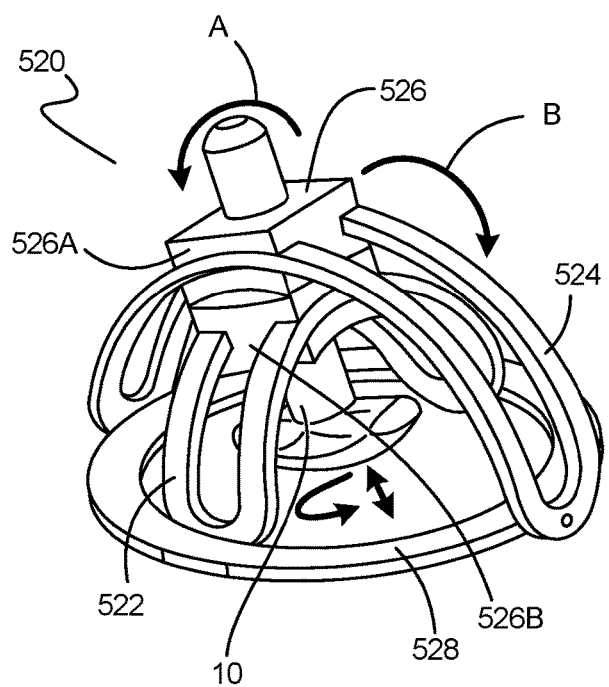
FIG. 52B is a perspective view of another support structure positioning the surgical device, according to one implementation.

A further support embodiment 520 is depicted in FIG. 52B. In this embodiment, the support 520 has two tracks 522, 524 that are coupled or "in parallel." That is, the support 520 has a single carriage 526 that is coupled to both the first and second tracks 522, 524, thereby resulting in coupled movement of the carriage 526 in relation to the two tracks 522, 524. It is understood that the two tracks 522, 524 can be structured in a similar fashion to and have similar features to the previous track embodiments discussed above. Further, the carriage 526 can be similar to the previously described carriage embodiments, except with respect to the fact that the instant carriage 526 is directly coupled to both of the tracks 522, 524 as depicted. That is, in this implementation, the carriage 526 has two portions (or segments): a top or first portion 526A that is moveably coupled to the second track 524 and a bottom or second portion 526B that is moveably coupled to the first track 522.

When the carriage 526 slides along the first track 522, the second track 524 and the robot 10 rotate as reflected in arrow A. When the carriage 526 slides along the second track 524, the first track 522 and the robot 10 rotate as reflected in arrow B. Further, as in other carriage embodiments discussed above, the carriage 526 receives the robotic device 10 such that the robotic device 10 can be slidably coupled to the carriage 526, thereby providing the translational degree of freedom for the device 10. In addition, according to certain embodiments, the two tracks 522, 524 can be coupled to a rotational support ring 528 such that both the tracks 522, 524 (along with the carriage 526 and device 10) can rotate with the ring 528 or in relation to the ring 528 in a fashion similar to the rotational ring embodiments discussed above.

Figure 52C:
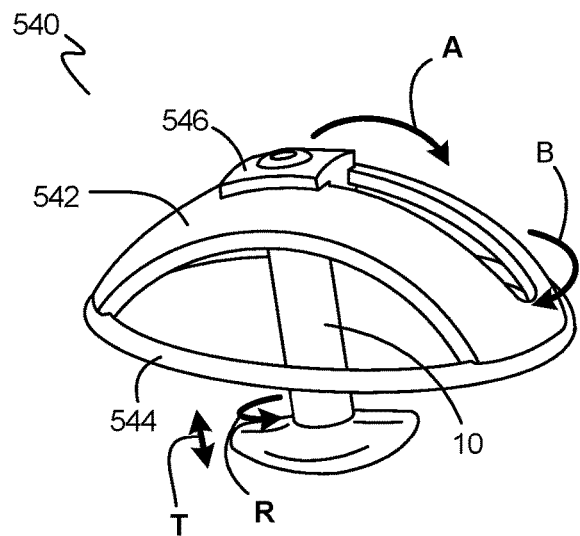
FIG. 52C is a perspective view of another support structure positioning the surgical device, according to one implementation.

FIG. 52C depicts a further implementation of a support 540. In this implementation, the support 540 has a single track 542 that is rotatably positioned on a ring support 544. A carriage 546 is moveably coupled to the track 542. It is understood that the track 542 can be structured in a similar fashion to and have similar features to the previous track embodiments discussed above. Further, the carriage 546 can be similar to the previously described carriage embodiments.

When the carriage 546 slides along the track 542, the robot 10 rotates as reflected by arrow A. When the track 542 is rotated in relation to the support ring 544 (or, alternatively, the ring 544 is rotated), the carriage 546 and the robot 10 rotate as reflected in arrow B. Further, as in other carriage embodiments discussed above, the carriage 546 receives the robotic device 10 such that the robotic device 10 can be slidably coupled to the carriage 546, thereby providing the translational degree of freedom for the device 10.

Figure 52D:
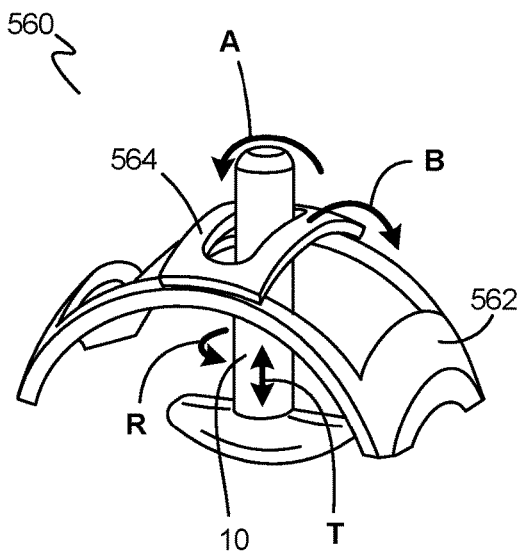
FIG. 52D is a perspective view of another support structure positioning the surgical device, according to one implementation.

Another embodiment of a robotic device support 560 can be seen in FIG. 52D. In this embodiment, the device support 560 has two frames: a first frame or track 562 and a second frame or track 564. The two frames 562, 564 are coupled to each other in a fashion similar to the frames 462, 464 in the support 460 discussed in detail above. That is, the second track 564 can be moveably coupled to and move along the first track 562. Either or both of the tracks 562, 564 can have gear tracks as described above. Alternatively, the tracks 562, 564 can have any configuration disclosed or contemplated herein with respect to tracks. In certain implementations, the second track 564 has coupling components (not shown) at each end that are configured to moveably couple to the first frame 562. Alternatively, the second track 546 can be moveably coupled to the first track 562 in any fashion.

According to one embodiment, the device 10 can be coupled to the support 560 via a carriage (not shown), which can be configured according to any carriage embodiment disclosed or contemplated herein. Alternatively, the device 10 can be coupled directly to the track 564 such that the device 10 can be movably coupled to the track 564. As such, the device 10 can move along the track 564 as reflected by arrow A, can move toward or away from the surgical space, resulting in the translational degree of freedom as reflected by arrow T, and can rotate around its own longitudinal axis as reflected by arrow R. In addition, the second track 564 can move along the first track 562, as reflected by arrow B. It is also understood that a further degree of freedom can be provided by coupling this support 560 to a rotatable support ring (such as any of the support ring embodiments discussed above).

Figure 52E:
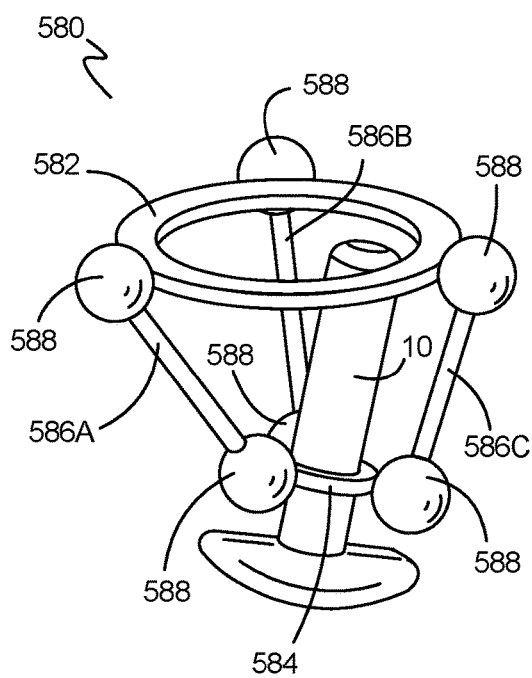
FIG. 52E is a perspective view of another support structure positioning the surgical device, according to one implementation.

FIG. 52E depicts another embodiment of a support 580. In this implementation, the support 580 utilizes ball joints. That is, the support has a first or upper ring 582 and a second or lower ring 584 that are coupled by three arms 586A, 586B, 586C. Each of the three arms 586A, 586B, 586C has ball joints 588 at each end, such that the three arms 586A, 586B, 586C are coupled at one end to the first ring 582 via ball joints 588 and at the other end to the second ring 584 via ball joints 588. The robot 10 is coupled to the second ring 584 as shown. In one embodiment, the robot 10 is slidably coupled to the second ring 584 in a fashion similar to the carriage embodiments above such that the robot 10 can be slid toward or away from the surgical space, thereby resulting in a translational degree of freedom.

It is understood that the configuration of the three arms 586A-C coupled to the two rings 582, 584 via ball joints can result in a single center of rotation for the robotic device 10 at some point below the second ring 584. As such, if the support 580 is positioned above a patient, the center of rotation can be aligned with the surgical insertion point (such as an incision) in a fashion similar to above support embodiments.

Figure 52F:
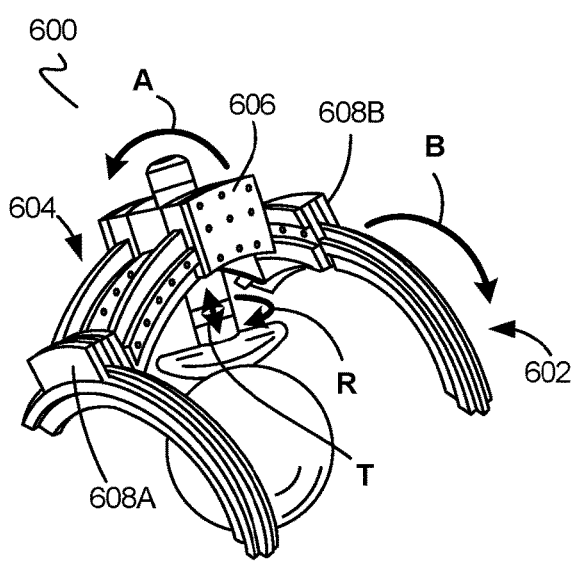
FIG. 52F is a perspective view of another support structure positioning the surgical device, according to one implementation.

A further implementation of a robotic device support 600 is shown in FIG. 52F. In this embodiment, the device support 600 has two frames: a first frame or track 602 and a second frame or track 604. The two frames 602, 604 are coupled to each other in a fashion similar to the frames 462, 464 in the support 460 or the frames 562, 564 in the support 560, both of which are discussed in detail above. That is, the second track 604 can be moveably coupled to and move along the first track 602. A carriage 606 is moveably coupled to move along the second track 604. Either or both of the tracks 602, 604 can have gear tracks as described above. Alternatively, the frames 602, 604 can have any configuration disclosed or contemplated herein with respect to frames. In certain implementations, the second track 604 has coupling components 608A, 608B at each end that are configured to moveably couple to the first frame 602. Alternatively, the second track 604 can be moveably coupled to the first track 602 in any fashion.

The carriage 606 (and thus the device 10) can move along the second frame 604 as reflected by arrow A, can move toward or away from the surgical space in relation to the carriage 606, resulting in the translational degree of freedom as reflected by arrow T, and can rotate around its own longitudinal axis as reflected by arrow R. In addition, the second track 604 can move along the first track 602, as reflected by arrow B. It is also understood that a further degree of freedom can be provided by coupling this support 600 to a rotatable support ring (such as any of the support ring embodiments discussed above).

One control console 720 implementation is shown in FIG. 53, with a main display 722 that shows the view from the robot camera (such as robotic device 10). A secondary touch screen 724 below the main display is used to interface with various functions of the robot, camera, and system. Two haptic hand controllers 726, 728 are used as user input devices in this embodiment. These haptic hand controllers 726, 728 are capable of measuring the motion of the surgeon's hands as applied at the controllers 726, 728 and applying forces and torques to those hands so as to indicate various information to the surgeon through this haptic feedback. The console 720 also has pedals 730 to control various functions of the robot. The height of the surgeon console 720 can be varied to allow the surgeon to sit or stand. Further discussion of the operation of the haptic feedback can be found in relation to U.S. patent application Ser. No. 15/227,813 and the other applications incorporated by reference herein.

FIG. 54 shows various interoperability and wiring possibilities for the system 1. Many concepts are possible, but three exemplary embodiments are given here in the context of FIG. 54. In one wiring implementation, the surgeon console 720 (or any other console disclosed or contemplated herein) interfaces with the electrosurgical generator 740. Then a "monster cable" 742 connects the surgeon console 720 to a breakout connector 744 near the surgical environment. The camera 746 and robot 10 are then connected to the breakout connector 744. In this scenario, the energy of the electrosurgical unit 740 is routed through the surgeon console 720 prior to being sent to the robot 10. In this implementation, no return pad is provided.

Alternatively, according to another wiring concept, a return pad 748 is provided that is coupled to the breakout connector 744 such that the monopolar electrosurgical energy is routed through the breakout connector 744, the monster cable 742, and the console 720 before returning to the electrosurgical generator 740.

In a further wiring alternative, the return pad 748 is coupled to the electrosurgical generator 740 such that the energy of the electrosurgical unit is routed through the surgeon console 720 prior to being sent to the robot 10 as a result of the monopolar electrosurgical energy being routed directly back to the electrosurgical generator 740.

Figure 55:
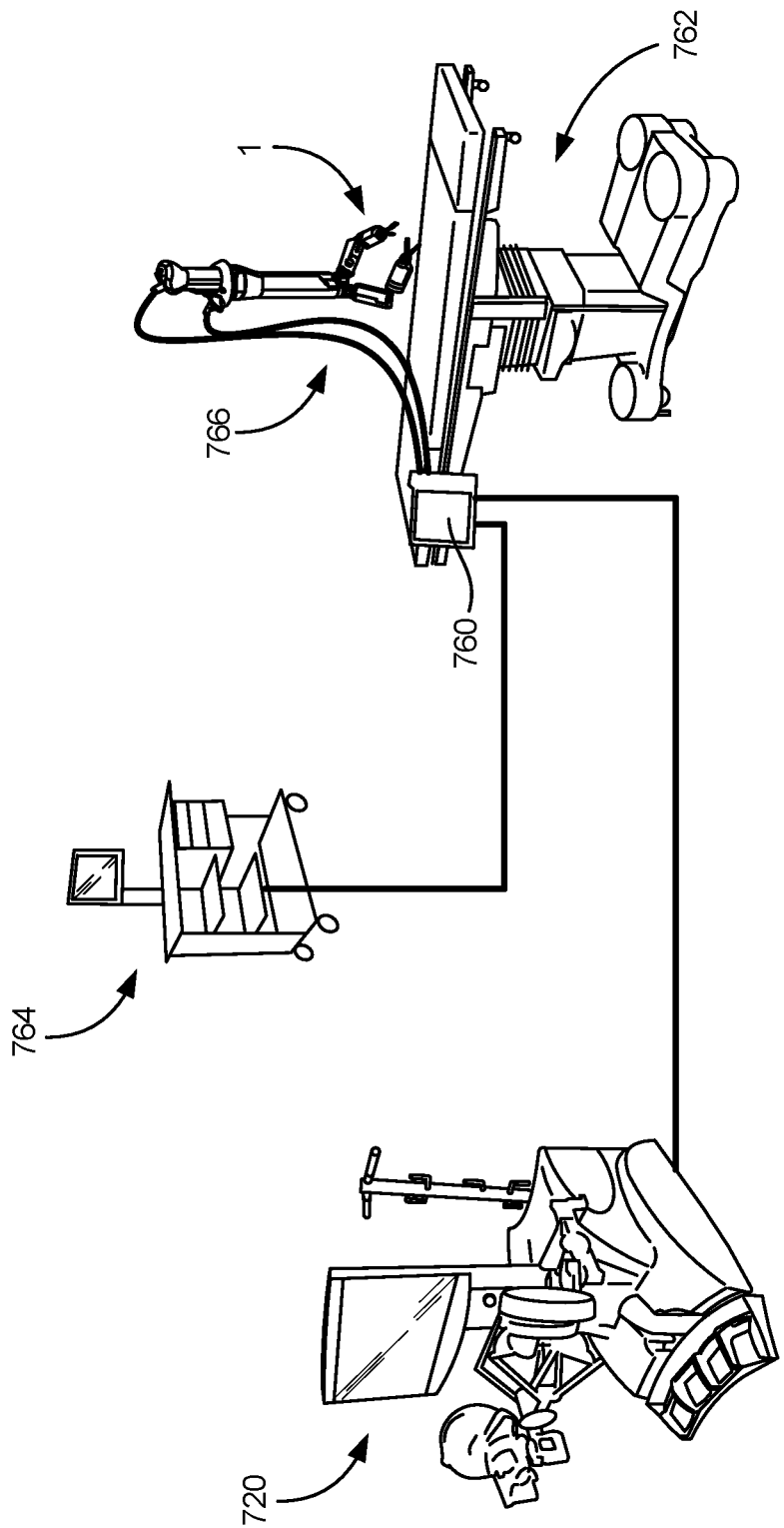
FIG. 55 is another schematic view of a surgical system, according to one implementation.

In other embodiments, the system 1 can have a cabling connector enclosure or cluster with an interface box positioned at one of several possible locations on the system 1. For example, FIG. 55 depicts the system 1 with an interface box (also referred to herein as a "pod") 760 hung on the table rail of the surgical table 762. In this embodiment, the system 1 has support electronics and equipment such as cautery, light, and other functions 764 that are coupled to the interface box 760. The console 720 is also coupled to the interface box 760. The pod 760 simplifies connections of the robot 1 in the surgical area. The pod 760 can be sterile, or not sterile and covered with a sterile drape, or not sterile at all. The function of the pod 760 is to simplify the cabling required in the surgical space and to simplify the connection of the robot and camera 1 to the surgeon console 720. The interface box 760 can be hung on the surgical table 762 inside or outside the sterile field. The box 760 in some embodiments has indicators such as lights or screens (not shown) that inform the user that a proper connection has been made and give other forms of feedback to the user. The pod 760 can also have an interface in the form of buttons, touchscreens, or other interface mechanisms to receive input from the user.

In certain alternative embodiments, the pod 760 can be placed on the floor next to or at some distance from the surgical table 762. Alternatively, the pod 760 can be hung or connected to other locations or placed on the floor outside the sterile field.

One use of this can be to mount the pod to the bed rail and then at a later time to bring in the sterile robot and camera. The robot and camera pigtails can then be handed to a non-sterile person to connect to the pod. This allows for a clean interface between the sterile and non-sterile field. The pod end could also be draped so that it could enter the sterile field and be robot and camera connections can be assembled at a sterile table so it can then be brought fully functional and sterile to the surgeon at the bedside.

The interface box can also be connected to other support electronics and equipment such as cautery, light, and other functions, and the an interface box can be designed to be on the floor or another location outside the sterile field with support electronics.

Although the disclosure has been described with reference to preferred embodiments, persons skilled in the art will recognize that changes may be made in form and detail without departing from the spirit and scope of the disclosed apparatus, systems and methods.

What is claimed is:

1. A robotic surgical device, comprising:
 a. an elongate structure;
 b. a first shoulder operably coupled to a distal end of the elongate structure, the first shoulder comprising:
  i. a first shaft;
  ii. a first gear pair wherein rotation of the first shaft drives the first gear pair; and
  iii. a second gear pair wherein the first gear pair drives the second gear pair;
 c. a second shoulder operably coupled to the distal end of the elongate structure, the second shoulder comprising:
  i. a second shaft;
  ii. a third gear pair wherein rotation of the second shaft drives the third gear pair; and
  iii. a fourth gear pair wherein the third gear pair drives the fourth gear pair; and
 d. a first robotic arm operably coupled to the first shoulder; and
 e. a second robotic arm operably coupled to the second shoulder,
 wherein the first and second robotic arms are moveable in a workspace extending from a front side to a back side of the elongate structure.

2. The robotic surgical device of claim 1, wherein the workspace extends 180 degrees from the front side to the back side of the elongate structure.

3. The robotic surgical device of claim 1, further comprising at least one actuator.

4. The robotic surgical device of claim 1, wherein the first and second robotic arms comprise at least one motor disposed within each of the first and second robotic arms.

5. The robotic surgical device of claim 1, further comprising a camera component disposed through a lumen defined in the elongate structure.

6. The robotic surgical device of claim 5, wherein the camera component is configured to be an adjustable height camera.

7. The robotic surgical device of claim 5, wherein the camera component is constructed and arranged to be capable of pitch and yaw.

8. The robotic surgical device of claim 5, wherein the camera comprises a distal tip configured to orient to a defined workspace.

9. The robotic surgical device of claim 5, wherein the camera component comprises at least one light.

10. The robotic surgical device of claim 1, further comprising first and second end effectors.

11. A robotic surgical device comprising:
 a. an elongate structure;
 b. a first shoulder operably coupled to a distal end of the elongate structure, the first shoulder comprising:
  i. a first shaft;
  ii. a first gear pair wherein rotation of the first shaft drives the first gear pair; and
  iii. a second gear pair wherein the first gear pair drives the second gear pair;

c. a second shoulder operably coupled to the distal end of the elongate structure, the second shoulder comprising:
  i. a second shaft;
  ii. a third gear pair wherein rotation of the second shaft drives the third gear pair; and
  iii. a fourth gear pair wherein the third gear pair drives the fourth gear pair;
d. a first robotic arm operably coupled to the first shoulder; and
e. a second robotic arm operably coupled to the second shoulder; and
f. a camera component disposable through a lumen in the elongate structure,
wherein the first and second shoulders are configured to allow the first and second robotic arms to be extendable to a front side and a back side of the elongate structure.

12. The robotic surgical device of claim 11, wherein the first robotic arm further comprises an upper arm and a forearm.

13. The robotic surgical device of claim 11, wherein the first robotic arm further comprises:
  a. a first arm upper arm;
  b. a first arm elbow joint; and
  c. a first arm lower arm,
  wherein the first arm upper arm is configured to be capable of roll, pitch and yaw relative to the first shoulder and the first arm lower arm is configured to be capable of yaw relative to the first arm upper arm by way of the first arm elbow joint.

14. The surgical robotic device of claim 11, wherein the first robotic arm further comprises at least one first arm actuator disposed within the first robotic arm.

15. The robotic surgical device of claim 11, wherein the second robotic arm further comprises:
  a. a second arm upper arm;
  b. a second arm elbow joint; and
  c. a second arm lower arm,
  wherein the second arm upper arm is configured to be capable of roll, pitch and yaw relative to the second shoulder and the second arm lower arm is configured to be capable of yaw relative to the second arm upper arm by way of the second arm elbow joint.

16. The surgical robotic device of claim 11, wherein the second robotic arm further comprises at least one second arm actuator disposed within the second robotic arm.

17. A robotic surgical system, comprising:
a. a robotic surgical device comprising:
  i. an elongate body comprising a lumen defined within the body, the lumen comprising:
    (A) a proximal lumen opening in a proximal end of the body;
    (B) an extended lumen portion defined distally of the proximal lumen opening; and
    (C) a distal lumen opening in a distal end of the body, the distal lumen opening defined at a distal end of the extended lumen portion;
  ii. a first shoulder operably coupled to the elongate body, the first shoulder comprising:
    (A) a first shaft;
    (B) a first gear pair, wherein rotation of the first shaft drives the first gear pair; and
    (C) a second gear pair, wherein the first gear pair drives the second gear pair;
  iii. a second shoulder operably coupled to the elongate body, the second shoulder comprising:
    (A) a second shaft;
    (B) a third gear pair, wherein rotation of the second shaft drives the third gear pair; and
    (C) a fourth gear pair, wherein the third gear pair drives the fourth gear pair;
  iv. a first robotic arm operably coupled to the first shoulder; and
  v. a second robotic arm operably coupled to the second shoulder; and
b. a camera component removably disposable through the lumen, wherein the camera component is configured and sized to be positionable through the extended lumen portion, the camera component comprising:
  (A) a rigid section;
  (B) an imager disposed in an optical section; and
  (C) a flexible section operably coupling the optical section to the rigid section,
  wherein the camera component has a length such that at least the optical section is configured to extend distally from the distal lumen opening when the camera component is positioned through the lumen.

18. The surgical robotic system of claim 17, wherein the robotic surgical device further comprises a robotic arm workspace extending from a front side to a back side of the elongate body.

19. The surgical robotic system of claim 17, wherein the first and second arms comprise at least one motor disposed in each arm.

20. The robotic surgical system of claim 17, further comprising a surgical console operably coupled to the robotic surgical device and the camera component.

* * * * *